United States Patent
Rachwal et al.

(12)

(10) Patent No.: US 6,509,366 B2
(45) Date of Patent: Jan. 21, 2003

(54) SUBSTITUTED IMIDAZOLES AS SELECTIVE MODULATORS OF BRADYKININ $B_2$ RECEPTORS

(75) Inventors: Stanislaw Rachwal, Branford, CT (US); Alan Hutchison, Madison, CT (US); Kenneth Shaw, Weston, CT (US); George D. Maynard, Clinton, CT (US); Xiao-shu He, Branford, CT (US); Robert DeSimone, Durham, CT (US); Kevin Hodgetts, Killingworth, CT (US)

(73) Assignee: Neurogen Corporation, Branford, CT (US)

( * ) Notice: Subject to any disclaimer, the term of this patent is extended or adjusted under 35 U.S.C. 154(b) by 0 days.

(21) Appl. No.: 09/764,805

(22) Filed: Jan. 17, 2001

(65) Prior Publication Data

US 2002/0115693 A1 Aug. 22, 2002

Related U.S. Application Data

(60) Provisional application No. 60/176,869, filed on Jan. 18, 2000.

(51) Int. Cl.[7] .................. A61K 31/4174; C07D 233/20; C07D 235/02
(52) U.S. Cl. .................... 514/399; 514/400; 548/338.1; 548/343.1; 548/346.1
(58) Field of Search .......................... 548/335.1, 335.5, 548/338.1, 343.1, 346.1; 514/399, 400

(56) References Cited

U.S. PATENT DOCUMENTS 5,863,950 A * 1/1999 Reich et al. ................ 514/616

FOREIGN PATENT DOCUMENTS

| WO | WO 96/00730 | 1/1996 |
| WO | WO 97/24119 | 7/1997 |
| WO | WO 99/06049 | 2/1999 |
| WO | 99/06049 | * 2/1999 |
| WO | WO 00/59886 | 10/2000 |

OTHER PUBLICATIONS

Keenan, R.M. et al., "Benzimidazole Derivatives as Arginine Mimetics in 1,4–Benzodiazepine Nonpeptide Vitronectin Recptor (αvβ3) Anatagonists", *Bioorganic & Medicinal Chemistry Letters*, (1998) 8: 3165–3170.

Reader, V.A., "An Efficient Synthesis of 2–(Methylaminomethyl)–4,5–Dialkyl–1H–Imidazoles", *SYNLETT*, (1998) 10: 1077–1078.

Ahluwalia, A. and Perretti, M. "$B_1$Receptors as a New Inflammatory Target. Could this B the 1?" Trends in Pharmacological Sciences, (1999) 20(3): 100–104.

International Search Report for PCT/US01/01618.

* cited by examiner

*Primary Examiner*—Alan L. Rotman
*Assistant Examiner*—Rita Desai
(74) *Attorney, Agent, or Firm*—Leslie-Anne Horvath; Seth A. Fidel

(57) ABSTRACT

Disclosed are compounds of the formula:

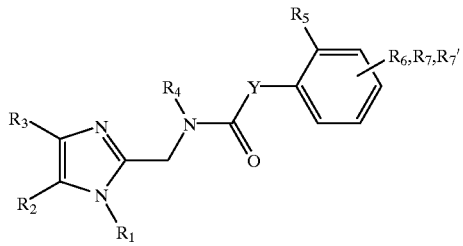

or the pharmaceutically acceptable non-toxic salts thereof wherein Y, $R_1$, $R_2$, $R_3$, $R_4$, $R_5$, $R_6$, $R_7$ $R_7'$ are variables defined herein, which compounds are modulators of Bradykinin $B_2$ receptors. These compounds are therefore useful in the diagnosis and treatment of renal diseases, heart failure, hypertension, Meniere's disease, vaginal inflammation and pain, peripheral circulatory disorders, climacteric disturbance, retinochoroidal circulatory disorders, myocardial ischemia, myocardial infarction, postmyocardial infarction syndrome, angina pectoris, restenosis after percutaneous transluminal coronary angioplasty, hepatitis, liver cirrhosis, pancreatitis, ileus, diabetes, diabetic complications, male infertility, glaucoma, pain, asthma, and rhinitis, and for the increase of permeability of the blood-brain barrier or the blood-brain-tumor barrier.

46 Claims, No Drawings

SUBSTITUTED IMIDAZOLES AS SELECTIVE MODULATORS OF BRADYKININ B$_2$ RECEPTORS

This application claims priority from U.S. provisional patent application no. 60/176,869, filed Jan. 18, 2000.

FIELD OF THE INVENTION

This invention relates to certain imidazoles which, when appropriately substituted, are selective modulators of Bradykinin B$_2$ receptors (BK-2 receptors). This invention also relates to pharmaceutical compositions comprising such compounds. It further relates to the use of such compounds in treating a variety of central and peripheral disorders. Additionally, compounds of this invention are useful as positive controls in assays for BK-2 receptor activity and when appropriately labeled as probes for the localization of BK-2 receptors in tissue sections.

BACKGROUND

Bradykinin (BK), a nonapeptide, and the closely related decapeptide kallidin (Lys-BK), are produced by proteolytic cleavage of high molecular weight kininogen by plasma kallikreins. The effects of bradykinin and kallidin are mediated by specific seven transmembrane G-protein coupled receptors.

The existence of two bradykinin receptor subtypes has been unequivocally confirmed within the last six years. The expression and cloning of a rat bradykinin receptor, now known to be a BK-2 receptor, was first reported followed by the cloning and pharmacological characterization of a human BK-2 receptor. The expression and cloning of a human bradykinin (B$_1$) receptor has also been described.

Both BK and kallidin activate the B$_2$ receptor while only kallidin is active at the B$_1$ receptor. However, both compounds are rapidly cleaved to produce B$_1$ receptor agonists, and then further degraded by kinases to produce inactive peptides. The instability of BK and kallidin suggests that these peptides act locally. Both receptors are expressed in a number of peripheral tissues as well as in the Central Nervous System (CNS).

The B$_2$ receptor is expressed constitutively in a variety of tissues and accounts for the majority of the acute pharmacological effects of bradykinin. The B$_1$ receptor is inducibly expressed and appears to act predominantly in pathophysiological conditions. The BK-1 receptor has been especially implicated in persistent hyperalgesia and chronic inflammation.

Bradykinin is an effector of a number of inflammatory responses including bronchoconstriction, plasma extravasation, release of prostaglandins/leukotrienes, smooth muscle contraction/relaxation and nociception. Bradykinin and the related peptide kallidin have been implicated in a number of disease conditions, including but not limited to pain, rhinitis, anaphylaxis, inflammatory bowel disease, vascular permeability, algesia, vasodilataion, inflammatory response, hypotension associated with sepsis, bronchopulmonary disorders including asthma, and increased cell proliferation. Antagonists of the BK-2 receptor are useful in treating these conditions. Additionally bradykinin has been implicated in increased glucose uptake, and decreased blood glucose concentration. Therefore agonists of the BK-2 receptor may be useful in the treatment of Type II diabetes. An increased permeability of the blood-brain barrier due to bradykinin has also been reported. Thus, agonists of the BK-2 receptor may also be used to increase the brain levels of pharmaceutical compounds used to treat central nervous system disorders when administered with these compounds. Therefore, compounds that modulate the bradykinin B$_2$ (BK-2) receptor as agonists or antagonists would have considerable therapeutic benefit.

A number of tissues and cultured cell lines have been assessed for the presence of bradykinin receptors using radiolabeled bradykinin or a radiolabeled bradykinin analogue as a probe (See Hall, *Gen. Pharma.*, 1997, 28: 1–6, for a compilation of such studies.). Although bradykinin and its analogues exhibit high affinity for bradykinin receptors there are some difficulties in using these ligands as receptor localization probes. Bradykinin binds to both BK-1 and BK-2 receptors and therefore cannot be used to distinguish receptor subtypes. Also bradykinin and many of its peptide analogues are susceptible to rapid degradation by kininases, leading to experimental difficulties. Nonpeptidic ligands are not susceptible to kininase activity. Therefore, small molecules that bind with high affinity and high selectivity to BK-2 receptors are especially desirable tools for BK-2 localization studies.

DESCRIPTION OF THE RELATED ART

Various compounds have been prepared as modulators of BK-2 receptors. The following disclose non-peptidic compounds that modulate Bradykinin B$_2$ receptors: EP-622361-A1, WO 98/42672, WO 97/41104, WO 97/28153, WO 96/13485, EP-596406-A1, EP-835659-A1, EP-808-838-A1, EP-796-848-A1, WO 98/03503, WO 97/24349, U.S. Pat. No. 5,438,064, U.S. Pat. No. 5,216,165, U.S. Pat. No. 5,212,182, WO 97/30048, EP 790239-A1, U.S. Pat. No. 5,510,380 and U.S. Pat. No. 5,817,756.

The compounds most closely related structurally to those of the present invention are a series of 2-[(methylamino) methyl]-4,5-dialkyl-1H-imidazoles described as vitronectin receptor antagonists and disclosed in international patent applications WO 99/06049 and WO 97/24119. These compounds are also discussed by Keenan et. al. (*Bioorg. Med. Chem. Lett.* (1998), 9(22): 3165–3170) and by Reader (*Synlett* (1998), (10): 1077–1078). The compounds described in these publications are not disclosed as bradykinin antagonists and they are not contained in the present invention.

SUMMARY OF THE INVENTION

This invention provides novel compounds of Formula I (shown below) and pharmaceutical compositions comprising compounds of Formula I. Such compounds exhibit high selectivity for bradykinin B$_2$ receptors. Compounds of Formula I also bind with high affinity to these receptors.

The invention further provides methods of treating patients suffering from certain inflammatory disorders and other conditions mediated by bradykinin. The invention also provides methods of treating patients (humans and non-humans) suffering from conditions in which agonism of the BK-2 receptor may prove beneficial. Treatment of humans, domesticated companion animals (pets) or livestock animals suffering such conditions with an effective amount of a compound of the invention is contemplated by the invention.

In a separate aspect, the invention provides methods of using compounds of this invention as positive controls in assays for BK-2 receptor activity and using appropriately labeled compounds of the invention as probes for the localization of BK-2 receptors in tissue sections.

A broad aspect of the invention is directed to compounds of Formula I:

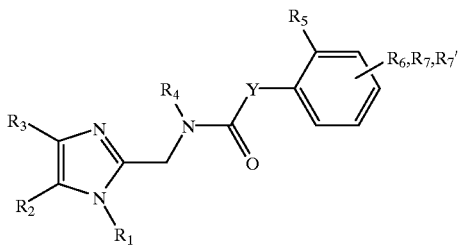

Formula I or the pharmaceutically acceptable non-toxic salts thereof wherein:

$R_1$ is arylalkyl, preferably benzyl (with the proviso that $R_1$ may not be 3-Fluorobenzyl), heteroarylalkyl preferably quinolinylmethyl or picolyl, or allyl, each of which which is optionally substituted directly or through a $O(CH_2)_n$ linker (where n=1, 2, 3 or 4) with up to three substituents independently selected from:

(i) halogen (with the proviso that $R_1$ may not be 3-Fluorobenzyl), nitro, trifluoromethyl, trifluoromethoxy, cyano, hydroxyl, $C_1$–$C_6$ alkyl, amino, $C_1$–$C_6$ alkoxy, aminomethyl, mono or di($C_1$–$C_6$)alkylamino, mono or dialkylaminomethyl, (wherein each alkyl is independently lower ($C_1$–$C_6$) alkyl), (ii) $C_1$–$C_6$alkoxyNR$_8$R$_9$, NR$_8$R$_9$, NR$_8$COR$_9$, CONR$_8$R$_9$, wherein $R_8$ and $R_9$ are the same or different and represent hydrogen, straight or branched chain lower alkyl, or $R_8$ and $R_9$ form a 5, 6, or 7 membered heterocyclic ring, which is optionally substituted with halogen, nitro, trifluoromethyl, cyano, hydroxyl, $C_1$–$C_6$ alkyl, amino, mono or di($C_1$–$C_6$) alkylamino, or $C_1$–$C_6$ alkoxy, (iii) $O(CH_2)_nCO_2R_A$ wherein n=1, 2, 3, 4, $COR_A$, and $CO_2R_A$,
wherein $R_A$ represents hydrogen, or straight or branched chain lower alkyl, (iv) $SO_2R_A$, $NHSO_2R_A$, $SO_2NHR_A$, $SO_2NHCOR_A$, $CONHSO_2R_A$,
wherein $R_A$ represents hydrogen, or straight or branched chain lower alkyl, (v) tetrazole, triazole, imidazole, thiazole, oxazole, thiophene, and pyridyl;

$R_2$ and $R_3$ are the same or different and represent (i) halogen, trifluoromethyl, trifluoromethoxy, lower alkoxy having 1–6 carbon atoms, lower alkyl, amino methyl, mono or dialkylaminomethyl, wherein each alkyl is independently lower ($C_1$–$C_6$) alkyl, (ii) $C_1$–$C_6$alkoxyNR$_8$'R$_9$', NR$_8$'R$_9$', CONR$_8$'R$_9$', NR$_8$'COR$_9$', wherein $R_8$' and $R_9$' are the same or different and represent hydrogen or straight or branched chain lower alkyl, or $R_8$' and $R_9$' is a 5, 6, or 7 membered heterocyclic ring, optionally substituted with halogen, nitro, trifluoromethyl, cyano, hydroxyl, $C_1$–$C_6$ alkyl, amino, mono or di($C_1$–$C_6$)alkylamino, or $C_1$–$C_6$ alkoxy, (iii) $O(CH_2)_nCO_2R_A$' where n=1, 2, 3, 4, $COR_A$', or $CO_2R_A$',
wherein $R_A$' represents hydrogen or straight or branched chain lower alkyl; or $R_2$ and $R_3$ may be taken together to form a carbocyclic or heterocyclic saturated ring;

$R_4$ represents straight or branched chain lower alkyl;

$R_5$ represents halogen or trifluoromethyl;

$R_6$, $R_7$ and $R_7$' are the same or different and represent (i) hydrogen, trifluoromethyl, trifluoromethoxy, nitrile, $C_1$–$C_{10}$ alkyl, $C_1$–$C_{10}$ alkoxy (with the proviso that $R_6$, $R_7$, or $R_7$' may not be $C_1$–$C_{10}$ alkoxy when located ortho to Y), $C_1$–$C_6$alkylthio, halogen, aminomethyl, di($C_1$–$C_6$)alkylamino, mono or di$C_1$–$C_6$alkylaminomethyl, or (ii) $C_1$–$C_6$ alkoxyaminoalkyl where the amino is mono or disubstituted with straight or branched chain lower alkyl;

(iii) or any two adjacent $R_6$, $R_7$ or $R_7$' may be joined to form a 5 to 7 membered ring containing 1 or 2 oxygen atoms where the remaining ring members are carbon; or $R_5$ and $R_6$ are joined to form a 5, 6, or 7 membered carbocyclic or heterocyclic aromatic ring which is optionally substituted with up to four substituents selected from:

(i) halogen, nitro, trifluoromethyl, cyano, hydroxyl, $C_1$–$C_6$ alkyl, amino, $C_1$–$C_6$ alkoxy, aminomethyl, alkylaminomethyl, mono or di($C_1$–$C_6$)alkylamino, mono or dialkylaminomethyl, wherein each alkyl is independently lower ($C_1$–$C_6$) alkyl, (ii) $C_1$–$C_6$alkoxyNR$_8$"R$_9$", NR$_8$"R$_9$", CONR$_8$"R$_9$", NR$_8$"COR$_9$", where $R_8$" and $R_9$" are the same or different and represent hydrogen or straight or branched chain lower alkyl, or $R_8$" and $R_9$" can be a 5, 6, or 7 membered heterocyclic ring, which is optionally substituted with halogen, nitro, trifluoromethyl, cyano, hydroxyl, lower alkyl, amino, mono or di($C_1$–$C_6$) alkylamino, or $C_1$–$C_6$ alkoxy, (iii) $O(CH_2)_nCO_2R_A$" where n=1, 2, 3, 4, $COR_A$", or $CO_2R_A$", wherein $R_A$" represents hydrogen or straight or branched chain lower alkyl; and $R_7$ and $R_7$' are as defined above; and Y represents a bond or $CH_2$, when Y=$CH_2$ it may be mono or disubstituted with a straight or branched chain lower alkyl, or straight or branched chain lower alkoxy having 1–6 carbon atoms.

DETAILED DESCRIPTION OF THE INVENTION

The novel compounds of Formula I may be comprised of compounds of general Formula Ia:

Formula Ia

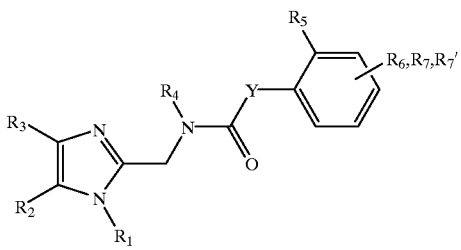

or the pharmaceutically acceptable non-toxic salts thereof wherein: $R_1$, $R_2$, $R_3$, $R_4$, and Y are as defined above;

$R_5$ represents halogen, hydrogen, or trifluoromethyl; and $R_6$, $R_7$ and $R_7$' are the same or different and represent hydrogen, trifluoromethyl, trifluoromethoxy, cyano, nitro, lower alkyl having 1–10 carbon atoms, $C_1$–$C_{10}$ alkoxy (with the proviso that $R_6$, $R_7$, or $R_7$' may not be $C_1$–$C_{10}$ alkoxy when located ortho to Y in Formula Ia), halogen, aminomethyl, mono or dialkylaminomethyl where each alkyl is independently lower ($C_1$–$C_6$) alkyl, and $C_1$–$C_6$ alkoxyaminoalkyl where the amino is mono or disubstituted with straight or branched chain lower alkyl having 1–6 carbon atoms.

Preferred compounds of the invention are comprised of compounds of Formula I or Formula Ia, and the pharmaceutically acceptable salts thereof, wherein $R_1$, $R_4$, $R_5$, $R_6$, $R_7$, $R_7'$ and Y are as defined for Formula I or Formula Ia with the restriction that $R_2$ and $R_3$ do not form a carbocyclic or heterocyclic ring.

Other novel compounds of Formula I may be comprised of compounds of general Formula Ib:

Formula Ib

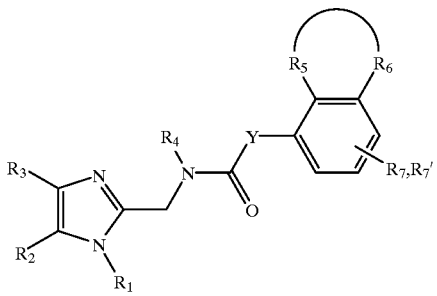

or the pharmaceutically acceptable non-toxic salts thereof wherein: $R_1$, $R_2$, $R_3$, $R_4$, and Y are as defined above;

$R_5$ is part of an aromatic ring formed with $R_6$;

$R_6$ is part of an 5, 6, or 7 membered aromatic ring which is optionally substituted with halogen, nitro, trifluoromethyl, cyano, hydroxyl, $C_1$–$C_6$ alkyl, amino, or mono or di($C_1$–$C_6$) alkylamino, $C_1$–$C_6$ alkoxy, aminomethyl, alkylaminomethyl or mono or dialkylaminomethyl where each alkyl is independently lower ($C_1$–$C_6$) alkyl, $C_1$–$C_6$ alkoxyaminoalkyl (for example $OCH_2CH_2NR_8"R_9"$), $NR_8"R_9"$, $CONR_8"R_9"$, $NR_8"COR_9"$, where $R_8"$ and $R_9"$ are the same or different and represent hydrogen or straight or branched chain lower alkyl having 1–6 carbon atoms, additionally $R_8"$ and $R_9"$ can be a 5, 6, or 7 membered heterocyclic ring, which may be optionally substituted with halogen, nitro, trifluoromethyl, cyano, hydroxyl, $C_1$–$C_6$ alkyl, amino, mono or di($C_1$–$C_6$) alkylamino, or $C_1$–$C_6$ alkoxy;

$O(CH_2)_nCO_2R_8"$ where n=1, 2, 3, 4, $COR_8"$, or $CO_2R_8"$, where $R_8"$ represents hydrogen or straight or branched chain lower alkyl having 1–6 carbon atoms; and $R_7$ and $R_7'$ represent hydrogen, trifluoromethyl, trifluoromethoxy, cyano or nitro, lower alkyl having 1–10 carbon atoms, $C_1$–$C_{10}$ alkoxy (with the proviso that $R_6$, $R_7$, or $R_7'$ may not be $C_1$–$C_{10}$ alkoxy when located ortho to Y in Formula Ib), halogen, aminomethyl, mono or dialkylaminomethyl where each alkyl is independently lower ($C_1$–$C_6$) alkyl, or $C_1$–$C_6$ alkoxyaminoalkyl where the amino is mono or disubstituted with straight or branched chain lower alkyl having 1–6 carbon atoms.

Preferred compounds of Formula Ib include those compound in which $R_1$, $R_4$, $R_5$, $R_6$, $R_7$, and $R_7'$ are as defined for Formula Ib and $R_2$ and $R_3$ are defined as for Formula Ib with the restriction that $R_2$ and $R_3$ do not form a ring.

One preferred embodiment of the present invention encompasses compounds of Formula II and the pharmaceutically acceptable salts thereof;

Formula II

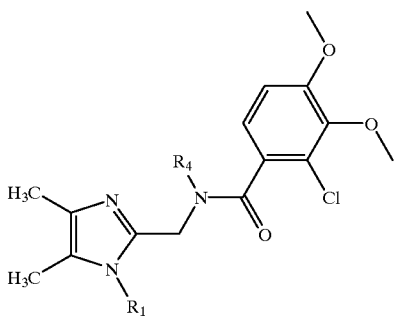

wherein $R_1$ and $R_4$ are as defined above.

In a more preferred embodiment the invention encompasses compounds of Formula II and the pharmaceutically acceptable salts thereof wherein $R_4$ is isoamyl or n-pentyl, and $R_1$ is as defined above.

In another preferred embodiment, the present invention encompasses compounds of Formula III, and the pharmaceutically acceptable salts thereof;

Formula III

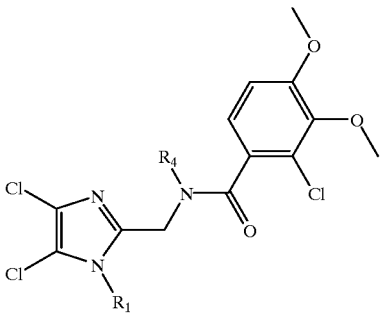

wherein $R_1$ and $R_4$ are as defined above.

In a more preferred embodiment the invention encompasses compounds of Formula III and the pharmaceutically acceptable salts thereof wherein $R_4$ is iso amyl or n-pentyl, and $R_1$ is as defined above.

In certain situations, the compounds of Formula I may contain one or more asymmetric carbon atoms, so that the compounds can exist in different stereoisomeric forms. These compounds can be, for example, racemates or optically active forms. In these situations, the single enantiomers, i.e., optically active forms, can be obtained by asymmetric synthesis or by resolution of the racemates. Resolution of the racemates can be accomplished, for example, by conventional methods such as crystallization in the presence of a resolving agent, or chromatography, using, for example a chiral HPLC column.

Representative compounds of the present invention, which are encompassed by Formula I, include, but are not limited to the compounds described in the Examples and their pharmaceutically acceptable acid addition salts. In addition, if the compound of the invention is obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds.

Non-toxic pharmaceutical salts include salts of acids such as hydrochloric, phosphoric, hydrobromic, sulfuric, sulfinic, formic, toluenesulfonic, methanesulfonic, nitric, benzoic, citric, tartaric, maleic, hydroiodic, alkanoic such as acetic, $HOOC-(CH_2)n-COOH$ where n is 0–4, and the like. Those skilled in the art will recognize a wide variety of non-toxic pharmaceutically acceptable addition salts.

The present invention also encompasses the acylated prodrugs of the compounds of Formula I. Those skilled in the art will recognize various synthetic methodologies which may be employed to prepare non-toxic pharmaceutically acceptable addition salts and acylated prodrugs of the compounds encompassed by Formula I.

When any variable occurs more than one time in any constituent or formula for a compound, its definition at each occurrence is independent of its definition at every other occurrence. Thus, for example, if a group is shown to be substituted with 0–2 R*, then said group may optionally be substituted with up to two R* groups and R* at each occurrence is selected independently from the definition of R*. Also, combinations of substituents and/or variables are permissible only if such combinations result in stable compounds.

The term "aryl" in the present invention means a monocyclic or bicyclic aromatic group having preferably 6 to 10 carbon atoms, such as, for example, phenyl or naphthyl.

By "arylalkyl" or "heteroarylalkyl" in the present invention is meant a branched or straight-chain alkyl group having from 1 to about 6 carbon atoms and substituted on one of the carbon atoms by an optionally substituted aryl or heteroaryl ring, such as, for example, benzyl, phenethyl, methylpyridyl, ethylpyridyl, and the like.

By "alkyl" in the present invention is meant $C_1$–$C_{10}$ alkyl, i.e., straight or branched chain alkyl groups having 1–10 carbon atoms, preferably 1–6 carbon atoms ($C_1$–$C_6$ alkyl), such as, for example, methyl, ethyl, propyl, isopropyl, n-butyl, sec-butyl, tert-butyl, pentyl, 2-pentyl, isopentyl, neopentyl, hexyl, 2-hexyl, 3-hexyl, and 3-methylpentyl. Preferred $C_1$–$C_{10}$ alkyl groups are methyl, ethyl, propyl, butyl, cyclopropyl or cyclopropylmethyl.

By "lower alkyl" in the present invention is meant $C_1$–$C_6$ alkyl, i.e., straight or branched chain alkyl groups having 1–6 carbon atoms.

By "alkoxy" or "lower alkoxy" in the present invention is meant $C_1$–$C_6$ alkoxy, i.e., straight or branched chain alkoxy groups having 1–6 carbon atoms, such as, for example, methoxy, ethoxy, propoxy, isopropoxy, n-butoxy, sec-butoxy, tert-butoxy, pentoxy, 2-pentyl, isopentoxy, neopentoxy, hexoxy, 2-hexoxy, 3-hexoxy, and 3-methylpentoxy.

By "halogen" in the present invention is meant fluorine, bromine, chlorine, and iodine.

By "(hetero) cyclic ring" is meant a ring that is either aliphatic or aromatic and optionally contains at least one hetero atom. Hetero atoms include nitrogen, sulfur, and oxygen. Examples of such (hetero) cyclic rings are cyclohexyl, cyclopentyl, piperidinyl, piperazinyl, pyrrolidinyl, morpholinyl, etc.

By "heteroaryl" (aromatic heterocycle) in the present invention is meant one or more aromatic ring systems of 5-, 6-, or 7-membered rings containing at least one and up to four hetero atoms selected from nitrogen, oxygen, or sulfur. Such heteroaryl groups include, for example, thienyl, furanyl, thiazolyl, imidazolyl, (is)oxazolyl, pyridyl, pyrimidinyl, imidazolyl, (iso)quinolinyl, naphthyridinyl, benzimidazolyl, and benzoxazolyl.

Specific examples of heteroaryl groups are the following:

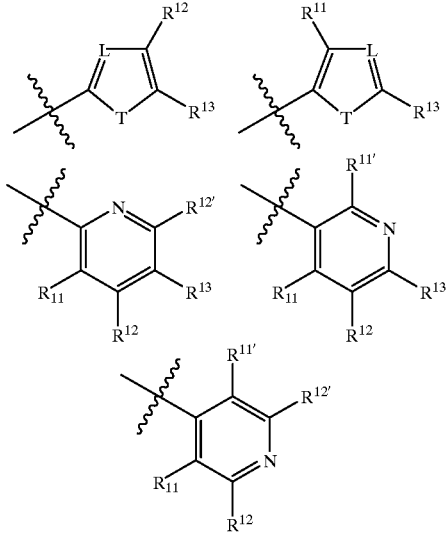

wherein:
L is nitrogen or —$CR^{11}$;
T is —$NR^{19}$, oxygen, or sulfur;
$R^{11}$ and $R^{11'}$ are the same or different and are selected from: hydrogen, halogen, hydroxy, $C_1$–$C_6$ alkyl, ($C_1$–$C_6$)alkoxy, amino, or mono- or di($C_1$–$C_6$)alkylamino;
$R^{12}$, $R^{12'}$, and $R^{13}$ are the same or different and are selected from hydrogen, halogen, ($C_1$–$C_6$)alkyl, ($C_1$–$C_6$)alkoxy, amino, mono- or di($C_1$–$C_6$)alkylamino, hydroxy, or trifluoromethyl; and
$R^{19}$ is hydrogen, or lower alkyl having 1–6 carbon atoms.

The structure of Formula I as shown in the specification and as used in the claims includes all possible tautomers and rotamers.

The invention also provides pharmaceutical composition comprising compounds of the invention.

The invention also provides packaged pharmaceutical compositions comprising pharmaceutical compositions of the invention in a container and instructions for using the composition to treat a patient in need thereof. In one embodiment, the instructions are for using the composition for treating a patient suffering from a physiological disorder associated with an excess of or insufficient amount of bradykinin. The patient may be suffering, for example, from renal disease, heart failure, hypertension, Meniere's disease, vaginal inflammation and pain, peripheral circulatory disorders, climacteric disturbance, retinochoroidal circulatory disorders, myocardial ischemia, myocardial infarction, postmyocardial infarction syndrome, angina pectoris, restenosis after percutaneous transluminal coronary angioplasty, hepatitis, liver cirrhosis, pancreatitis, ileus, diabetes, diabetic complications, male infertility or glaucoma, asthma, rhinitis, brain cancer, or a brain tumor.

The invention further provides methods of treating patients in suffering from an inflammatory disorder with an amount of a compound of the invention sufficient to alter the symptoms of the inflammatory disorder. Inflammatory disorders that may be treated with a selective antagonist of the BK-2 receptor include restenosis after percutaneous transluminal coronary angioplasty, rhinitis, inflammation associated with brain trauma, stroke, sepsis, anaphylaxis, Meniere's disease, pancreatitis, ileus, inflammatory bowel disease, and bronchopulmonary disorders including asthma. The invention also provides methods of treating patients suffering from pain with a pain-reducing amount of a compound of the invention. Painful conditions that may be treated with an antagonist of the BK-2 receptor, include, but are not limited to inflammatory pain, postoperative pain, and vaginal inflammation and pain. The invention further provides a method of treating patients suffering from hypertension with an amount of compound of the invention sufficient to reduce blood pressure. Selective antagonists of the BK-2 receptor are useful as anti-hypertensives.

In a further aspect the invention provide a method of treating a patient suffering from Type II (adult-onset) diabetes with an amount of a compound of the invention sufficient to alter the symptoms. Selective agonists of the BK-2 receptor are useful for treating type II diabetes. The invention also provides methods of treating patients suffering from circulatory or cardiovascular disorders with an amount of a compound of the invention, that is a selective agonist of the BK-2 receptor, sufficient to reduce the symptoms of the circulatory of cardiovascular disorder. Such circulatory or cardiovascular disorders include, but are not limited to heart failure, peripheral circulatory disorders, myocardial infarction, postmyocardial infarction syndrome, angina pectoris, retinochoroidal circulatory disorders, and myocardial ischemia. Selective agonists of the BK-2 stimulate NO release and as such are useful for treating climacteric disturbance and male infertility. The invention provides methods of treating patients suffering from such disorders with an amount of a compound of the invention sufficient to reduce the symptoms of disorder.

Bradykinin has been shown to increase the permeability of blood-brain barrier and blood-brain tumor barrier. The invention provides a method of increasing the brain concentration of a CNS active compounds which comprises administering a patient in need of such treatment a compound of the invention, that is a selective agonist of the BK-2 receptor, along with a CNS active compound, and thereby increasing the brain concentration of the CNS active compound. In a particularly preferred embodiment the invention provides a method of increasing the brain concentration of anti-cancer and anti-tumor agents which comprises administering a patient suffering from brain cancer or a brain tumor a compound of the invention, that is a selective agonist of the BK-2 receptor, along with a anti-cancer and anti-tumor agent, and thereby increasing the brain concentration of the anti-cancer or anti-tumor agent.

Patients include human and non-human animals, such as domestic pets and farm animals (for example, dogs, cats, swine, sheep, horses, cattle, etc.).

The present invention also pertains to methods of inhibiting the binding of bradykinin to the bradykinin receptors, especially BK-2 receptors which methods involve contacting a compound of the invention with cells expressing bradykinon receptors, (preferably BK-2 receptors) wherein the compound is present at a concentration sufficient to inhibit the binding of bradykinin to bradykinin receptors in vitro. This method includes inhibiting the binding of bradykinin to bradykinin receptors in vivo, e.g., in a patient given an amount of a compound of formula I or any of the subformulae thereof, that would be sufficient to inhibit the binding of bradykinon to BK-2 receptors in vitro. The amount of a compound that would be sufficient to inhibit the binding bradykinin to the BK-2 receptor may be readily determined via a BK-2 receptor binding assay, such as the assay described in Example 8. The BK-2 receptors used to determine in vitro binding may be obtained from a variety of sources, for example from preparations of rat brain or from cells expressing cloned human BK-2 receptors.

The present invention also pertains to methods for altering the signal-transducing activity of bradykinin receptors, said method comprising exposing cells expressing such receptors to an effective amount of a compound of the invention. This method includes altering the signal-transducing activity of BK-2 receptors in vivo, e.g., in a patient given an amount of a compound of formula I, or the subformulae thereof, that would be sufficient to alter the signal-transducing activity of BK-2 receptors in vitro. The amount of a compound that would be sufficient to alter the signal-transducing activity of bradykinin receptors may be determined via a bradykinin receptor signal transduction assay, such as the assay described in Example 9. The bradykinin receptor ligands (i.e. the compounds of the invention) provided by this invention and labeled derivatives thereof are also useful as standards and reagents in determining the ability of a potential pharmaceutical to bind to the BK-2 receptor.

Isotopically-labeled compounds of this invention, which are identical to those recited in formula I, or the subformulae thereof, but for the fact that one or more atoms are replaced by an atom having an atomic mass or mass number different from the atomic mass or mass number usually found in nature, are also useful for mapping the location of bradykinin receptors (e.g., in tissue sections via autoradiography) and as radiotracers for positron emission tomography (PET) imaging, single photon emission computerized tomography (SPECT), and the like, to characterize such receptors in living subjects. Examples of isotopes that can be incorporated into compounds of the invention include isotopes of hydrogen, carbon, nitrogen, oxygen, phosphorous, fluorine and chlorine, such as $^2H$, $^3H$, $^{11}C$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Compounds of the present invention, prodrugs thereof, and pharmaceutically acceptable salts of said compounds or of said prodrugs which contain the aforementioned isotopes and/or other isotopes of other atoms are within the scope of this invention. In addition, substitution with heavy isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labeled compounds of formula Ia, or the subformulae thereof, of this invention and prodrugs thereof can generally be prepared by carrying out the procedures disclosed in the Schemes and/or in the examples below, by substituting a readily available isotopically labeled reagent for a non-isotopically labeled reagent.

Pharmaceutical Preparations

The compounds of general Formula I may be administered orally, topically, parenterally, by inhalation or spray or rectally in dosage unit formulations containing conventional non-toxic pharmaceutically acceptable carriers, adjuvants and vehicles. The term parenteral as used herein includes percutaneous, subcutaneous, intravascular (e.g., intravenous), intramuscular, or intrathecal injection or infusion techniques and the like. In addition, there is provided a pharmaceutical formulation comprising a compound of general Formula I and a pharmaceutically acceptable carrier. One or more compounds of general Formula I may be present in association with one or more non-toxic pharmaceutically acceptable carriers and/or diluents and/or adjuvants and if desired other active ingredients. The pharmaceutical compositions containing compounds of general Formula I may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preservative agents in order to provide pharmaceutically elegant and palatable preparations. Tablets contain the active ingredient in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques. In some cases such coatings may be prepared by known techniques so as to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents and flavoring agents may be added to provide palatable oral preparations. These compositions may be preserved by the addition of an antioxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil or a mineral oil or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monoleate, and condensation products of the said partial esters with ethylene oxide, for example polyoxyethylene sorbitan monoleate. The emulsions may also contain sweetening and flavoring agents.

Syrups and elixirs may be formulated with sweetening agents, for example glycerol, propylene glycol, sorbitol, glucose or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents that have been mentioned above. The sterile injectable preparation may also be sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono-or diglycerides. In addition, fatty acids such as oleic acid find use in the preparation of injectables.

The compounds of general Formula I may also be administered in the form of suppositories, e.g., for rectal administration of the drug. These compositions can be prepared by mixing the drug with a suitable non-irritating excipient that is solid at ordinary temperatures but liquid at the rectal temperature and will therefore melt in the rectum to release the drug. Such materials are cocoa butter and polyethylene glycols.

Compounds of general Formula I may be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

Dosage levels of the order of from about 0.1 mg to about 140 mg per kilogram of body weight per day are useful in the treatment of the above-indicated conditions (about 0.5 mg to about 7 g per patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

Preferred compounds of the invention will have certain pharmacological properties. Such properties include, but are not limited to oral bioavailability, low toxicity, low serum protein binding and desirable in vitro and in vivo half-lives. Penetration of the blood brain barrier for compounds used to treat CNS disorders is necessary, while low brain levels of compounds used to treat peripheral disorders are often preferred.

Assays may be used to predict these desirable pharmacological properties. Assays used to predict bioavailability include transport across human intestinal cell monolayers, including Caco-2 cell monolayers. Toxicity to cultured hepatocytes may be used to predict compound toxicity. Penetration of the blood brain barrier of a compound in humans may be predicted from the brain levels of the compound in laboratory animals given the compound intravenously.

Serum protein binding may be predicted from albumin binding assays. Such assays are described in a review by Oravcová, et al. (*Journal of Chromatography B* 1996, 677, 1–27).

Compound half-life is inversely proportional to the frequency of dosage of a compound. In vitro half-lives of compounds may be predicted from assays of microsomal half-life as described by Kuhnz and Gieschen (*Drug Metabolism and Disposition* 1998, 26, 1120–1127).

As discussed above, preferred compounds of the invention exhibit good activity in in vitro Bradykinin receptor binding assays, especially BK-2 receptor binding assays, and specifically the assay as specified in Example 8, which follows. References herein to "in vitro BK-2 receptor binding assay" are intended to refer to that protocol as defined in Example 8 which follows.

For administration to non-human animals, the composition may also be added to the animal feed or drinking water. It will be convenient to formulate these animal feed and drinking water compositions so that the animal takes in an appropriate quantity of the composition along with its diet. It will also be convenient to present the composition as a premix for addition to the feed or drinking water.

EXAMPLES

Compounds of the invention can be prepared using the reactions depicted in Schemes 1 to 3.

Scheme I

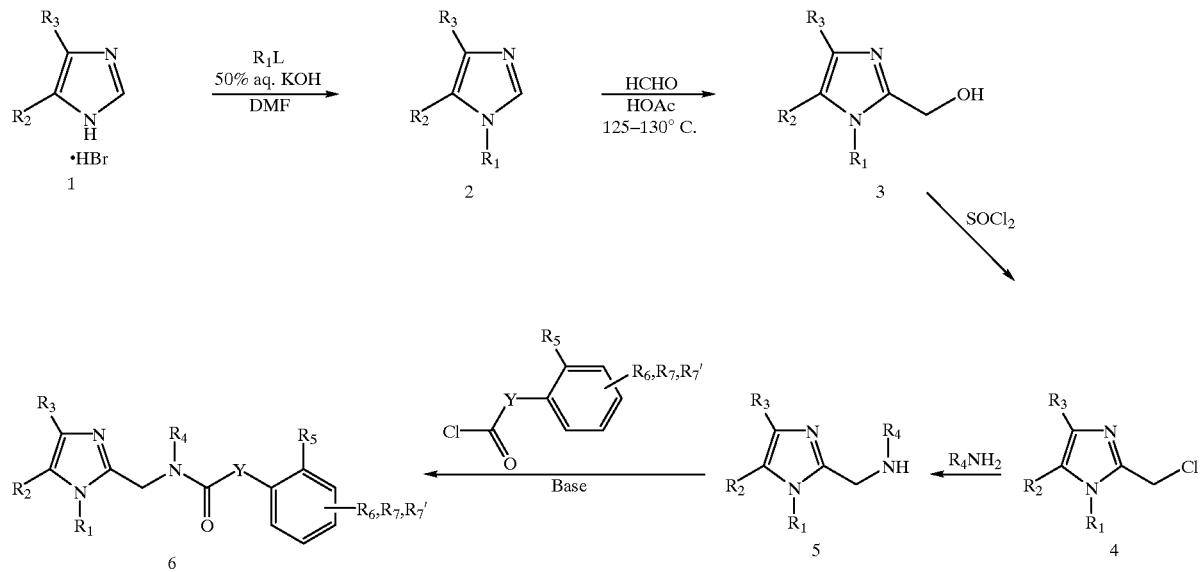

In Scheme 1, L represents an appropriate leaving group such as chloride, bromide, iodide or mesylate. The groups $R_1$, $R_2$, $R_3$, $R_4$, $R_5$, $R_6$, $R_7$, $R_7'$ and Y are as defined as Formula I.

Alternatively, appropriately protected forms of $R_1$, $R_2$, $R_3$, $R_4$, $R_5$, $R_6$, $R_7$ and $R_7'$ may be employed. In such cases, an additional deprotection step is employed to obtain the final product. Suitable protecting groups and conditions are readily available (e.g. "Protective Groups in Organic Synthesis" by T. W. Greene). Suitable conditions for carrying out the transformations in Scheme 1 are exemplified but not limited to those given in Example 1. Those skilled in the art will realize that alternate synthetic methods may be employed to accomplish the reactions in Scheme 1.

Scheme 2

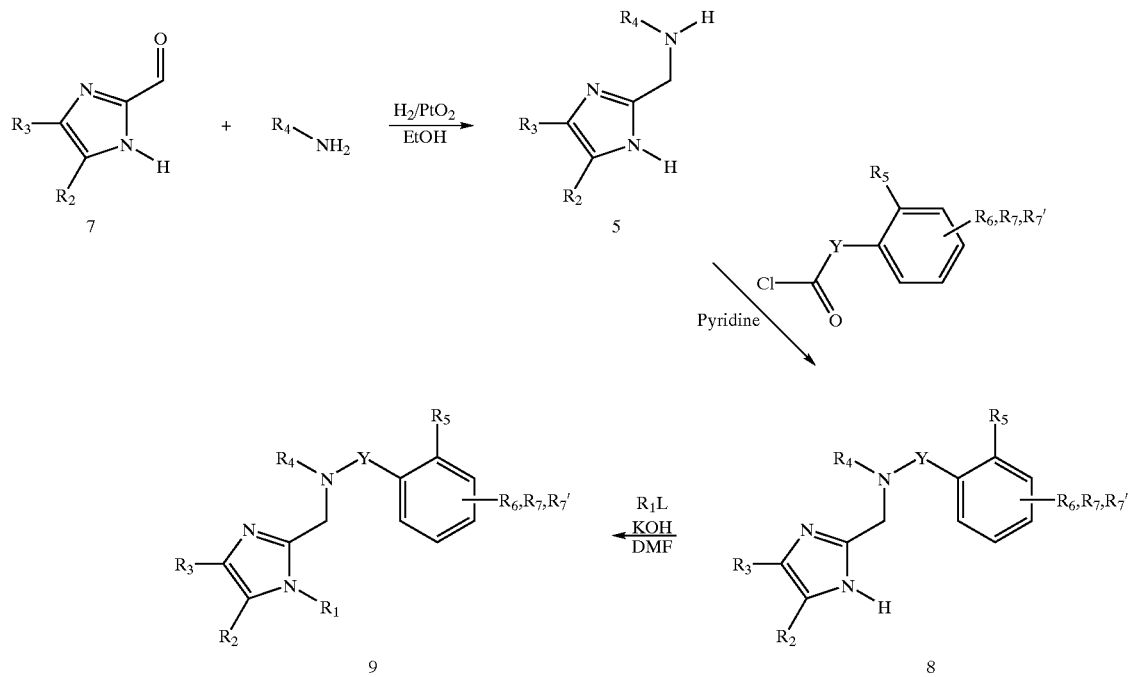

In Scheme 2, L represents an appropriate leaving group such as chloride, bromide, iodide or mesylate. The groups $R_1$, $R_2$, $R_3$, $R_4$, $R_5$, $R_6$, $R_7$, $R_7'$ and Y are as defined as Formula I.

Alternatively, appropriately protected forms of $R_1$, $R_2$, $R_3$, $R_4$, $R_5$, $R_6$, $R_7$ and $R_7'$ may be employed. In such cases, an additional deprotection step is employed to obtain the final product. Suitable protecting groups and conditions are readily available (e.g. "Protective Groups in Organic Synthesis" by T. W. Greene). Suitable conditions for carrying out the transformations in Scheme 2 are exemplified but not limited to those given in Example 2. Those skilled in the art will realize that alternate synthetic methods may be employed to accomplish the reactions in Scheme 2.

groups and conditions are readily available (e.g. "Protective Groups in Organic Synthesis" by T. W. Greene). The compound $R'L$ is an electrophile chosen so as to produce substitution in compound 11 that is consistent with Formula I. In some cases $R'$ in 11 may be further modified by a chemical transformation. Examples include but are not limited to hydrolysis of ester or cyano groups in $R'$. Suitable conditions for carrying out the transformations in Scheme 3 are exemplified in Example 3. Those skilled in the art will realize that alternate synthetic methods may be employed to accomplish the reactions in Scheme 3.

Those having skill in the art will recognize that the starting materials may be varied and additional steps

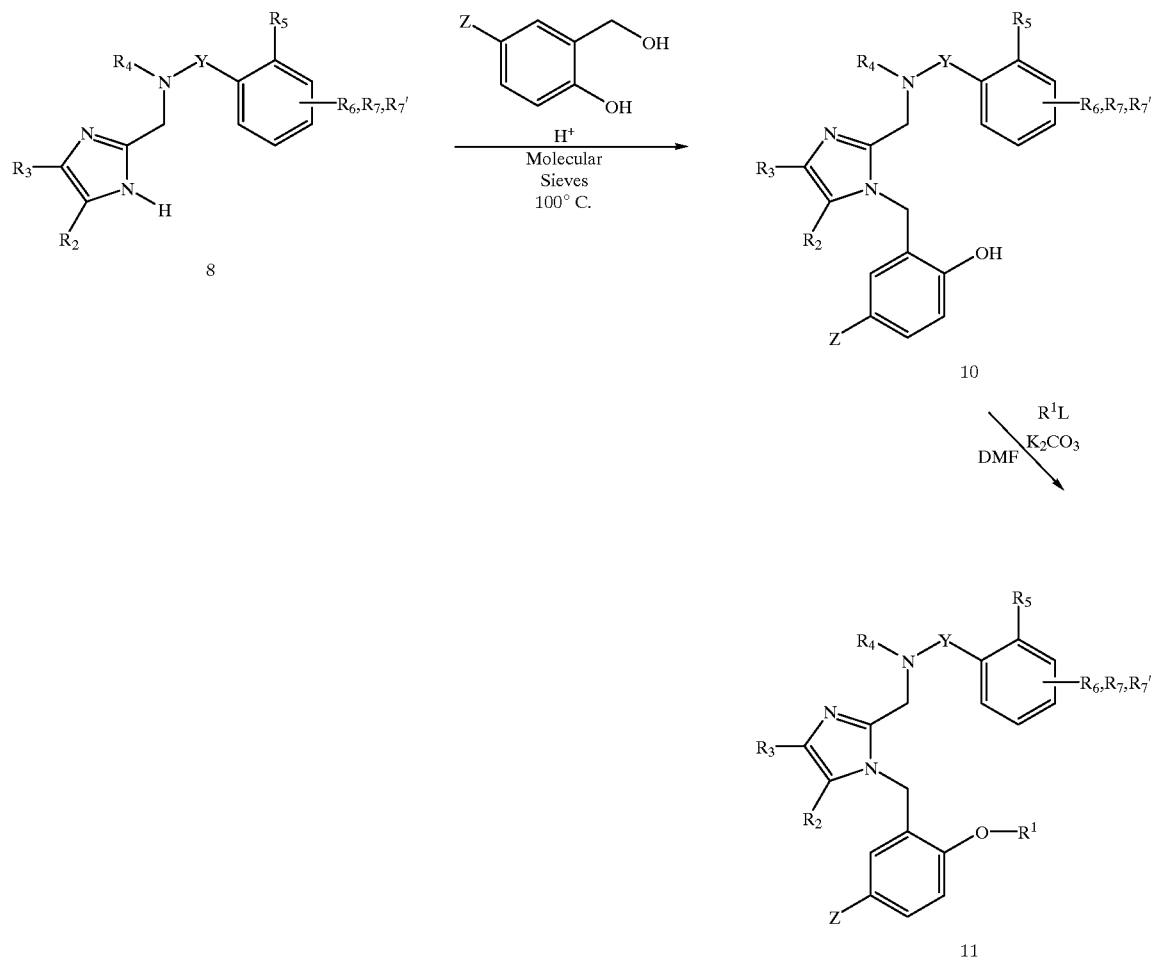

Scheme 3

In Scheme 3, Z represents hydrogen, bromine, chorine or other substituents consistent with the definition of $R_1$ in Formula I. The groups $R_1$, $R_2$, $R_3$, $R_4$, $R_5$, $R_6$, $R_7$, $R_7'$ and Y are as defined as Formula I. Alternatively, appropriately protected forms of $R_1$, $R_2$, $R_3$, $R_4$, $R_5$, $R_6$, $R_7$ and $R_7'$ may be employed. In such cases, an additional deprotection step is employed to obtain the final product. Suitable protecting employed to produce compounds encompassed by the present invention, as demonstrated by the following examples.

The following examples illustrate the general procedures for the preparation of compounds of the invention using the reactions outlined above in Schemes 1–3. These examples are not to be construed as limiting the invention in scope or spirit to the specific procedures and compounds described in them.

Example 1

General Procedure for the Preparation of Substituted Imidazoles as Outlined in Scheme 1

Preparation of (2-Chloro-3,4-dimethoxyphenyl)-N-({1-[(2-chlorophenyl)methyl]-4,5-dimethylimidazol-2-yl}methyl)-N-(3-methylbutyl)carboxamide

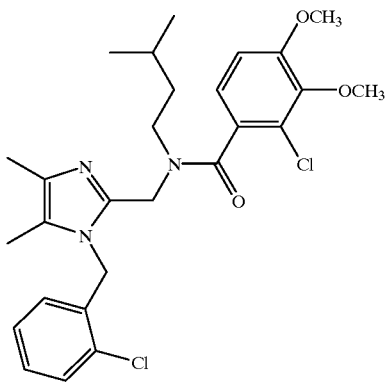

To a solution of 4.89 g (0.027 mol) of 4,5-dimethylimidazole hydrobromide and 5.7 g (0.028 mol) of 2-chlorobenzyl bromide in 20 ml of DMF is added 6 ml of 50% potassium hydroxide aqueous solution dropwise. Then the reaction mixture is stirred at RT under nitrogen overnight. The reaction mixture is poured into ether (100 ml)/water (50 ml). The ether layer is separated, washed with water (10 ml×2), dried over anhydrous sodium sulfate and evaporated in vacuo. The raw material is subjected to chromatography on silica gel using dichloromethane-methanol (10:1) as eluent to give 2.67 g (44%) of 1-(2'-chlorobenzyl)-4,5-dimethylimidazole as a pale yellow oil. MS m/z (M$^+$+1) 221; $^1$H-NMR 400 MHz($\delta$, CDCl$_3$): 2.00 (3H, s), 2.20 (3H, s), 5.07 (2H, s), 6.59 (1H, dd, J=9.2, 2 Hz), 7.17 (1H, td, J=8, 1.2 Hz), 7.23 (1H, td, J=8, 1.6 Hz), 7.38 (2H, dd, J=7.2, 1.6 Hz) ppm.

To a solution of 10 ml of glacial acetic acid and 10 ml of 37% formaldehyde is added 2.67 g (0.012 mol) of 1-(2'-chlorobenzyl)-4,5-dimethylimidazole. The mixture is stirred and heated in a sealed tube at 125–130° C. (oil bath temperature) overnight. After cooling, the solvent is evaporated in vacuo. The residue is subjected to chromatography on silica gel using dichloromethane-methanol (10:1) as eluent to give 2.39 g (79%) of 1-(2'-chlorobenzyl)-4,5-dimethyl-2-hydroxymethylimidazole as colorless powder. MS m/z (M$^+$+1) 251; $^1$H-NMR 400 MHz($\delta$, CDCl$_3$): 1.94 (3H, s), 2.11 (3H, s), 4.53 (2H, s), 5.26 (2H, s), 6.42 (1H, dd, J=8, 1.2 Hz), 7.14(1H, td, J=8, 1.2Hz), 7.21 (1H, td, J=7.4, 1.6 Hz), 7.39 (1H, dd, J=8, 1.2 Hz) ppm.

To 3 ml of thionyl chloride is added 2.39 g (9.5 mmol) of 1-(2'-chlorobenzyl)-4,5-dimethyl-2-hydroxymethyl-imidazole. The mixture is heated at 50° C. for about 5 min., and the thionyl chloride is evaporated in vacuo. The residue is dissolved in 10 ml of dichloromethane, then evaporated in vacuo. This is repeated twice to give 1-(2'-chlorobenzyl)-4,5-dimethyl-2-chloromethylimidazole as a cream colored foam which is used in next step without further purification.

To a solution of 7 ml (60 mmol) of isoamylamine in 3 ml of acetonitrile is added slowly a solution of 1-(2'-chlorobenzyl)-4,5-dimethyl-2-chloromethylimidazole in 10 ml of acetonitrile followed by added 1.5 g (10.8 mmol) of potassium carbonate powder. The reaction mixture is stirred overnight at room temperature under nitrogen and excess isoamylamine is evaporated in vacuo. The residue is dissolved in 50 ml of ethyl acetate and 25 ml of water. The ethyl acetate layer is separated, washed with brine, dried over anhydrous sodium sulfate and evaporated in vacuo. The crude product is purified by preparative TLC [silica gel, chloroform-methanol-ammonium hydroxide (90:10:1)] to give 1.39 g (46%) of N-[(4,5-dimethylimidazol-2-yl)methyl]-(3-methylbutyl)amine as a yellow oil. MS m/z (M$^+$+1) 320; $^1$H-NMR 400 MHz($\delta$, CDCl$_3$): 0.81 (6H, d, J=6.4 Hz), 1.25 (2H, m), 1.51 (1H, m), 1.96 (3H, s), 2.17 (3H, s), 2.56 (2H, m), 3.68 (2H, s), 5.21 (2H, s), 6.39 (1H, d, J=7.6 Hz), 7.13 (1H, m), 7.19 (1H, m), 7.37 (1H, m) ppm.

To a solution of 210 mg (0.66 mmol) of N-[(4,5-dimethylimidazol-2-yl)methyl]-(3-methylbutyl)amine in 5 ml of chloroform (stabilized with amylenes) is added 170 mg (0.84 mmol) of 2-chloro-3,4-dimethoxybenzoyl chloride and 1 ml of triethylamine. The reaction mixture is stirred at RT under nitrogen overnight and evaporated in vacuo. The residue is dissolved in 20 ml of ethyl acetate and 10 ml of water. The ethyl acetate layer is separated, washed with brine (5 ml×2), dried over anhydrous sodium sulfate, and the solvent is evaporated in vacuo. The crude product is purified by preparative TLC [silica gel, chloroform-methanol-ammonia hydroxide (95:4.5:0.5)] to give the title compound as a colorless oil. MS m/z (M$^+$+1) 518; $^1$H-NMR 400 MHz($\delta$, CDCl$_3$): 0.61 and 0.88 (6H, d, J=6 Hz, the ratio of two peaks is 4/1), 1.26 (2H, m), 1.36 (1H, m), 1.89 and 1.94 (3H, s, the ratio of two peaks is 1/4), 2.14 and 2.17 (3H, s, the ratio of two peaks is 1/4), 3.04 (2H, br), 3.74 and 3.80 (3H, s, the ratio of two peaks is 1/4), 3.78 and 3.82 (3H, s, the ratio of two peaks is 1/4), 4.72, 4.84, 5.17, 5.47 (4H, 4 br), 6.30 (2H, d, J=8.4 Hz), 6.67 (1H, d, J=8.8 Hz), 7.15 (1H, td, J=7.2, 1.2 Hz), 7.21 (1H. td, J=7.2, 1.2 Hz), 7.38 (1H, dd, J=7.2, 1.2 Hz) ppm.

Example 2

General Procedure for the Preparation of Substituted Imidazoles as Outlined in Scheme 2

Preparation of (2-Chloro-3,4-dimethoxyphenyl)-N-({1-[(2-methoxyphenyl)methyl]-4,5-dimethylimidazol-2-yl}methyl)-N-(3-methylbutyl)carboxamide

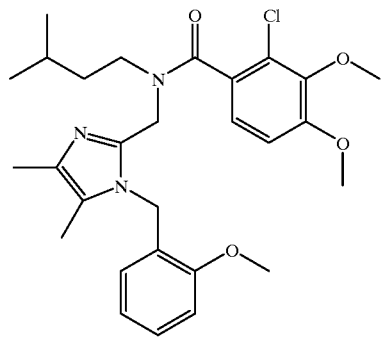

A mixture of 3.35 g (27 mmol) of 4,5-dimethyl-2-imidazolecarboxaldehyde, 9.0 mL (77 mmol) of isoamylamine, 200 mL of ethanol, and 0.20 g of platinum dioxide is hydrogenated under 50 psi of pressure at 22° C. for 24 h. The solution is filtered, and the volatiles are evaporated under reduced pressure to give 5.17 g (98%) of N-[(4,5-dimethylimidazol-2-yl)methyl]-(3-methylbutyl) amine. Mass Spec m/z (M$^+$+1) 196.

A mixture of 4.50 g (20 mmol) of 2-chloro-3,4-dimethoxybenzoic acid, 5 mL of chloroform, 0.2 mL of pyridine, and 5.8 mL (80 mmol) of thionyl chloride is stirred at 40° C. for 1 h. The volatiles are thoroughly evaporated. A solution of the residue in 10 mL of chloroform is added dropwise to a solution of 2.73 g (14 mmol) of N-[(4,5-dimethylimidazol-2-yl)methyl]-3-methylbutylamine in 20 mL of anhydrous pyridine stirred under nitrogen at −20° C. The obtained mixture is allowed to warm up slowly, and it is stirred then at 20° C. for 20 h.

The reaction mixture is poured into 50 mL of water and extracted with 50 mL of chloroform. The extract is washed with 50 mL of 5% NaCO$_3$, and the solvent is evaporated. The residue is dissolved in 20 mL of ethanol, treated with 2 mL of 10N NaOH, and stirred at 60° C. for 1 h. The mixture is poured into 50 mL of 5% NaCO$_3$ and extracted with 50 mL of chloroform. The solvent is evaporated under reduced pressure. The crude product is purified by column chromatography on 100 g of silica gel using chloroform-methanol—28% ammonium hydroxide (95:4.5:0.5, v/v/v) as an eluent to give 2.42 g (44%) of (2-chloro-3,4-dimethoxyphenyl)-N-[(4,5-dimethylimidazol-2-yl)methyl]-N-(3-methylbutyl)carboxamide. Mass Spec m/z (M$^+$+1) 394.

A mixture of 0.74 g (1.9 mmol) of (2-chloro-3,4-dimethoxyphenyl)-N-(3,4-dimethylimidazol-2-yl)methyl-N-(3-methylbutyl)carboxamide, 0.94 g (6.0 mmol) of 2-methoxybenzyl chloride, 10 mL of dimethylformamide and 0.63 mL (8.0 mmol) of 50% KOH is stirred vigorously under nitrogen at 40° C. for 20 h. The reaction mixture is poured into 100 mL of water and extracted with 50 mL of chloroform. The extract is washed with 100 mL of water, and the solvent is evaporated under reduced pressure. The residue is diluted with 50 mL of xylenes, and the volatiles are thoroughly evaporated under reduced pressure. Column chromatography of the residue on 30 g of silica gel using chloroform-diethyl ether (98:2, v/v) as an eluent afforded 646 mg (67%) of the title compound as a cream colored foam. Mass Spec m/z (M++1) 514.

Example 3

General Procedure for the Preparation of Substituted Imidazoles as Outlined in Scheme 3

Preparation of (2-Chloro-3,4-dimethoxyphenyl)-N-({1-[(2-hydroxyphenyl)methyl]4,5-dimethylimidazol-2-yl}methyl)-N-(3-methylbutyl)carboxamido

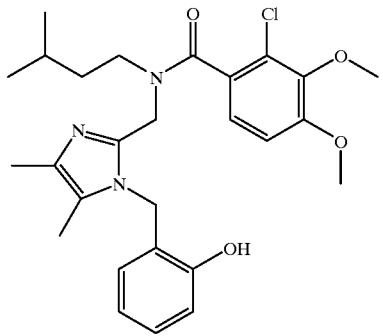

A mixture of 1.89 g (4.8 mmol) of (2-chloro-3,4-dimethoxyphenyl)-N-(3,4-dimethylimidazol-2-yl)methyl-N-(3-methylbutyl)carboxamide, 0.74 g (6.0 mmol) of 2-hydroxybenzyl alcohol, 50 mL of toluene, 0.10 g of p-toluenesulfonic acid monohydrate, and 15 g of molecular sieves 5A is gently stirred and heated under nitrogen at 100° C. for 24 h. Another portion of 2-hydroxybenzyl alcohol (0.37 g, 3.0 mmol) is added, and heating at 100° C. is continued for additional 24 h. The molecular sieves are filtered off and washed with 20 mL of ethyl acetate-methanol (4:1). The filtrate and washings are combined, and the solvent is evaporated under reduced pressure. The crude material is purified by column chromatography on 75 g of silica gel using chloroform-methanol-acetic acid (96:3:1) as an eluent to give 1.74 g (72%) of the title compound. Mass Spec m/z (M$^+$+1) 500.

Preparation of Ethyl {2-[(2-{[(2-chloro-3,4-dimethoxyphenyl)-N-(3-methylbutyl)carbonylamino]methyl}-4,5-dimethylimidazol-1-yl)methyl]phenoxy}acetate

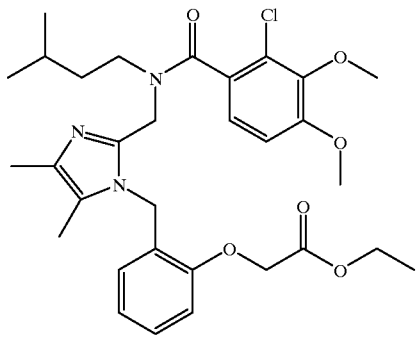

A mixture of 0.55 g (1.1 mmol) of (2-chloro-3,4-dimethoxyphenyl)-N-({1-[(2-hydroxyphenyl)-methyl] 4,5-dimethylimidazol-2-yl}methyl)-N-(3-methylbutyl) carboxamide, 0.24mL (2.2 mmol) of ethyl bromoacetate, 0.69 g (5.0 mmol) of K$_2$CO$_3$, and 5 mL of anhydrous dimethylformamide is stirred under nitrogen at 22° C. for 20 h. The reaction mixture is poured onto 50 g of crushed ice, acidified to pH 6 with 1M HCl, and extracted with hexanes-ethyl acetate (25 mL of each). The extract is washed with water (2×50 mL), dried over MgSO$_4$, and the solvents are evaporated under reduced pressure. The residue is purified by column chromatography on 30 g of silica gel using ethyl acetate as an eluent to give 0.51 g (79%) of the title compound. Mass Spec m/z (M$^+$+1) 586.

Preparation of {2-[(2-{[(2-Chloro-3,4-dimethoxyphenyl)-N-(3-methylbutyl)carbonylamino]methyl}-4,5-dimethylimidazol-1-yl)methyl]phenoxy}acetic acid

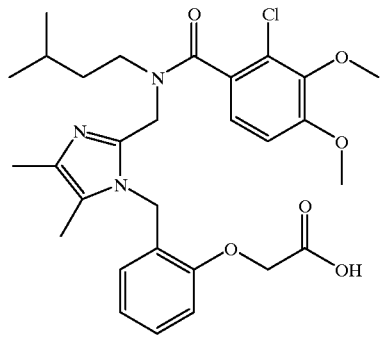

A solution of 58 mg of {2-[(2-{[(2-chloro-3,4-dimethoxyphenyl)-N-(3-methylbutyl)carbonylamino]methyl}-4,5-dimethylimidazol-1-yl)methyl]phenoxy}acetate in 2 mL of 5N HCl is heated under reflux for 15 min. The volatiles are evaporated under reduced pressure, and the residue is dried in a vacuum oven at 90° C. to give 59 mg of the title compound as the hydrochloride salt. Mass Spec m/z (M⁺+1) 558.

Example 4

Alternate Alkylation Conditions for Substituted Imidazoles Prepared in Scheme 2

Preparation of (2-Chloro-3,4-dimethoxyphenyl )-N-({1-[(2-cyanophenyl)methyl] 4,5-dimethylimidazol-2-yl}methyl)-N-(3-methylbutyl)carboxamido

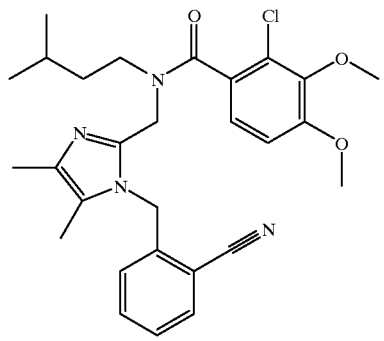

A mixture of 197 mg (0.50 mmol) of (2-chloro-3,4-dimethoxyphenyl)-N-(3,4-dimethylimidazol-2-yl)methyl-N-(3-methylbutyl)carboxamide, 147 mg (0.75 mmol) of α-bromo-o-tolunitrile, 3 mL of DMF, and 415 mg (3 mmol) of K₂CO₃ is stirred under nitrogen at 22° C. for 24 h. The reaction mixture is poured into 30 mL of water and extracted with 30 mL of diethyl ether. The extract is washed with water (2×20 mL), and the solvent is evaporated. The residue is dissolved in 20 mL of xylenes, and the volatiles are thoroughly evaporated in vacuo. The crude product is purified by column chromatography on 24 g of silica gel using chloroform-diethyl ether (85:15) as an eluent to give 181 mg (71% yield) of the title compound. Mass Spec m/z (M⁺+1) 509.

Example 5

Preparation of 2-{2-{[(2-Chloro-3,4-dimethoxyphenyl)-N-(3-methylbutyl)carbonylamino}methyl]-4,5-dimethylimidazol-1-yl)methyl}benzoic acid

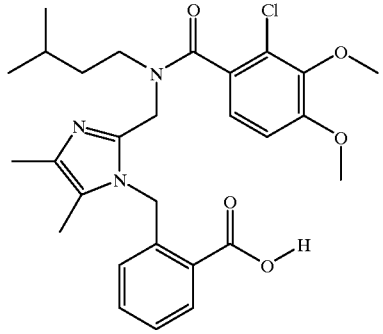

A mixture of 140 mg (0.27 mmol) of (2-Chloro-3,4-dimethoxyphenyl)-N-({1-[(2-cyanophenyl)methyl] 4,5-dimethylimidazol-2-yl}methyl)-N-(3-methylbutyl)carboxamide, 2.0 mL of ethanol and 1.0 mL of 50% KOH is stirred under nitrogen at 80° C. for 18 h. The reaction mixture is poured into 30 g of ice-water, acidified to pH 5 with 1M HCl, and extracted with 20 mL of ethyl acetate. The extract is washed with 10 mL of water, and the solvent is evaporated under reduced pressure. The residue is triturated with 2 mL of acetone, and the crystals are separated by decantation to give 112 mg (78%) of the title compound. Mass Spec m/z (M⁺+1) 528.

Example 6

Preparation of (2-Chloro-3,4-dimethoxyphenyl)-N-({1-[(2-[cyanomethoxyl]-phenyl)methyl]4,5-dimethylimidazol-2-yl}methyl)-N-(3-methylbutyl)carboxamide.

A mixture of 250 mg (0.50 mmol) of (2-chloro-3,4-dimethoxyphenyl)-N-(4,5-dimethylimidazol-2-yl)methyl-N-(3-methylbutyl)carboxamide, 52 μL of chloroacetonitrile (0.75 mmol), 276 mg (2.0 mmol) of K₂CO₃, and 3 mL of anhydrous DMF is stirred under nitrogen at 22° C. for 24 h and poured into 10% NaCl. The mixture is extracted with 20 mL of ethyl acetate. The extract is concentrated under reduced pressure, diluted with 20 mL of xylenes, and the volatiles are thoroughly evaporated. The crude product is purified by chromatography on 30 g of silica gel using chloroform—methanol—28% ammonium hydroxide (98:1.8:0.2, v/v/v) for elution to afford 113 mg (42% yield) of the title compound. Mass Spec m/z (M⁺+1) 539.

Using the above procedures, the following compounds were prepared according to Schemes 1, 2 and 3:

(a) (2-Chloro-3,4-dimethoxyphenyl)-N-{[1-benzyl-4,5-dimethylimidazol-2-yl]methyl}-N-(3-methylbutyl) carboxamide. Mass Spec m/z (M$^+$+1) 484.

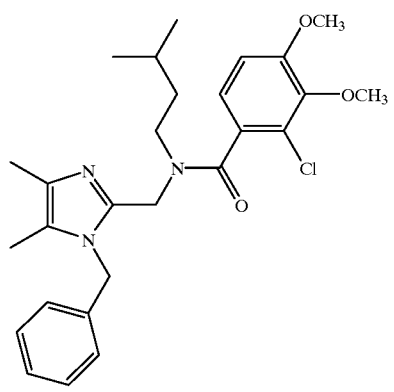

(b) (2-Chloro-3,4-dimethoxyphenyl-N-({4,5-dimethyl-1-[(2-methylphenyl)methyl]}imidazol-2-yl}methyl-N-(3-methylbutyl)carboxamide. Mass Spec m/z (M$^+$+1) 498.

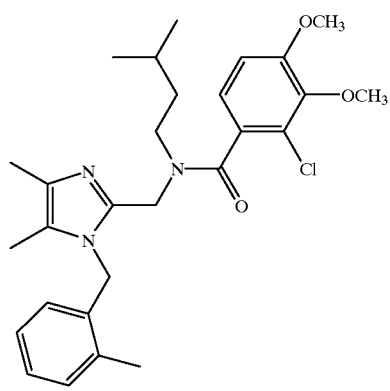

(c) (2-Chloro-3,4-dimethoxyphenyl-N-[(4,5-dimethyl-1-{[2-(trifluoromethyl)phenyl]methyl}imidazol-2-yl)methyl]-N-(3-methylbutyl)carboxamide. Mass Spec m/z (M$^+$+1) 552.

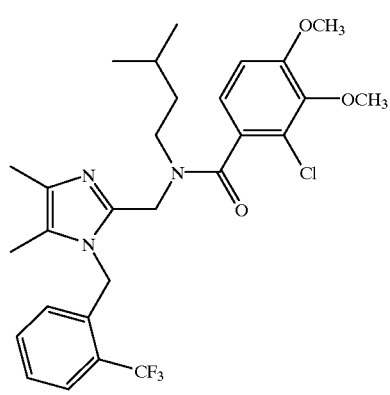

(d) N-{[4,5-Dichloro-1-benzylimidazol-2-yl]methyl}(2-chloro-3,4-dimethoxyphenyl)-N-(3-methylbutyl) carboxamide. Mass Spec m/z (M$^+$+1) 524.

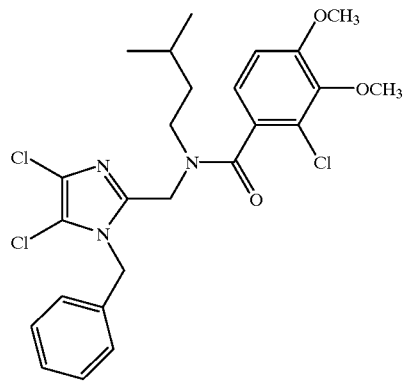

(e) N-({4,5-Dichloro-1-[(2-chlorophenyl)methyl]imidazol-2-yl}methyl)(2-chloro-3,4-dimethoxyphenyl)-N-(3-methylbutyl)carboxamide. Mass Spec m/z (M$^+$+1) 560.

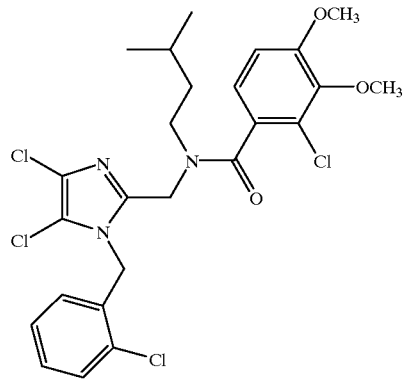

(f) N-({4,5-Dichloro-1-[(2-methylphenyl)methyl]imidazol-2-yl}methyl)(2-chloro-3,4-dimethoxyphenyl)-N-(3-methylbutyl)carboxamide. Mass Spec m/z (M$^+$+1) 540.

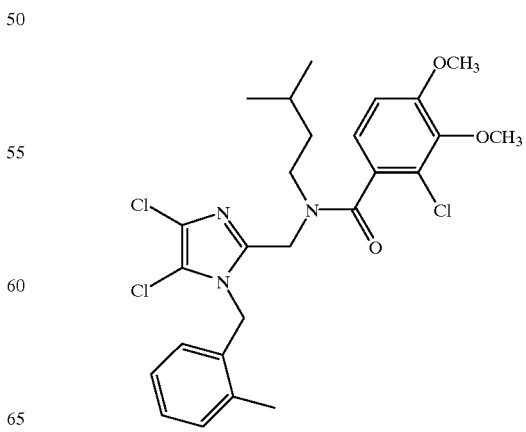

(g) (2-Chloro-3,4-dimethoxyphenyl)-N-{3,4-diethyl-1-[(pyridin-2-yl)methyl]imidazol-2-yl}methyl-N(3-methylbutyl) carboxamide. Mass Spec m/z (M$^+$+1) 513.

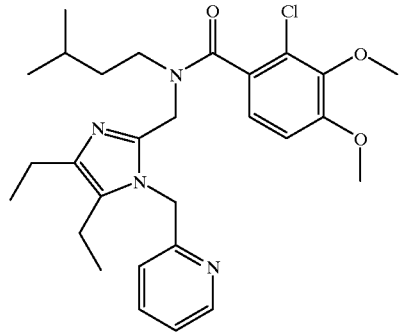

(h) 2-Chloro-3,4-dimethoxyphenyl)-N-{3,4-dimethyl-1-[quinolin-2-yl)methyl]imidazol-2-yl}methyl-N-(3-methylbutyl)carboxamide. Mass Spec m/z (M$^+$+1) 535.

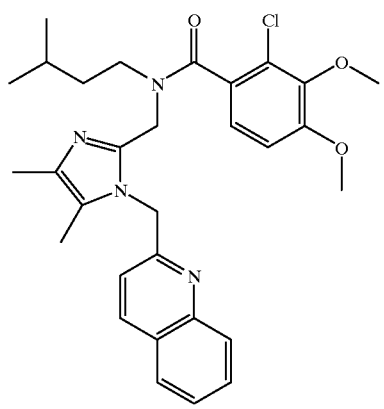

(i) (2-Chloro-3,4-dimethoxyphenyl)-N-{4,5-diethyl-1-[(5-ethyl-2-methoxyphenyl)methyl]imidazol-2-yl}methyl-N-(3-methylbutyl)carboxamide. Mass Spec m/z(M$^+$+1)570.

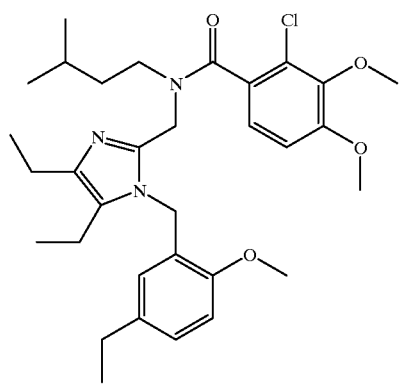

(j) (2-Chloro-3,4-dimethoxyphenyl)-N-({1-[(5-bromo-2-hydzoxyphenyl)methyl]4,5-dimethylimidazol-2-yl}methyl-N-(3-methylbutyl) carboxamide. Mass Spec m/z (M$^{30}$+1) 579.

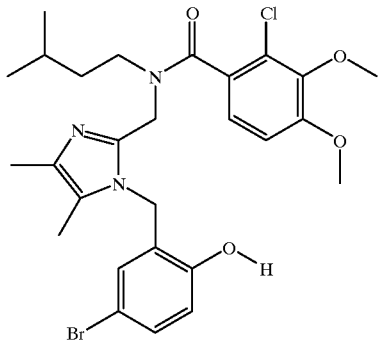

(k) (2-Chloro-3,4-dimethoxyphenyl)-N-{3,4-dimethyl-1-[(5-chloro-2-hydroxyphenyl)methyl]imidazol-2-yl}methyl-N-(3-methylbutyl) carboxamide. Mass Spec m/z (M$^+$+1) 534.

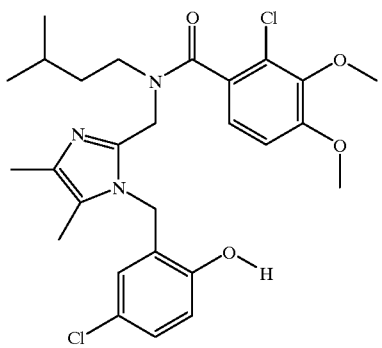

(l) (2-Chloro-3,4-dimethoxyphenyl)-N-({3-[(2-chlorophenyl)methyl](3,4,5,6,7-pentahydrobenzimidazol-2-yl)}methyl)-N-(3-methylbutyl)carboxamide. Mass Spec m/z (M$^+$+1) 544.

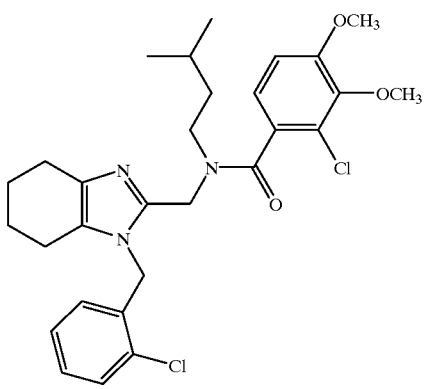

Example 7
Additional Compounds of the Invention

Additional Compounds of the invention which may be prepared by the methods outlined in Reaction Schemes 1, 2, and 3 are shown in Table I.

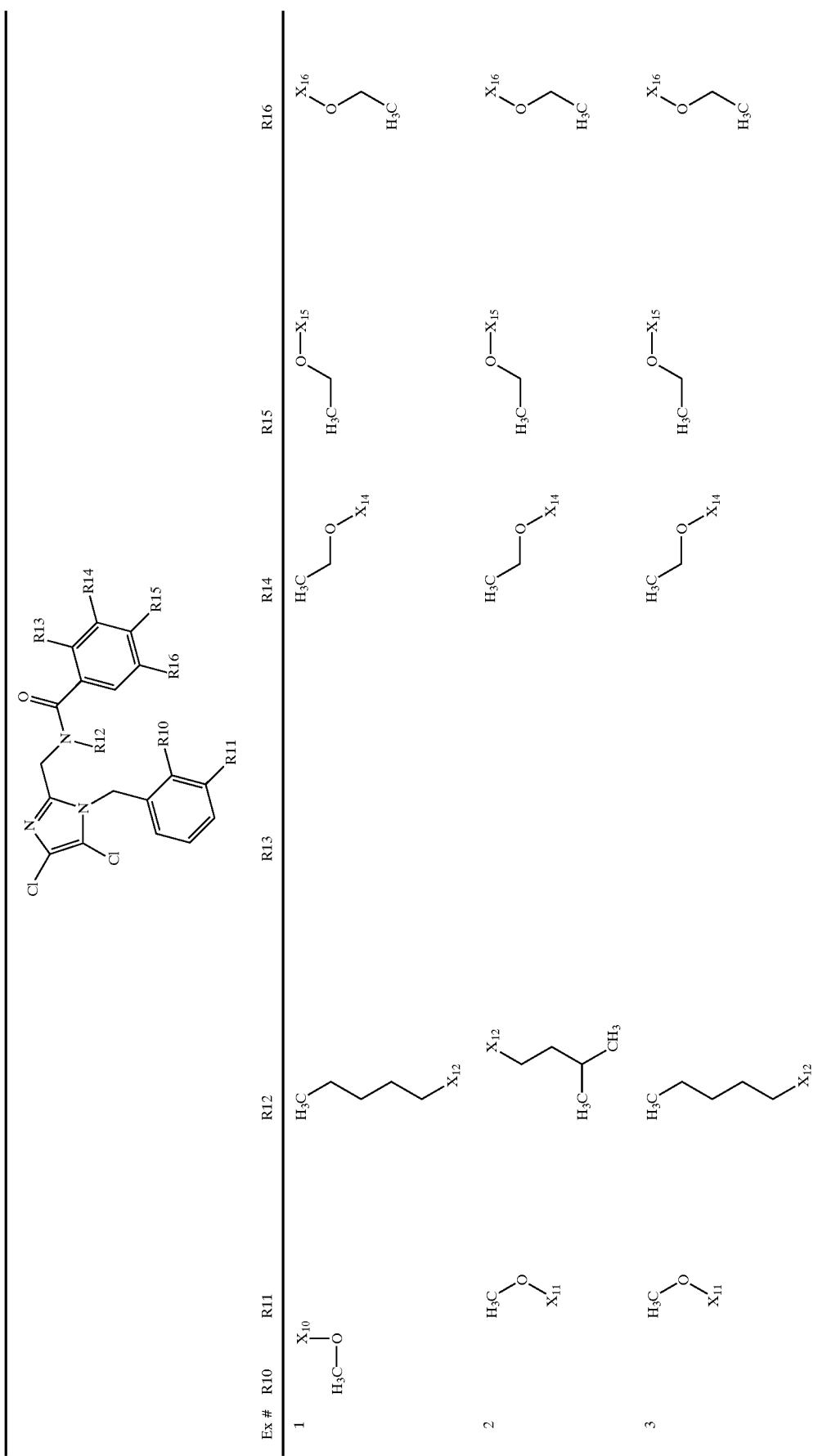
| Ex # | R10 | R11 | R12 | R13 | R14 | R15 | R16 |
|---|---|---|---|---|---|---|---|
| 1 | X₁₀—O—CH₃ | | H₃C—(CH₂)₄—X₁₂ | | H₃C—O—X₁₄ | H₃C—O—X₁₅ | X₁₆—O—CH₃ |
| 2 | | H₃C—O—X₁₁ | X₁₂—CH₂CH₂—CH(CH₃)—CH₃ | | H₃C—O—X₁₄ | H₃C—O—X₁₅ | X₁₆—O—CH₃ |
| 3 | | H₃C—O—X₁₁ | H₃C—(CH₂)₄—X₁₂ | | H₃C—O—X₁₄ | H₃C—O—X₁₅ | X₁₆—O—CH₃ |

-continued
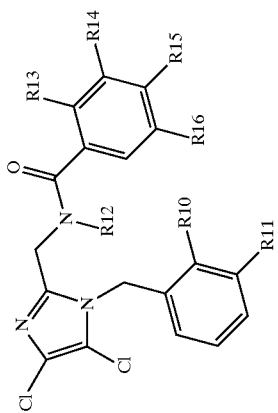
| Ex # | R10 | R11 | R12 | R13 | R14 | R15 | R16 |
|---|---|---|---|---|---|---|---|
| 4 | X₁₀—O—CH₃ | | X₁₂CH₂CH₂CH(CH₃)₂ (H₃C, CH₃) | | H₃C—O—X₁₄ | H₃C—O—X₁₅ | X₁₆—CF₃ |
| 5 | X₁₀—O—CH₃ | | H₃C(CH₂)₄—X₁₂ | | F₃C—X₁₄ | | X₁₆—CF₃ |
| 6 | | H₃C—O—X₁₁ | X₁₂CH₂CH₂CH(CH₃)₂ (H₃C, CH₃) | | F₃C—X₁₄ | | X₁₆—CF₃ |

-continued
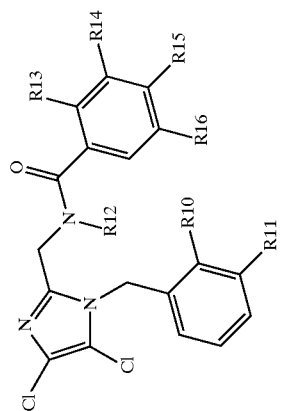
| Ex # | R10 | R11 | R12 | R13 | R14 | R15 | R16 |
|---|---|---|---|---|---|---|---|
| 7 | | H₃C–O–X₁₁ | H₃C~~~X₁₂ | | F₃C–X₁₄ | | F₃C–X₁₆ |
| 8 | X₁₀–O–CH₃ | | X₁₂–CH(CH₃)–CH₂CH₂– | | F₃C–X₁₄ | | F₃C–X₁₆ |
| 9 | X₁₀–O–CH₃ | | H₃C~~~X₁₂ | | I–X₁₄ | H₃C–X₁₅ | |

-continued
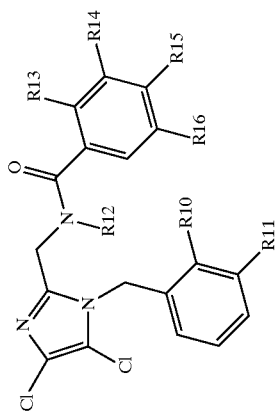
| Ex # | R10 | R11 | R12 | R13 | R14 | R15 | R16 |
|---|---|---|---|---|---|---|---|
| 10 | | H3C—O—X11 | X12—CH(CH3)—CH2—CH2 with H3C | | I—X14 | H3C—X15 | |
| 11 | | H3C—O—X11 | H3C—CH2CH2CH2CH2—X12 | | I—X14 | H3C—X15 | |
| 12 | X10—O—CH3 | | X12—CH(CH3)—CH2—CH2 with H3C | | I—X14 | H3C—X15 | |

-continued
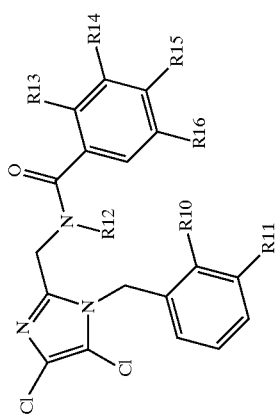
| Ex # | R10 | R11 | R12 | R13 | R14 | R15 | R16 |
|---|---|---|---|---|---|---|---|
| 13 | H3C—O—X10 | | H3C~~~~~X12 | | | | O—X15, H3C~~~~~~ |
| 14 | | H3C—O—X11 | X12~~CH(CH3)~~CH3 | | | | O—X15, H3C~~~~~~ |
| 15 | | H3C—O—X11 | H3C~~~~X12 | | | | O—X15, H3C~~~~~~ |

-continued
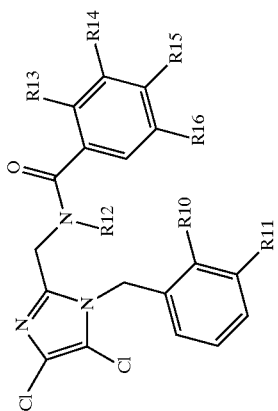
| Ex # | R10 | R11 | R12 | R13 | R14 | R15 | R16 |
|---|---|---|---|---|---|---|---|
| 16 | X₁₀—O—CH₃ | | X₁₂—CH₂CH₂—CH(CH₃)—CH₃ (H₃C at branch) | | | CH₃(CH₂)₇—O—X₁₅ | |
| 17 | X₁₀—O—H (H₃C) | | H₃C(CH₂)₄—X₁₂ | | | CH₃(CH₂)₇—O—X₁₅ | |
| 18 | | H₃C—O—X₁₁ | X₁₂—CH₂CH₂—CH(CH₃)—CH₃ | | | CH₃(CH₂)₇—O—X₁₅ | |

-continued

| Ex # | R10 | R11 | R12 | R13 | R14 | R15 | R16 |
|---|---|---|---|---|---|---|---|
| 19 | | H₃C−O−X₁₁ | H₃C∼∼X₁₂ | | | H₃C∼∼∼∼∼O−X₁₅ | |
| 20 | X₁₀−O−CH₃ | | X₁₂∼CH(CH₃)∼ | X₁₃−Cl | | H₃C∼∼∼∼∼O−X₁₅ | |
| 21 | X₁₀−O−CH₃ | | H₃C∼∼X₁₂ | | | | CH₃−S−X₁₆ |

-continued
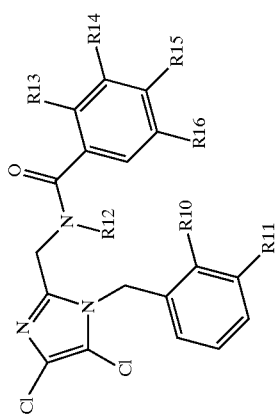
| Ex # | R10 | R11 | R12 | R13 | R14 | R15 | R16 |
|---|---|---|---|---|---|---|---|
| 22 |  | H3C-O-X11 | X12-CH2CH2-CH(CH3)-CH3 | X13-Cl |  |  | X16-S-CH3 |
| 23 |  | H3C-O-X11 | H3C-CH2CH2CH2CH2-X12 | X13-Cl |  |  | CH3-S-X16 |
| 24 | X10-O-CH3 |  | X12-CH2CH2-CH(CH3)-CH3 | X13-Cl |  |  | X16-S-CH3 |

-continued
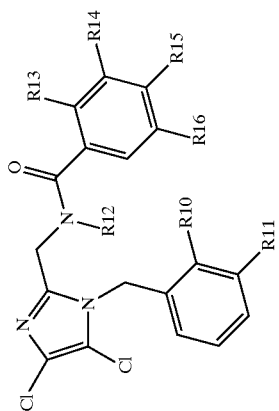
| Ex # | R10 | R11 | R12 | R13 | R14 | R15 | R16 |
|---|---|---|---|---|---|---|---|
| 25 | H3C-O-X10 | | H3C-CH2CH2CH2CH2-X12 | X13-Br | | | H3C-X16 |
| 26 | | H3C-O-X11 | X12-CH2CH2-CH(CH3)-CH3 | X13-Br | | | H3C-X16 |
| 27 | | H3C-O-X11 | H3C-CH2CH2CH2CH2-X12 | X13-Br | | | H3C-X16 |

-continued

[Structure: benzamide with R13, R14, R15, R16 on benzene ring; N-R12; CH2 linker to imidazole with two Cl substituents; N-CH2-phenyl with R10, R11]

| Ex # | R10 | R11 | R12 | R13 | R14 | R15 | R16 |
|---|---|---|---|---|---|---|---|
| 28 | X₁₀—O—CH₃ | | X₁₂—CH₂—CH₂—CH(CH₃)—CH₃ | Br—X₁₃ | | | H₃C—X₁₆ |
| 29 | | X₁₀—O—CH₃ | H₃C—(CH₂)₄—X₁₂ | X₁₃—Cl | | H₃C—O—X₁₅ | CH₃—O—X₁₆ |
| 30 | | H₃C—O—X₁₁ | X₁₂—CH₂—CH₂—CH(CH₃)—CH₃ | X₁₃—Cl | | H₃C—O—X₁₅ | X₁₆—O—CH₃ |

-continued
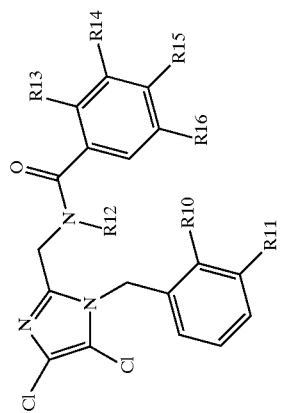
| Ex # | R10 | R11 | R12 | R13 | R14 | R15 | R16 |
|---|---|---|---|---|---|---|---|
| 31 | H₃C−O−X₁₁ | | H₃C−−−−−X₁₂ | X₁₃−Cl | | H₃C−O−X₁₅ | CH₃−O−X₁₆ |
| 32 | X₁₀−O−CH₃ | | X₁₂−−−CH(CH₃)−−−CH₃ | X₁₃−Cl | | H₃C−O−X₁₅ | X₁₆−O−CH₃ |
| 33 | X₁₀−O−CH₃ | | H₃C−−−−−X₁₂ | X₁₃−Br | H₃C−X₁₄ | | |

-continued
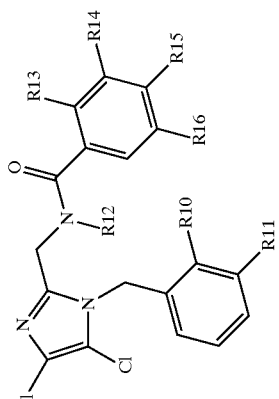
| Ex # | R10 | R11 | R12 | R13 | R14 | R15 | R16 |
|---|---|---|---|---|---|---|---|
| 34 | | H₃C-O-X₁₁ | X₁₂-CH(CH₃)-CH₂-CH₂ (H₃C-CH(X₁₂)...) | X₁₃-Br | H₃C-X₁₄ | | |
| 35 | | H₃C-O-X₁₁ | H₃C-CH₂-CH₂-CH₂-CH₂-X₁₂ | X₁₃-Br | H₃C-X₁₄ | | |
| 36 | X₁₀-O-CH₃ | | X₁₂-CH₂-CH₂-CH(CH₃)-CH₃ | X₁₃-Br | H₃C-X₁₄ | | |

-continued
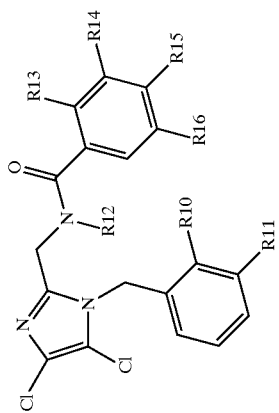
| Ex # | R10 | R11 | R12 | R13 | R14 | R15 | R16 |
|---|---|---|---|---|---|---|---|
| 37 | $X_{10}$—O—$CH_3$ | | $H_3C$—$\underset{}{\phantom{x}}$—$X_{12}$ (pentyl) | $X_{13}$—Cl | $X_{14}$—$CF_3$ | | |
| 38 | | $H_3C$—O—$X_{11}$ | $X_{12}$—$CH_2CH_2$—CH($CH_3$)— (with $CH_3$) | $X_{13}$—Cl | $X_{14}$—$CF_3$ | | |
| 39 | | $H_3C$—O—$X_{11}$ | $H_3C$—$\underset{}{\phantom{x}}$—$X_{12}$ (pentyl) | $X_{13}$—Cl | $X_{14}$—$CF_3$ | | |

-continued

| Ex # | R10 | R11 | R12 | R13 | R14 | R15 | R16 |
|---|---|---|---|---|---|---|---|
| 40 | X₁₀–O–CH₃ | | X₁₂–CH₂–CH₂–CH(CH₃)–CH₃ | X₁₃–Cl | F₃C–X₁₄ | | F₃C–X₁₆ |
| 41 | X₁₀–O–CH₃ | | H₃C–CH₂–CH₂–CH₂–CH₂–X₁₂ | X₁₃–Cl | | | F₃C–X₁₆ |
| 42 | | H₃C–O–X₁₁ | X₁₂–CH₂–CH₂–CH(CH₃)–CH₃ | X₁₃–Cl | | | |

-continued
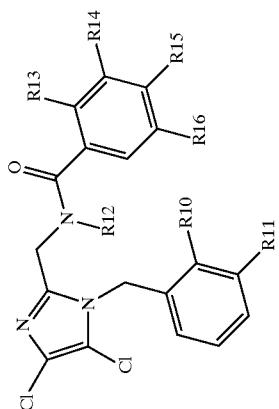
| Ex # | R10 | R11 | R12 | R13 | R14 | R15 | R16 |
|---|---|---|---|---|---|---|---|
| 43 | | H₃C–O–X₁₁ | H₃C–(CH₂)₄–X₁₂ | X₁₃–Cl | | | CF₃–X₁₆ |
| 44 | X₁₀–O–CH₃ | | X₁₂–CH₂CH₂–CH(CH₃)–CH₃ | X₁₃–Cl | | | CF₃–X₁₆ |
| 45 | X₁₀–O–CH₃ | H₃C–O–X₁₁ | H₃C–(CH₂)₄–X₁₂ | X₁₃–Br | | H₃C–O–X₁₅ | CH₃–O–X₁₆ |

-continued
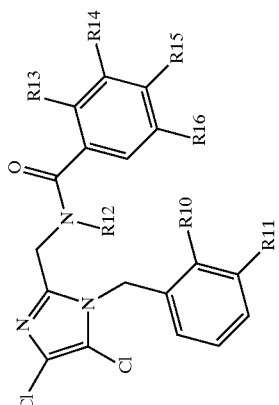
| Ex # | R10 | R11 | R12 | R13 | R14 | R15 | R16 |
|---|---|---|---|---|---|---|---|
| 46 | | H₃C-O-X₁₁ | X₁₂-CH₂CH₂-CH(CH₃)- | X₁₃-Br | | H₃C-O-X₁₅ | X₁₆-O-CH₃ |
| 47 | | H₃C-O-X₁₁ | H₃C-(CH₂)₄-X₁₂ | X₁₃-Br | | H₃C-O-X₁₅ | CH₃-O-X₁₆ |
| 48 | X₁₀-O-CH₃ | | X₁₂-CH₂CH₂-CH(CH₃)- | X₁₃-Br | | H₃C-O-X₁₅ | X₁₆-O-CH₃ |
| 49 | X₁₀-O-CH₃ | | H₃C-(CH₂)₄-X₁₂ | H₃C-S-X₁₃ | | H₃C-O-X₁₅ | X₁₆-O-CH₃ |

-continued
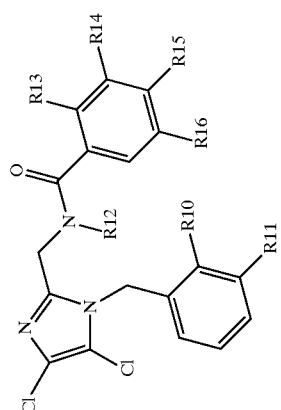
| Ex # | R10 | R11 | R12 | R13 | R14 | R15 | R16 |
|---|---|---|---|---|---|---|---|
| 50 |  | H₃C−O−X₁₁ | X₁₂−CH(CH₃)−CH₂−CH₂ (with CH₃) | H₃C−S−X₁₃ |  |  |  |
| 51 |  |  | H₃C−CH₂−CH₂−CH₂−X₁₂ | H₃C−S−X₁₃ |  |  |  |
| 52 | X₁₀−O−CH₃ | H₃C−O−X₁₁ | X₁₂−CH₂−CH₂−CH(CH₃) (with CH₃) | H₃C−S−X₁₃ |  |  |  |

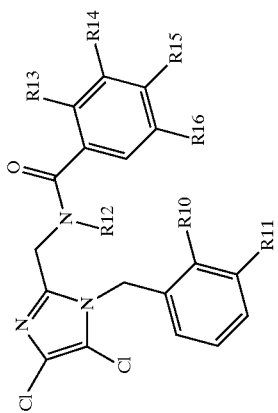
| Ex # | R10 | R11 | R12 | R13 | R14 | R15 | R16 |
|---|---|---|---|---|---|---|---|
| 53 | H₃C—O—X₁₀ | | H₃C~~~~~X₁₂ | | | | |
| 54 | | H₃C—O—X₁₁ | X₁₂~CH(CH₃)~~ | | | | |
| 55 | | H₃C—O—X₁₁ | H₃C~~~~~X₁₂ | | | | |

| Ex # | R10 | R11 | R12 | R13 | R14 | R15 | R16 |
|---|---|---|---|---|---|---|---|
| 56 | X₁₀–O–CH₃ | | X₁₂–CH₂–CH₂–CH(CH₃)–CH₃ | | H₃C–X₁₄ | | |
| 57 | X₁₀–O–CH₃ | | H₃C–CH₂–CH₂–CH₂–CH₂–X₁₂ | | | | |
| 58 | X₁₀–O–CH₃ | H₃C–O–X₁₁ | X₁₂–CH₂–CH₂–CH(CH₃)–CH₃ | | H₃C–X₁₄ | | |

-continued
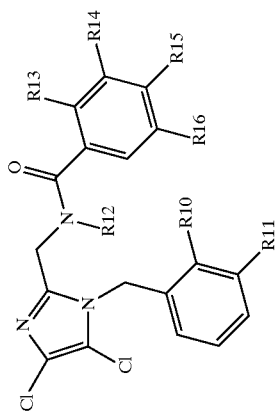
| Ex # | R10 | R11 | R12 | R13 | R14 | R15 | R16 |
|---|---|---|---|---|---|---|---|
| 59 | | H₃C–O–X₁₁ | H₃C~~~X₁₂ | | H₃C–X₁₄ | | |
| 60 | X₁₀–O–CH₃ | | X₁₂–CH₂CH₂–CH(CH₃)– | | H₃C–X₁₄ | | |
| 61 | X₁₀–O–CH₃ | | H₃C~~~X₁₂ | | | H₃C–X₁₅ | |

-continued
| Ex # | R10 | R11 | R12 | R13 | R14 | R15 | R16 |
|---|---|---|---|---|---|---|---|
| 62 | | H₃C—O—X₁₁ | X₁₂–CH₂–CH₂–CH(CH₃)–CH₃ | | | H₃C—X₁₅ | |
| 63 | | H₃C—O—X₁₁ | H₃C–CH₂–CH₂–CH₂–CH₂–X₁₂ | | | H₃C—X₁₅ | |
| 64 | X₁₀–O–CH₃ | | X₁₂–CH₂–CH₂–CH(CH₃)–CH₃ | | | H₃C—X₁₅ | |
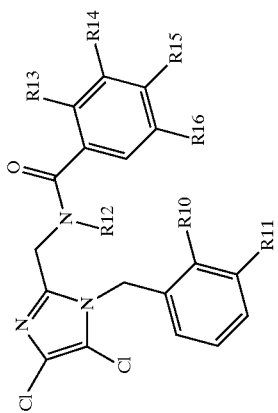

-continued
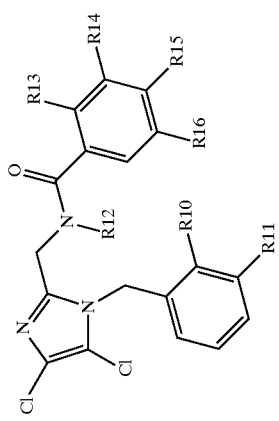
| Ex # | R10 | R11 | R12 | R13 | R14 | R15 | R16 |
|---|---|---|---|---|---|---|---|
| 65 | H3C—O—X10 | | H3C—(CH2)4—X12 | X13—CH3 | | | |
| 66 | | H3C—O—X11 | X12—CH2CH2—CH(CH3) | X13—CH3 | | | |
| 67 | | H3C—O—X11 | H3C—(CH2)4—X12 | X13—CH3 | | | |

-continued

| Ex # | R10 | R11 | R12 | R13 | R14 | R15 | R16 |
|------|-----|-----|-----|-----|-----|-----|-----|
| 68 | $X_{10}$—O—CH$_3$ | | $X_{12}$—CH$_2$—CH$_2$—CH(CH$_3$)$_2$ | $X_{13}$—CH$_3$ | | | |
| 69 | $X_{10}$—O—CH$_3$ | | H$_3$C—(CH$_2$)$_4$—$X_{12}$ | | | | |
| 70 | | H$_3$C—O—$X_{11}$ | $X_{12}$—CH$_2$—CH$_2$—CH(CH$_3$)$_2$ | | F—$X_{14}$ | | |

-continued
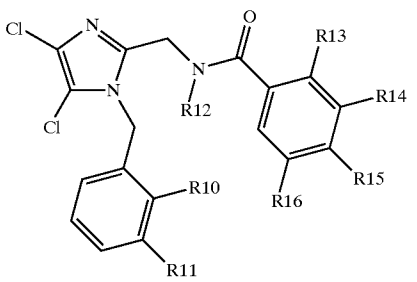
| Ex # | R10 | R11 | R12 | R13 | R14 | R15 | R16 |
|---|---|---|---|---|---|---|---|
| 71 | |  | H₃C—(CH₂)₄—X₁₂ | | F—X₁₄ | | |
| 72 | X₁₀—O—CH₃ | | X₁₂—CH₂CH₂—CH(CH₃)— with H₃C | | F—X₁₄ | | |
| 73 | 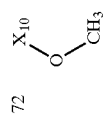 | | H₃C—(CH₂)₄—X₁₂ | | | F—X₁₅ | |

-continued
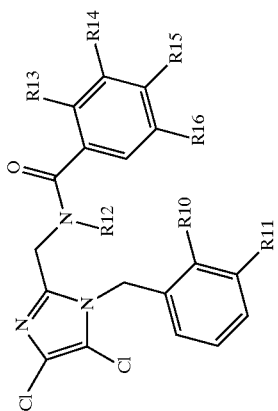
| Ex # | R10 | R11 | R12 | R13 | R14 | R15 | R16 |
|---|---|---|---|---|---|---|---|
| 74 | | H3C-O-X11 | X12-CH(CH3)-... H3C | | | F—X15 | |
| 75 | | H3C-O-X11 | H3C-...-X12 | | | F—X15 | |
| 76 | X10-O-CH3 | | X12-CH(CH3)-... H3C | | | F—X15 | |

-continued
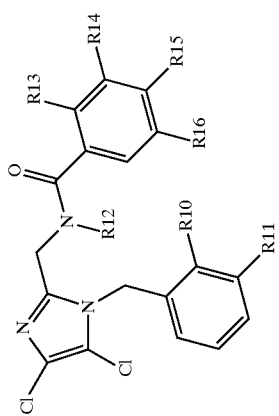
| Ex # | R10 | R11 | R12 | R13 | R14 | R15 | R16 |
|---|---|---|---|---|---|---|---|
| 77 | H3C—O—X10 | | H3C~~~X12 | X13—F | | | |
| 78 | | H3C—O—X11 | X12~~CH(CH3)~~ | X13—F | | | |
| 79 | | H3C—O—X11 | H3C~~~X12 | X13—F | | | |

-continued
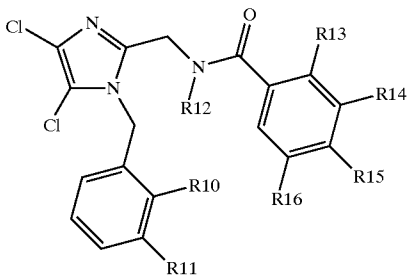
| Ex # | R10 | R11 | R12 | R13 | R14 | R15 | R16 |
|---|---|---|---|---|---|---|---|
| 80 | $X_{10}$—O—$CH_3$ | | $X_{12}$—CH($CH_3$)—... —$CH_3$ | $X_{13}$—F | | $H_3C$—$X_{15}$ | |
| 81 | $X_{10}$—O—$CH_3$ | | $H_3C$—...—$X_{12}$ | | | | |
| 82 | | $H_3C$—O—$X_{11}$ | $X_{12}$—CH($CH_3$)—...—$CH_3$ | | | $H_3C$—$X_{15}$ | |

-continued
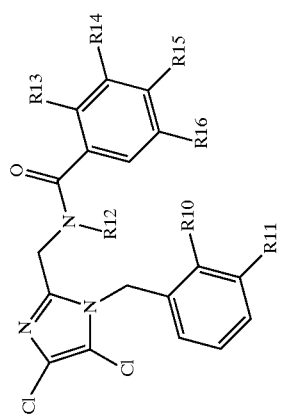
| Ex # | R10 | R11 | R12 | R13 | R14 | R15 | R16 |
|---|---|---|---|---|---|---|---|
| 83 |  | H₃C-O-X₁₁ | H₃C~~~X₁₂ |  |  | H₃C-X₁₅ |  |
| 84 | X₁₀-O-CH₃ |  | X₁₂-CH(CH₃)-CH₂CH₂-... |  |  | H₃C-X₁₅ |  |
| 85 | X₁₀-O-CH₃ |  | H₃C~~~X₁₂ |  | H₃C-X₁₄ | H₃C-X₁₅ |  |

-continued
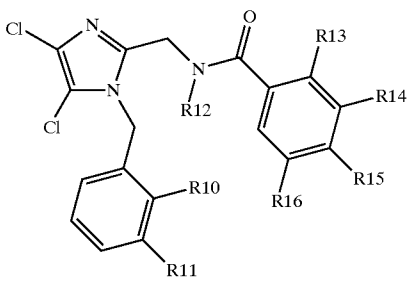
| Ex # | R10 | R11 | R12 | R13 | R14 | R15 | R16 |
|---|---|---|---|---|---|---|---|
| 86 | | H₃C—O—X₁₁ | X₁₂—CH(CH₃)—CH₂—CH₂ (with H₃C) | | H₃C—X₁₄ | H₃C—X₁₅ | |
| 87 | | H₃C—O—X₁₁ | H₃C—(CH₂)₄—X₁₂ | | H₃C—X₁₄ | H₃C—X₁₅ | |
| 88 | X₁₀—O—CH₃ | | X₁₂—CH₂—CH₂—CH(CH₃) (with H₃C) | | H₃C—X₁₄ | H₃C—X₁₅ | |

-continued

[Structure: benzamide with R13, R14, R15, R16 on phenyl ring; N-R12 amide linked to CH2-imidazole (with two Cl substituents) N-substituted with CH2-phenyl bearing R10, R11]

| Ex # | R10 | R11 | R12 | R13 | R14 | R15 | R16 |
|---|---|---|---|---|---|---|---|
| 89 | H$_3$C-O-X$_{10}$ | | H$_3$C-(CH$_2$)$_4$-X$_{12}$ | | H$_3$C-X$_{14}$ | | H$_3$C-X$_{16}$ |
| 90 | | H$_3$C-O-X$_{11}$ | H$_3$C-CH(X$_{12}$)-CH$_2$-CH(CH$_3$)- (isopentyl) | | H$_3$C-X$_{14}$ | | H$_3$C-X$_{16}$ |
| 91 | | H$_3$C-O-X$_{11}$ | H$_3$C-(CH$_2$)$_4$-X$_{12}$ | | H$_3$C-X$_{14}$ | | H$_3$C-X$_{16}$ |

-continued
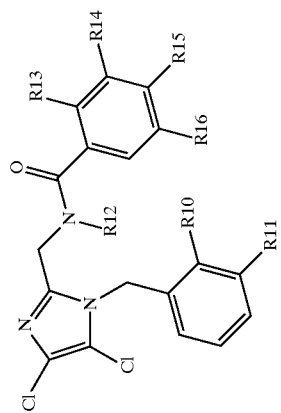
| Ex # | R10 | R11 | R12 | R13 | R14 | R15 | R16 |
|---|---|---|---|---|---|---|---|
| 92 | X$_{10}$-O-CH$_3$ | | X$_{12}$-CH$_2$CH$_2$CH(CH$_3$)$_2$ | | H$_3$C-X$_{14}$ | | H$_3$C-X$_{16}$ |
| 93 | X$_{10}$-O-CH$_3$ | | H$_3$C(CH$_2$)$_4$-X$_{12}$ | X$_{13}$-CH$_3$ | H$_3$C-X$_{14}$ | | |
| 94 | | H$_3$C-O-X$_{11}$ | X$_{12}$-CH$_2$CH$_2$CH(CH$_3$)$_2$ | X$_{13}$-CH$_3$ | H$_3$C-X$_{14}$ | | |

-continued

| Ex # | R10 | R11 | R12 | R13 | R14 | R15 | R16 |
|---|---|---|---|---|---|---|---|
| 95 | | H₃C–O–X₁₁ | H₃C–––––X₁₂ | X₁₃–CH₃ | H₃C–X₁₄ | | |
| 96 | X₁₀–O–CH₃ | | X₁₂–CH(CH₃)–CH₂–CH₃ | X₁₃–CH₃ | H₃C–X₁₄ | | |
| 97 | X₁₀–O–CH₃ | | H₃C–––––X₁₂ | X₁₃–CH₃ | | | H₃C–X₁₆ |

-continued
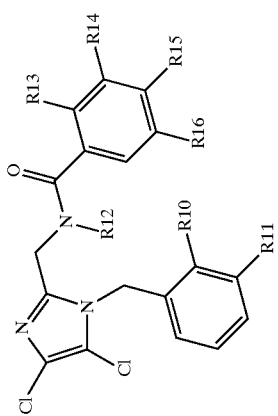
| Ex # | R10 | R11 | R12 | R13 | R14 | R15 | R16 |
|---|---|---|---|---|---|---|---|
| 98 | | H₃C-O-X₁₁ | X₁₂-CH(CH₃)-CH₂-CH₂- (H₃C-CH(CH₃)-CH₂-CH₂-X₁₂) | X₁₃-CH₃ | | | H₃C-X₁₆ |
| 99 | | H₃C-O-X₁₁ | H₃C-(CH₂)₄-X₁₂ | X₁₃-CH₃ | | | H₃C-X₁₆ |
| 100 | X₁₀-O-CH₃ | | X₁₂-CH₂-CH₂-CH(CH₃)- (H₃C-CH(CH₃)-CH₂-CH₂-X₁₂) | X₁₃-CH₃ | | | H₃C-X₁₆ |

-continued
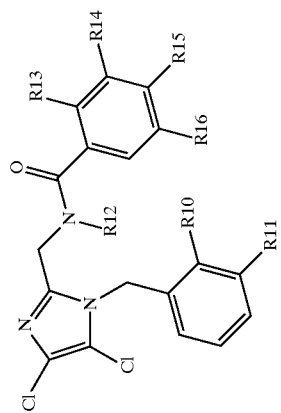
| Ex # | R10 | R11 | R12 | R13 | R14 | R15 | R16 |
|---|---|---|---|---|---|---|---|
| 101 | $H_3C-X_{10}-O$ | | $H_3C-(CH_2)_4-X_{12}$ | $X_{13}-CH_3$ | | $H_3C-X_{15}$ | |
| 102 | | $H_3C-O-X_{11}$ | $X_{12}-CH_2-CH(CH_3)-$ | $X_{13}-CH_3$ | | $H_3C-X_{15}$ | |
| 103 | | $H_3C-O-X_{11}$ | $H_3C-(CH_2)_4-X_{12}$ | $X_{13}-CH_3$ | | $H_3C-X_{15}$ | |

-continued
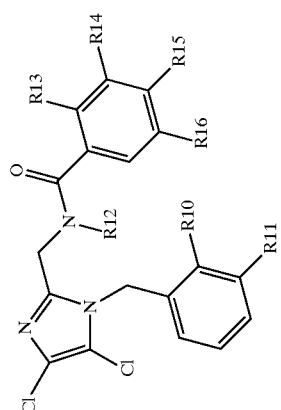
| Ex # | R10 | R11 | R12 | R13 | R14 | R15 | R16 |
|---|---|---|---|---|---|---|---|
| 104 | X10—O—CH3 | | X12—CH2CH2—CH(CH3)—CH3 | CH3—X13 | | | |
| 105 | X10—O—CH3 | | H3C—(CH2)4—X12 | | | | |
| 106 | | H3C—O—X11 | X12—CH2CH2—CH(CH3)—CH3 | | CH3—O—X14 | H3C—X15 | |

-continued
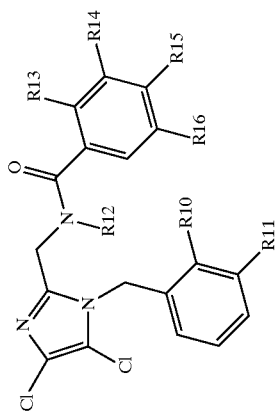
| Ex # | R10 | R11 | R12 | R13 | R14 | R15 | R16 |
|---|---|---|---|---|---|---|---|
| 107 | | H₃C-O-X₁₁ | H₃C-(CH₂)₄-X₁₂ | | CH₃-O-X₁₄ | | |
| 108 | X₁₀-O-CH₃ | | X₁₂-CH₂CH₂-CH(CH₃)- | | CH₃-O-X₁₄ | | |
| 109 | X₁₀-O-CH₃ | | H₃C-(CH₂)₄-X₁₂ | | | H₃C-O-X₁₅ | |

-continued
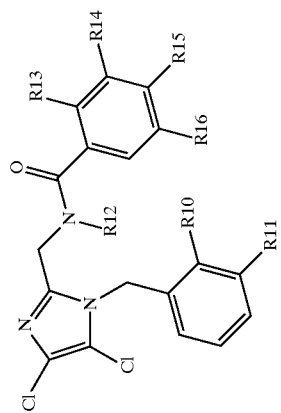
| Ex # | R10 | R11 | R12 | R13 | R14 | R15 | R16 |
|---|---|---|---|---|---|---|---|
| 110 | | H₃C−O−X₁₁ | X₁₂−CH(CH₃)−CH₂−CH₂ / H₃C | | | H₃C−O−X₁₅ | |
| 111 | | H₃C−O−X₁₁ | H₃C−CH₂−CH₂−CH₂−CH₂−X₁₂ | | | H₃C−O−X₁₅ | |
| 112 | X₁₀−O−CH₃ | | X₁₂−CH(CH₃)−CH₂−CH₂ / H₃C | | | H₃C−O−X₁₅ | |

-continued
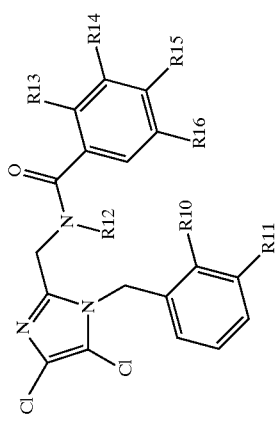
| Ex # | R10 | R11 | R12 | R13 | R14 | R15 | R16 |
|------|-----|-----|-----|-----|-----|-----|-----|
| 113 | $X_{10}$—O—CH$_3$ (H$_3$C—O—$X_{10}$) | | H$_3$C—(CH$_2$)$_4$—$X_{12}$ | $X_{13}$—O—CH$_3$ | | | |
| 114 | | H$_3$C—O—$X_{11}$ | $X_{12}$—CH$_2$—CH$_2$—CH(CH$_3$)—$X_{12}$ (branched) | H$_3$C—O—$X_{13}$ | | | |
| 115 | | H$_3$C—O—$X_{11}$ | H$_3$C—(CH$_2$)$_4$—$X_{12}$ | $X_{13}$—O—CH$_3$ | | | |

-continued
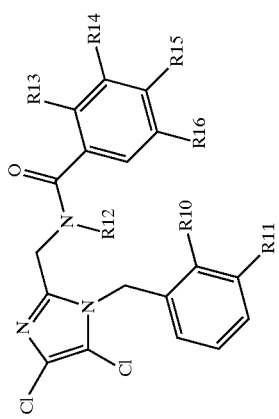
| Ex # | R10 | R11 | R12 | R13 | R14 | R15 | R16 |
|---|---|---|---|---|---|---|---|
| 116 | X₁₀—O—CH₃ | | H₃C—CH(CH₃)—CH₂—CH₂—X₁₂ | H₃C—O—X₁₃ | F—X₁₄ | H₃C—X₁₅ | |
| 117 | X₁₀—O—CH₃ | | H₃C—CH₂—CH₂—CH₂—CH₂—X₁₂ | | | | |
| 118 | | H₃C—O—X₁₁ | H₃C—CH(CH₃)—CH₂—CH₂—X₁₂ | | F—X₁₄ | H₃C—X₁₅ | |

| Ex # | R10 | R11 | R12 | R13 | R14 | R15 | R16 |
|---|---|---|---|---|---|---|---|
| 119 |  | H₃C-O-X₁₁ | H₃C-(CH₂)₄-X₁₂ |  | F-X₁₄ | H₃C-X₁₅ |  |
| 120 | X₁₀-O-CH₃ |  | X₁₂-CH₂-CH₂-CH(CH₃)-CH₃ |  | F-X₁₄ | H₃C-X₁₅ |  |
| 121 | X₁₀-O-CH₃ |  | H₃C-(CH₂)₄-X₁₂ | X₁₃-CH₃ | F-X₁₄ |  |  |

-continued
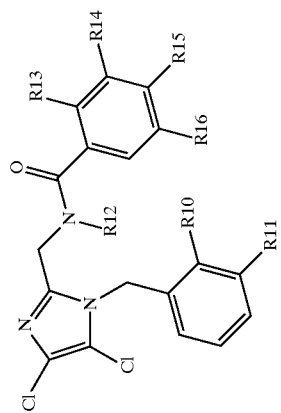
| Ex # | R10 | R11 | R12 | R13 | R14 | R15 | R16 |
|---|---|---|---|---|---|---|---|
| 122 | | H₃C-O-X₁₁ | X₁₂-CH₂-CH₂-CH(CH₃)-CH₃ | X₁₃-CH₃ | F-X₁₄ | | |
| 123 | | H₃C-O-X₁₁ | H₃C-(CH₂)₄-X₁₂ | X₁₃-CH₃ | X₁₄-F | | |
| 124 | X₁₀-O-CH₃ | | X₁₂-CH₂-CH₂-CH(CH₃)-CH₃ | X₁₃-CH₃ | F-X₁₄ | | |

-continued
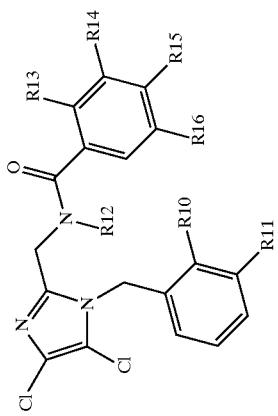
| Ex # | R10 | R11 | R12 | R13 | R14 | R15 | R16 |
|---|---|---|---|---|---|---|---|
| 125 | $X_{10}$—O—$CH_3$ | | $H_3C$—————$X_{12}$ | | | | $X_{16}$—F |
| 126 | | $H_3C$—O—$X_{11}$ | $X_{12}$————$CH(CH_3)$—$CH_3$ | $X_{13}$—$CH_3$ | | | $X_{16}$—F |
| 127 | | $H_3C$—O—$X_{11}$ | $H_3C$—————$X_{12}$ | $X_{13}$—$CH_3$ | | | $X_{16}$—F |

-continued
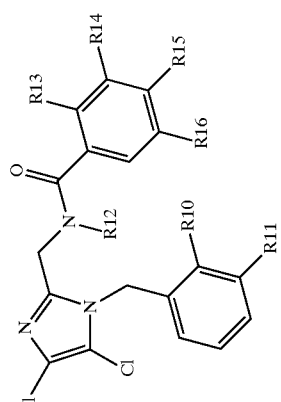
| Ex # | R10 | R11 | R12 | R13 | R14 | R15 | R16 |
|---|---|---|---|---|---|---|---|
| 128 | X10—O—CH3 | | X12—CH2CH2—CH(CH3)—CH3 (H3C) | X13—CH3 | | | |
| 129 | X10—O—CH3 | | H3C—(CH2)4—X12 | X13—F | | | |
| 130 | | H3C—O—X11 | X12—CH2CH2—CH(CH3)—CH3 (H3C) | F—X13 | H3C—X14 | | |
| | | | | | H3C—X14 | | X16—F |

-continued
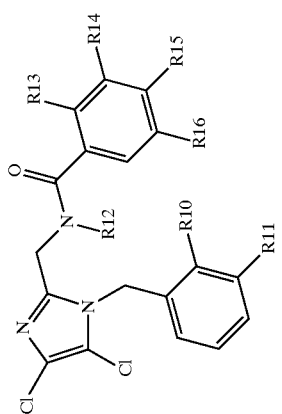
| Ex # | R10 | R11 | R12 | R13 | R14 | R15 | R16 |
|---|---|---|---|---|---|---|---|
| 131 | | H3C-O-X11 | H3C-~~~-X12 | X13-F | H3C-X14 | | |
| 132 | X10-O-CH3 | | X12-CH(CH3)-CH2-CH2-CH3 | F-X13 | H3C-X14 | | |
| 133 | X10-O-CH3 | | H3C-~~~-X12 | | Cl-X14 | | |

-continued
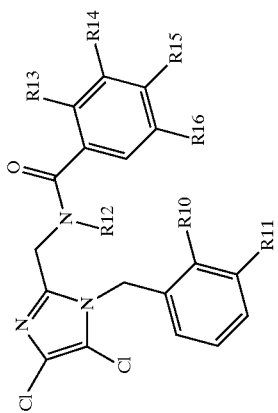
| Ex # | R10 | R11 | R12 | R13 | R14 | R15 | R16 |
|---|---|---|---|---|---|---|---|
| 134 | | H3C–O–X11 | X12–CH2CH2–CH(CH3)–CH3 (with H3C branch) | | Cl–X14 | | |
| 135 | | H3C–O–X11 | H3C–CH2CH2CH2CH2–X12 | | Cl–X14 | | |
| 136 | X10–O–CH3 | | X12–CH2CH2–CH(CH3)–CH3 (with H3C branch) | | Cl–X14 | | |

-continued
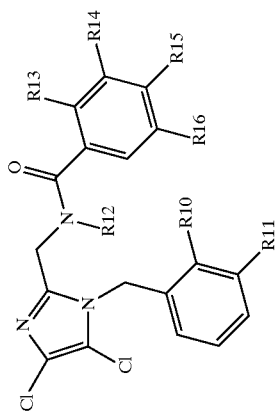
| Ex # | R10 | R11 | R12 | R13 | R14 | R15 | R16 |
|---|---|---|---|---|---|---|---|
| 137 | $H_3C-O-X_{10}$ | | $H_3C-CH_2CH_2CH_2CH_2-X_{12}$ | | | $Cl-X_{15}$ | |
| 138 | | $H_3C-O-X_{11}$ | $X_{12}-CH_2CH_2-CH(CH_3)-$ | | | $Cl-X_{15}$ | |
| 139 | | $H_3C-O-X_{11}$ | $H_3C-CH_2CH_2CH_2CH_2-X_{12}$ | | | $Cl-X_{15}$ | |

-continued
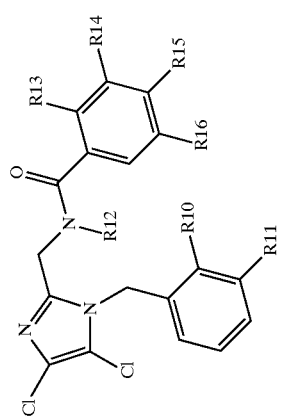
| Ex # | R10 | R11 | R12 | R13 | R14 | R15 | R16 |
|---|---|---|---|---|---|---|---|
| 140 | X10—O—CH3 | | X12—CH2CH2—CH(CH3)—CH3 (H3C) | | | Cl—X15 | |
| 141 | X10—O—CH3 | | H3C—(CH2)4—X12 | X13—Cl | | | |
| 142 | | H3C—O—X11 | X12—CH2CH2—CH(CH3)—CH3 (H3C) | X13—Cl | | | |

-continued
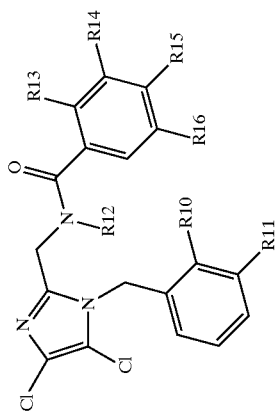
| Ex # | R10 | R11 | R12 | R13 | R14 | R15 | R16 |
|------|-----|-----|-----|-----|-----|-----|-----|
| 143 | | H₃C–O–X₁₁ | H₃C~~~X₁₂ | X₁₃–Cl | | | |
| 144 | X₁₀–O–CH₃ | | X₁₂CH(CH₃)CH₂CH₂– with H₃C | Cl–X₁₃ | | | |
| 145 | X₁₀–O–CH₃ | | H₃C~~~X₁₂ | | F–X₁₄ | F–X₁₅ | |

-continued
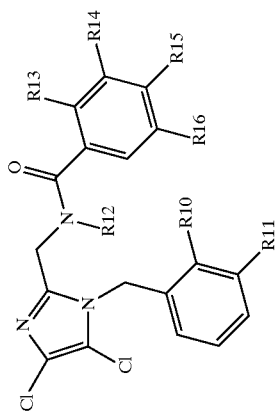
| Ex # | R10 | R11 | R12 | R13 | R14 | R15 | R16 |
|---|---|---|---|---|---|---|---|
| 146 | | H₃C–O–X₁₁ | X₁₂–CH(CH₃)–... (H₃C) | | F–X₁₄ | F–X₁₅ | |
| 147 | | H₃C–O–X₁₁ | H₃C–...–X₁₂ | | F–X₁₄ | F–X₁₅ | |
| 148 | X₁₀–O–CH₃ | | X₁₂–CH(CH₃)–... (H₃C) | | F–X₁₄ | F–X₁₅ | |

-continued

| Ex # | R10 | R11 | R12 | R13 | R14 | R15 | R16 |
|------|-----|-----|-----|-----|-----|-----|-----|
| 149 | H₃C-O-X₁₀ | | H₃C-(CH₂)₄-X₁₂ | X₁₃-F | X₁₄-F | | |
| 150 | | H₃C-O-X₁₁ | X₁₂-CH₂CH₂-CH(CH₃)- | X₁₃-F | X₁₄-F | | |
| 151 | | H₃C-O-X₁₁ | H₃C-(CH₂)₄-X₁₂ | X₁₃-F | X₁₄-F | | |

-continued
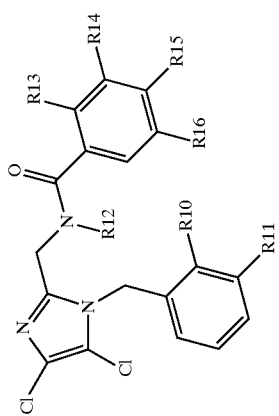
| Ex # | R10 | R11 | R12 | R13 | R14 | R15 | R16 |
|---|---|---|---|---|---|---|---|
| 152 | X10—O—CH3 | | X12\~\~\~CH(CH3)—CH3 | F—X13 | F—X14 | | |
| 153 | X10—O—CH3 | | H3C\~\~\~\~X12 | X13—F | | | F—X16 |
| 154 | | H3C—O—X11 | X12\~\~\~CH(CH3)—CH3 | F—X13 | | | F—X16 |

-continued

| Ex # | R10 | R11 | R12 | R13 | R14 | R15 | R16 |
|---|---|---|---|---|---|---|---|
| 155 | | H₃C-O-X₁₁ | H₃C-(CH₂)₄-X₁₂ | X₁₃-F | | | F-X₁₆ |
| 156 | X₁₀-O-CH₃ | | X₁₂-CH₂-CH(CH₃)-CH₃ (with CH₃) | X₁₃-F | | | F-X₁₆ |
| 157 | X₁₀-O-CH₃ | | H₃C-(CH₂)₄-X₁₂ | X₁₃-F | | F-X₁₅ | |

-continued
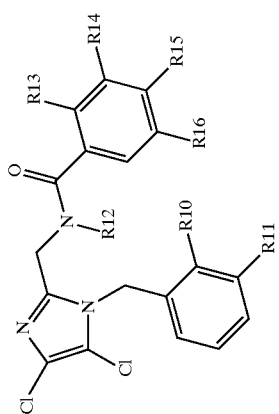
| Ex # | R10 | R11 | R12 | R13 | R14 | R15 | R16 |
|---|---|---|---|---|---|---|---|
| 158 |  | H3C-O-X11 | X12-CH2CH2-CH(CH3)-CH3 | F-X13 |  | F-X15 |  |
| 159 |  | H3C-O-X11 | H3C-(CH2)4-X12 | X13-F |  | F-X15 |  |
| 160 | X10-O-CH3 |  | X12-CH2CH2-CH(CH3)-CH3 | F-X13 |  | F-X15 |  |

-continued
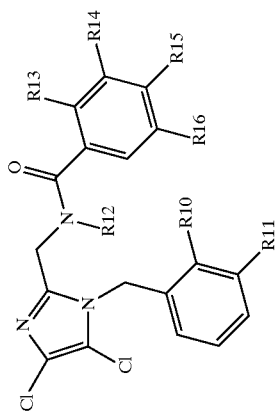
| Ex # | R10 | R11 | R12 | R13 | R14 | R15 | R16 |
|---|---|---|---|---|---|---|---|
| 161 | H3C—O—X10 | | H3C~~~X12 | | | H3C~X15 | |
| 162 | | H3C-O-X11 | X12~~CH(CH3)-CH3 | | | H3C~X15 | |
| 163 | | H3C-O-X11 | H3C~~~X12 | | | H3C~X15 | |

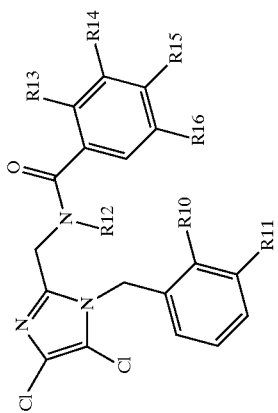

-continued
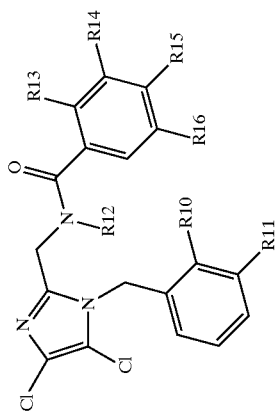
| Ex # | R10 | R11 | R12 | R13 | R14 | R15 | R16 |
|---|---|---|---|---|---|---|---|
| 167 | | H₃C-O-X₁₁ | H₃C-(CH₂)₄-X₁₂ | | | H₃C-CH(CH₃)-X₁₅ | |
| 168 | X₁₀-O-CH₃ | | X₁₂-CH₂-CH₂-CH(CH₃)-CH₃ | | H₃C-O-X₁₄ | H₃C-CH(CH₃)-X₁₅ | |
| 169 | X₁₀-O-CH₃ | | H₃C-(CH₂)₄-X₁₂ | | | | |

-continued
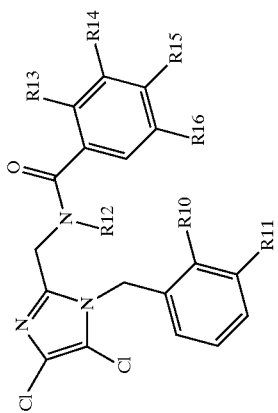
| Ex # | R10 | R11 | R12 | R13 | R14 | R15 | R16 |
|---|---|---|---|---|---|---|---|
| 170 | | H₃C-O-X₁₁ | X₁₂-CH₂CH₂-CH(CH₃)-CH₃ | | H₃C-O-X₁₄ | | |
| 171 | | H₃C-O-X₁₁ | H₃C-CH₂CH₂CH₂CH₂-X₁₂ | | H₃C-O-X₁₄ | | |
| 172 | X₁₀-O-CH₃ | | X₁₂-CH₂CH₂-CH(CH₃)-CH₃ | | H₃C-O-X₁₄ | | |

-continued
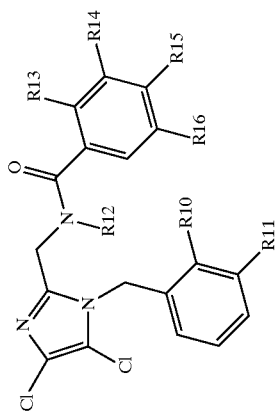
| Ex # | R10 | R11 | R12 | R13 | R14 | R15 | R16 |
|---|---|---|---|---|---|---|---|
| 173 | X10—O—CH3 | | H3C~~~X12 | | | H3C—O—X15 | |
| 174 | | H3C—O—X11 | X12—CH(CH3)— (CH2)—CH3 | | | H3C—O—X15 | |
| 175 | | H3C—O—X11 | H3C~~~X12 | | | H3C—O—X15 | |

-continued
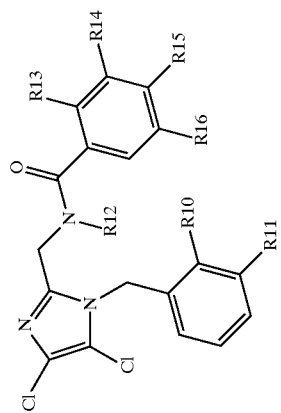
| Ex # | R10 | R11 | R12 | R13 | R14 | R15 | R16 |
|---|---|---|---|---|---|---|---|
| 176 | X10—O—CH3 | | X12—CH2CH2—CH(CH3)—CH3 | | | H3C—CH2—O—X15 | |
| 177 | | X10—O—CH3 | H3C—CH2CH2CH2CH2—X12 | X13—O—CH2—CH3 | | | |
| 178 | | H3C—O—X11 | X12—CH2CH2—CH(CH3)—CH3 | CH3—CH2—O—X13 | | | |

| Ex # | R10 | R11 | R12 | R13 | R14 | R15 | R16 |
|---|---|---|---|---|---|---|---|
| 179 |  | H₃C–O–X₁₁ | H₃C–(CH₂)₄–X₁₂ | X₁₃–O–CH₂–CH₃ |  |  |  |
| 180 | X₁₀–O–CH₃ |  | X₁₂–CH₂–CH₂–CH(CH₃)– (H₃C–CH(X₁₂)–CH₂–CH₂–) | CH₃–O–CH₂–X₁₃ |  |  |  |
| 181 | X₁₀–O–CH₃ |  | H₃C–(CH₂)₄–X₁₂ |  | (X₁₄–X₁₅ methylenedioxy ring) |  |  |

-continued
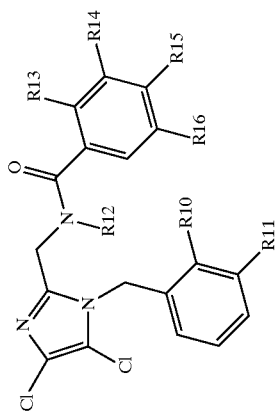
| Ex # | R10 | R11 | R12 | R13 | R14 | R15 | R16 |
|---|---|---|---|---|---|---|---|
| 182 | | H₃C-O-X₁₁ | X₁₂-CH₂CH₂-CH(CH₃)-CH₃ (H₃C on branch) | | O-X₁₄-X₁₅-O (dioxolane) | | |
| 183 | | H₃C-O-X₁₁ | H₃C-(CH₂)₄-X₁₂ | | O-X₁₄-X₁₅-O (dioxolane) | | |
| 184 | X₁₀-O-CH₃ | | X₁₂-CH₂CH₂-CH(CH₃)-CH₃ (H₃C on branch) | | O-X₁₄-X₁₅-O (dioxolane) | | |

-continued

[Structure: benzamide with R13, R14, R15, R16 substituents on phenyl, connected via C(=O)-N(R12)-CH2- to an imidazole bearing two Cl substituents and N-CH2-(2,3-disubstituted phenyl with R10, R11)]

| Ex # | R10 | R11 | R12 | R13 | R14 | R15 | R16 |
|---|---|---|---|---|---|---|---|
| 185 | H₃C—O—X₁₀ | | H₃C—(CH₂)₄—X₁₂ | | | H₃C—S—X₁₅ | |
| 186 | | H₃C—O—X₁₁ | X₁₂—CH₂CH₂—CH(CH₃)— | | | H₃C—S—X₁₅ | |
| 187 | | H₃C—O—X₁₁ | H₃C—(CH₂)₄—X₁₂ | | | H₃C—S—X₁₅ | |

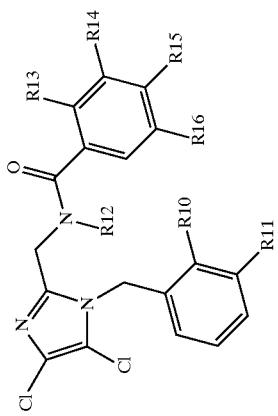

-continued
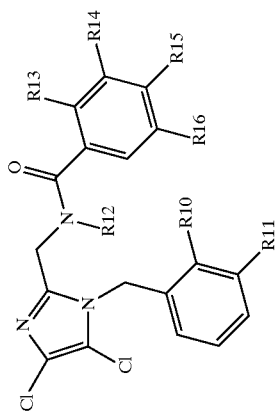
| Ex # | R10 | R11 | R12 | R13 | R14 | R15 | R16 |
|---|---|---|---|---|---|---|---|
| 191 | H₃C—O—X10 | H₃C—O—X11 | H₃C—(CH₂)₄—X12 | | F—X14 | H₃C—O—X15 | |
| 192 | X10—O—CH₃ | | X12—CH₂CH₂—CH(CH₃)—(with H₃C) | | F—X14 | H₃C—O—X15 | |
| 193 | X10—O—CH₃ | | H₃C—(CH₂)₄—X12 | | H₃C—X14 | Cl—X15 | |

-continued
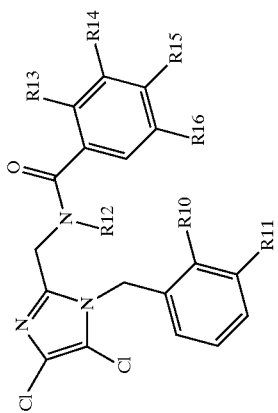
| Ex # | R10 | R11 | R12 | R13 | R14 | R15 | R16 |
|------|-----|-----|-----|-----|-----|-----|-----|
| 194 | | H3C-O-X11 | X12-CH2CH2-CH(CH3)-CH3 | | H3C-X14 | Cl-X15 | |
| 195 | | H3C-O-X11 | H3C-CH2CH2CH2CH2-X12 | | H3C-X14 | Cl-X15 | |
| 196 | X10-O-CH3 | | X12-CH2CH2-CH(CH3)-CH3 | | H3C-X14 | Cl-X15 | |

-continued
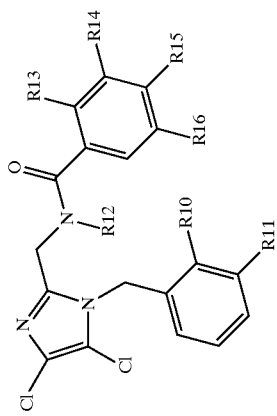
| Ex # | R10 | R11 | R12 | R13 | R14 | R15 | R16 |
|---|---|---|---|---|---|---|---|
| 197 | H3C—O—X10 | | H3C~~~X12 | | Cl—X14 | F—X15 | |
| 198 | | H3C—O—X11 | X12~CH(CH3)~ | | Cl—X14 | F—X15 | |
| 199 | | H3C—O—X11 | H3C~~~X12 | | Cl—X14 | F—X15 | |

-continued
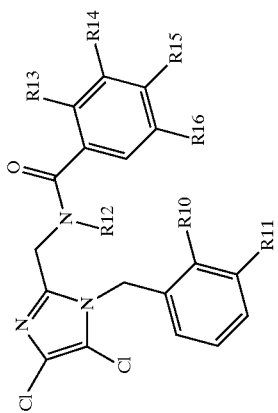
| Ex # | R10 | R11 | R12 | R13 | R14 | R15 | R16 |
|---|---|---|---|---|---|---|---|
| 200 | $X_{10}$—O—$CH_3$ | | $X_{12}$—CH$_2$—CH$_2$—CH(CH$_3$)—CH$_3$ | | Cl—$X_{14}$ | F—$X_{15}$ | $X_{16}$—F |
| 201 | $X_{10}$—O—CH$_3$ | | H$_3$C—CH$_2$—CH$_2$—CH$_2$—CH$_2$—$X_{12}$ | | F—$X_{14}$ | F—$X_{15}$ | $X_{16}$—F |
| 202 | | H$_3$C—O—$X_{11}$ | $X_{12}$—CH$_2$—CH$_2$—CH(CH$_3$)—CH$_3$ | | F—$X_{14}$ | F—$X_{15}$ | $X_{16}$—F |

-continued
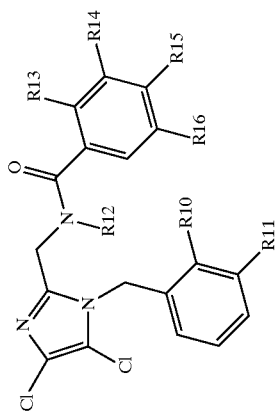
| Ex # | R10 | R11 | R12 | R13 | R14 | R15 | R16 |
|---|---|---|---|---|---|---|---|
| 203 | | H₃C–O–X₁₁ | H₃C~~~X₁₂ | | F—X₁₄ | F—X₁₅ | F—X₁₆ |
| 204 | X₁₀–O–CH₃ | | X₁₂~~CH(CH₃)~CH₃ | | F—X₁₄ | F—X₁₅ | F—X₁₆ |
| 205 | X₁₀–O–CH₃ | | H₃C~~~X₁₂ | | | H₃C~~~O~X₁₅ | |

-continued

| Ex # | R10 | R11 | R12 | R13 | R14 | R15 | R16 |
|---|---|---|---|---|---|---|---|
| 206 | | H₃C-O-X₁₁ | X₁₂-CH₂-CH₂-CH(CH₃)-CH₃ (with H₃C branch) | | | X₁₅-CH₂CH₂CH₂-CH₃ | |
| 207 | | H₃C-O-X₁₁ | H₃C-(CH₂)₄-X₁₂ | | | X₁₅-CH₂CH₂CH₂-CH₃ | |
| 208 | X₁₀-O-CH₃ | | X₁₂-CH₂-CH₂-CH(CH₃)-CH₃ (with H₃C branch) | | | X₁₅-CH₂CH₂CH₂-CH₃ | |

-continued
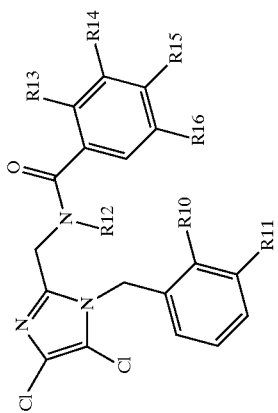
| Ex # | R10 | R11 | R12 | R13 | R14 | R15 | R16 |
|---|---|---|---|---|---|---|---|
| 209 | H3C—O—X10 | | H3C~~~X12 | | | H3C-C(CH3)(CH3)-X15 | |
| 210 | | H3C-O-X11 | X12-CH2CH2-CH(CH3)-CH3 | | | H3C-C(CH3)(CH3)-X15 | |
| 211 | | H3C-O-X11 | H3C~~~X12 | | | H3C-C(CH3)(CH3)-X15 | |

-continued
| Ex # | R10 | R11 | R12 | R13 | R14 | R15 | R16 |
|---|---|---|---|---|---|---|---|
| 212 | X10—O—CH3 | | X12-CH2CH2-CH(CH3)-CH3 (H3C-CH(X12)-CH2CH2-) | | | H3C-C(CH3)(CH3)-X15 | |
| 213 | X10—O-CH3 | | H3C-CH2CH2CH2CH2-X12 | | | H3C-CH2-O-X15 | |
| 214 | | H3C-O-X11 | X12-CH2CH2-CH(CH3)-CH3 | | | H3C-CH2-O-X15 | |
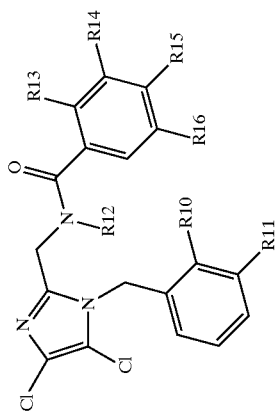

-continued
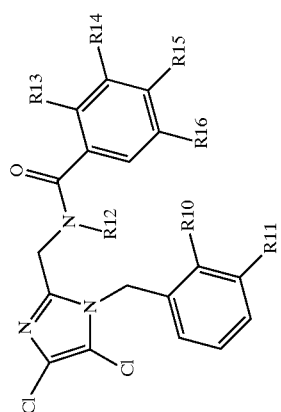
| Ex # | R10 | R11 | R12 | R13 | R14 | R15 | R16 |
|---|---|---|---|---|---|---|---|
| 215 | | H3C-O-X11 | H3C-(CH2)4-X12 | | | O-X15, H3C-CH2- | |
| 216 | X10-O-CH3 | | X12-CH2-CH2-CH(CH3)- | | | O-X15, H3C-CH2- | |
| 217 | X10-O-CH3 | | H3C-(CH2)4-X12 | | | O-X15, H3C-CH- | |

-continued
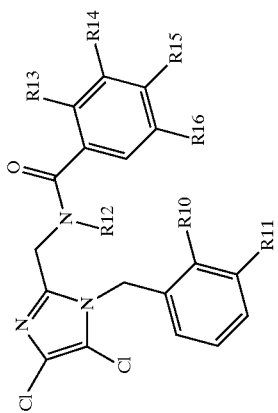
| Ex # | R10 | R11 | R12 | R13 | R14 | R15 | R16 |
|---|---|---|---|---|---|---|---|
| 218 | | H3C—O—X11 | X12—CH2CH2—CH(CH3)—CH3 | | | O—X15, CH(CH3)(H3C) | |
| 219 | | H3C—O—X11 | H3C—(CH2)4—X12 | | | O—X15, CH(CH3)(H3C) | |
| 220 | X10—O—CH3 | | X12—CH2CH2—CH(CH3)—CH3 | | | O—X15, CH(CH3)(H3C) | |

-continued
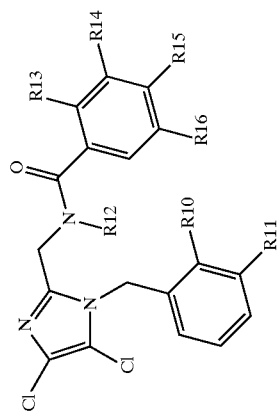
| Ex # | R10 | R11 | R12 | R13 | R14 | R15 | R16 |
|---|---|---|---|---|---|---|---|
| 221 | H3C—O—X10 | | H3C~~~X12 | | | S—X15 (with H3C) | |
| 222 | | H3C—O—X11 | X12~~CH(CH3)~~ (H3C) | | | S—X15 (with H3C) | |
| 223 | | H3C—O—X11 | H3C~~~X12 | | | S—X15 (with H3C) | |

-continued
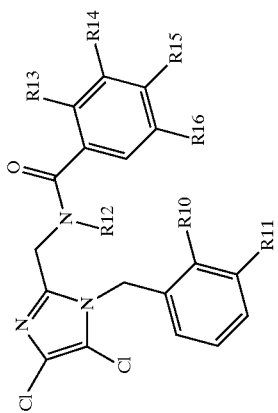
| Ex # | R10 | R11 | R12 | R13 | R14 | R15 | R16 |
|---|---|---|---|---|---|---|---|
| 224 | X₁₀—O—CH₃ | | X₁₂—CH₂CH₂CH(CH₃)—CH₃ | | | H₃C—CH₂—S—X₁₅ | |
| 225 | X₁₀—O—CH₃ | | H₃C—(CH₂)₄—X₁₂ | | H₃C—O(CH₃)—X₁₄ | H₃C—O—X₁₅ | |
| 226 | | H₃C—O—X₁₁ | X₁₂—CH₂CH₂CH(CH₃)—CH₃ | | H₃C—O(CH₃)—X₁₄ | H₃C—O—X₁₅ | |

-continued
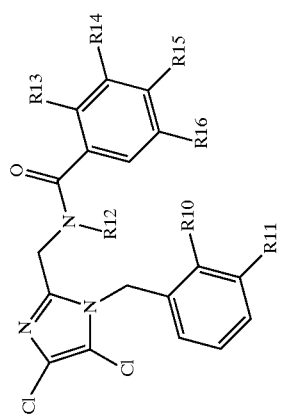
| Ex # | R10 | R11 | R12 | R13 | R14 | R15 | R16 |
|---|---|---|---|---|---|---|---|
| 227 |  | H$_3$C-O-X$_{11}$ | H$_3$C~~~~X$_{12}$ |  | CH$_3$-O-X$_{14}$ | H$_3$C-O-X$_{15}$ |  |
| 228 | X$_{10}$-O-CH$_3$ |  | X$_{12}$CH(CH$_3$)CH$_2$CH$_3$ |  | CH$_3$-O-X$_{14}$ | H$_3$C-O-X$_{15}$ |  |
| 229 | X$_{10}$-O-CH$_3$ |  | H$_3$C~~~~X$_{12}$ |  | CH$_3$-O-X$_{14}$ |  | H$_3$C-O-X$_{16}$ |

-continued
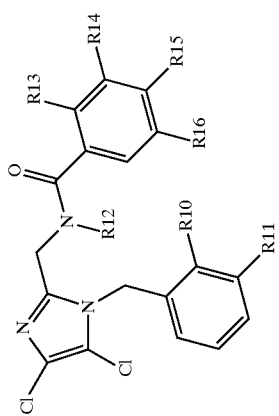
| Ex # | R10 | R11 | R12 | R13 | R14 | R15 | R16 |
|---|---|---|---|---|---|---|---|
| 230 | | H₃C−O−X₁₁ | X₁₂−CH₂−CH₂−CH(CH₃)−CH₃ | | CH₃−O−X₁₄ | | H₃C−O−X₁₆ |
| 231 | | H₃C−O−X₁₁ | H₃C−(CH₂)₄−X₁₂ | | CH₃−O−X₁₄ | | H₃C−O−X₁₆ |
| 232 | X₁₀−O−CH₃ | | X₁₂−CH₂−CH₂−CH(CH₃)−CH₃ | | CH₃−O−X₁₄ | | H₃C−O−X₁₆ |

-continued
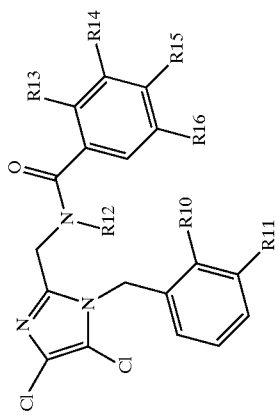
| Ex # | R10 | R11 | R12 | R13 | R14 | R15 | R16 |
|---|---|---|---|---|---|---|---|
| 233 | H3C—O—X10 | | H3C—CH2—CH2—CH2—CH2—X12 | X13—O—CH3 | H3C—O—X14 | | |
| 234 | | H3C—O—X11 | X12—CH2—CH2—CH(CH3) | H3C—O—X13 | H3C—O—X14 | | |
| 235 | | H3C—O—X11 | H3C—CH2—CH2—CH2—CH2—X12 | X13—O—CH3 | H3C—O—X14 | | |

-continued
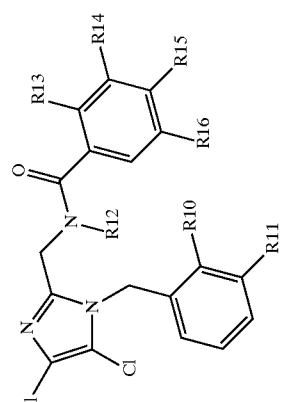
| Ex # | R10 | R11 | R12 | R13 | R14 | R15 | R16 |
|---|---|---|---|---|---|---|---|
| 236 | X10—O—CH3 | | X12—CH2CH2—CH(CH3)—CH3 | H3C—O—X13 | H3C—O—X14 | | CH3—O—X16 |
| 237 | X10—O—CH3 | | H3C—CH2CH2CH2CH2—X12 | X13—O—CH3 | | | |
| 238 | | H3C—O—X11 | X12—CH2CH2—CH(CH3)—CH3 | H3C—O—X13 | | | X16—O—CH3 |

-continued
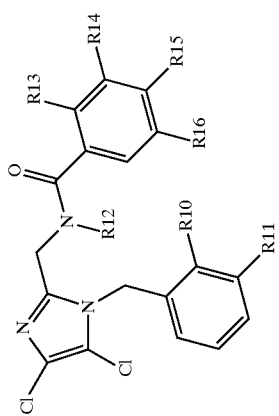
| Ex # | R10 | R11 | R12 | R13 | R14 | R15 | R16 |
|---|---|---|---|---|---|---|---|
| 239 | | H₃C–O–X₁₁ | H₃C~~~X₁₂ | X₁₃–O–CH₃ | | | CH₃–O–X₁₆ |
| 240 | X₁₀–O–CH₃ | | X₁₂~~~CH(CH₃)–CH₃ | H₃C–O–X₁₃ | | | X₁₆–O–CH₃ |
| 241 | X₁₀–O–CH₃ | | H₃C~~~X₁₂ | X₁₃–O–CH₃ | | H₃C–O–X₁₅ | |

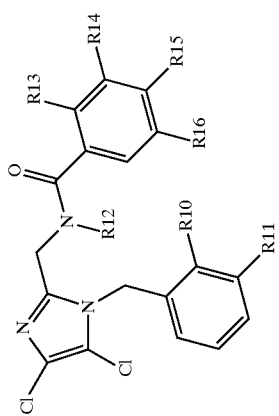
| Ex # | R10 | R11 | R12 | R13 | R14 | R15 | R16 |
|---|---|---|---|---|---|---|---|
| 242 |  | H3C-O-X11 | X12-CH2CH2-CH(CH3)-CH3 | H3C-O-X13 |  | H3C-O-X15 |  |
| 243 |  | H3C-O-X11 | H3C-CH2CH2CH2CH2-X12 | X13-O-CH3 |  | H3C-O-X15 |  |
| 244 | X10-O-CH3 |  | X12-CH2CH2-CH(CH3)-CH3 | H3C-O-X13 |  | H3C-O-X15 |  |

-continued
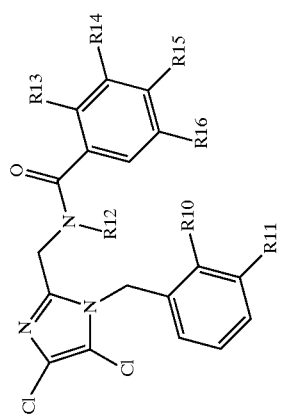
| Ex # | R10 | R11 | R12 | R13 | R14 | R15 | R16 |
|---|---|---|---|---|---|---|---|
| 245 | H3C—O—X10 | | H3C—...—X12 | | Cl—X14 | H3C—O—X15 | |
| 246 | | H3C—O—X11 | X12—...—CH3 (with CH3) | | Cl—X14 | H3C—O—X15 | |
| 247 | | H3C—O—X11 | H3C—...—X12 | | Cl—X14 | H3C—O—X15 | |

-continued
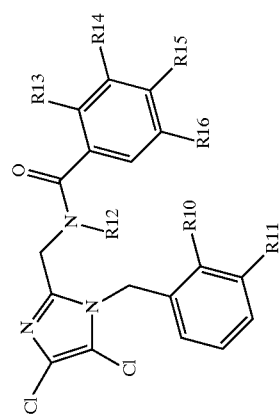
| Ex # | R10 | R11 | R12 | R13 | R14 | R15 | R16 |
|---|---|---|---|---|---|---|---|
| 248 | $X_{10}$—O—$CH_3$ | | $X_{12}$-CH$_2$CH$_2$-CH(CH$_3$)-CH$_3$ | $X_{13}$—O—CH$_3$ | Cl—$X_{14}$ | $H_3C$—O—$X_{15}$ | Cl—$X_{16}$ |
| 249 | $X_{10}$—O—$H_3C$ | | $H_3C$-(CH$_2$)$_4$-$X_{12}$ | $H_3C$—O—$X_{13}$ | | | Cl—$X_{16}$ |
| 250 | | $H_3C$—O—$X_{11}$ | $X_{12}$-CH$_2$CH$_2$-CH(CH$_3$)-CH$_3$ | $H_3C$—O—$X_{13}$ | | | |

-continued

| Ex # | R10 | R11 | R12 | R13 | R14 | R15 | R16 |
|---|---|---|---|---|---|---|---|
| 251 | | H₃C-O-X₁₁ | H₃C~~~X₁₂ | | | | Cl-X₁₆ |
| 252 | X₁₀-O-CH₃ | | X₁₂-CH(CH₃)- | H₃C-O-X₁₃ | | | Cl-X₁₆ |
| 253 | X₁₀-O-CH₃ | | H₃C~~~X₁₂ | X₁₃-O-CH₃ | | Cl-X₁₅ | |

-continued
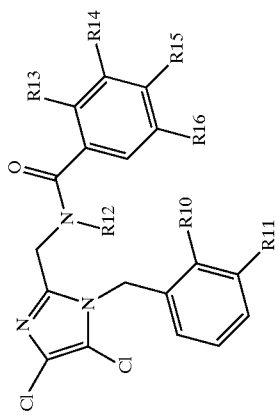
| Ex # | R10 | R11 | R12 | R13 | R14 | R15 | R16 |
|---|---|---|---|---|---|---|---|
| 254 | | H3C—O—X11 | X12—CH2CH2—CH(CH3)— | H3C—O—X13 | | Cl—X15 | |
| 255 | | H3C—O—X11 | H3C—(CH2)4—X12 | X13—O—CH3 | | Cl—X15 | |
| 256 | X10—O—CH3 | | X12—CH2CH2—CH(CH3)— | H3C—O—X13 | | Cl—X15 | |

-continued
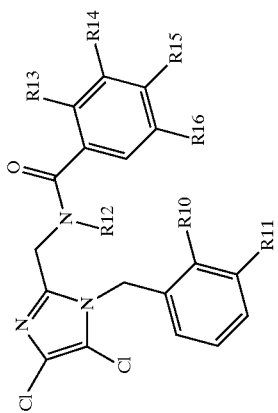
| Ex # | R10 | R11 | R12 | R13 | R14 | R15 | R16 |
|---|---|---|---|---|---|---|---|
| 257 | $X_{10}$—O—$CH_3$ | | $H_3C$—$(CH_2)_3$—$X_{12}$ | | $CF_3$-$X_{14}$ | | |
| 258 | | $H_3C$—O—$X_{11}$ | $X_{12}$—$CH_2CH_2$—CH($CH_3$)—$CH_3$ | | $CF_3$-$X_{14}$ | | |
| 259 | | $H_3C$—O—$X_{11}$ | $H_3C$—$(CH_2)_3$—$X_{12}$ | | $CF_3$-$X_{14}$ | | |

-continued
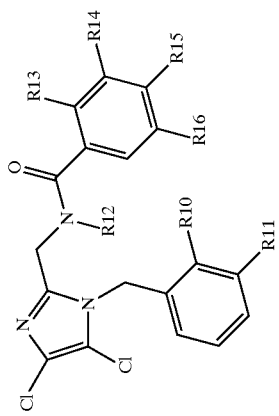
| Ex # | R10 | R11 | R12 | R13 | R14 | R15 | R16 |
|---|---|---|---|---|---|---|---|
| 260 | X₁₀—O—CH₃ | | X₁₂–CH₂–CH₂–CH(CH₃)–CH₃ (with H₃C) | | CF₃–X₁₄ | | |
| 261 | | X₁₀—O—CH₃ | H₃C–(CH₂)₄–X₁₂ | | | CF₃–X₁₅ | |
| 262 | | H₃C—O—X₁₁ | X₁₂–CH₂–CH₂–CH(CH₃)–CH₃ (with H₃C) | | | CF₃–X₁₅ | |

-continued
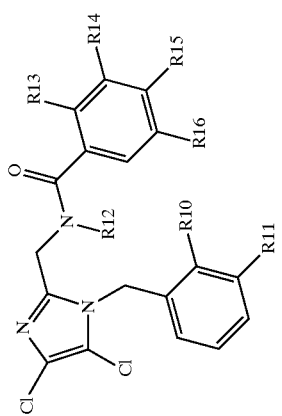
| Ex # | R10 | R11 | R12 | R13 | R14 | R15 | R16 |
|---|---|---|---|---|---|---|---|
| 263 | | H3C—O—X11 | H3C~~~X12 | | | | |
| 264 | X10—O—CH3 | | X12~~CH(CH3)~ | F3C—X13 | | F3C—X15 | |
| 265 | X10—O—CH3 | | H3C~~~X12 | F3C—X13 | | F3C—X15 | |
| 266 | | H3C—O—X11 | X12~~CH(CH3)~ | | | | |

-continued
| Ex # | R10 | R11 | R12 | R13 | R14 | R15 | R16 |
|---|---|---|---|---|---|---|---|
| 267 | H3C—O—X11 | | H3C—(CH2)4—X12 | F3C—X13 | | | |
| 268 | X10—O—CH3 | | X12—CH2CH2—CH(CH3)—CH3 | F3C—X13 | Cl—X14 | | |
| 269 | X10—O—CH3 | | H3C—(CH2)4—X12 | | Cl—X14 | Cl—X15 | |
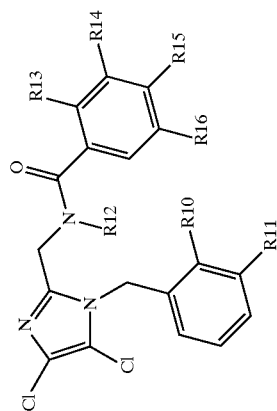

-continued
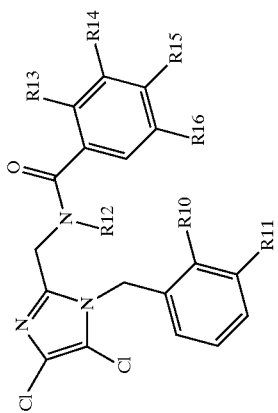
| Ex # | R10 | R11 | R12 | R13 | R14 | R15 | R16 |
|---|---|---|---|---|---|---|---|
| 270 | | H3C-O-X11 | X12-CH2-CH2-CH(CH3)-CH3 | | Cl-X14 | Cl-X15 | |
| 271 | | H3C-O-X11 | H3C-CH2-CH2-CH2-CH2-X12 | | Cl-X14 | Cl-X15 | |
| 272 | X10-O-CH3 | | X12-CH2-CH2-CH(CH3)-CH3 | | Cl-X14 | Cl-X15 | |

-continued
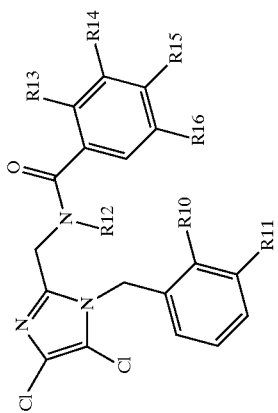
| Ex # | R10 | R11 | R12 | R13 | R14 | R15 | R16 |
|---|---|---|---|---|---|---|---|
| 273 | $X_{10}-O-CH_3$ | | $H_3C\!-\!\!\!\!\!\sim\!\!\!\!\!\sim\!\!\!\!\!-X_{12}$ | | $Cl-X_{14}$ | | $X_{16}-Cl$ |
| 274 | | $H_3C-O-X_{11}$ | $X_{12}\!\!-\!\!\!\sim\!\!\!\!\!-\!\!CH(CH_3)\!-\!H_3C$ | | $Cl-X_{14}$ | | $X_{16}-Cl$ |
| 275 | | $H_3C-O-X_{11}$ | $H_3C\!-\!\!\!\!\!\sim\!\!\!\!\!\sim\!\!\!\!\!-X_{12}$ | | $Cl-X_{14}$ | | $X_{16}-Cl$ |

-continued

| Ex # | R10 | R11 | R12 | R13 | R14 | R15 | R16 |
|---|---|---|---|---|---|---|---|
| 276 | X10—O—CH3 | | X12—CH2CH2—CH(CH3)—CH3 | | Cl—X14 | | Cl—X16 |
| 277 | X10—O—CH3 | | H3C—CH2CH2CH2CH2—X12 | X13—Cl | Cl—X14 | | |
| 278 | H3C—O—X10 | H3C—O—X11 | X12—CH2CH2—CH(CH3)—CH3 | X13—Cl | Cl—X14 | | |

-continued

| Ex # | R10 | R11 | R12 | R13 | R14 | R15 | R16 |
|---|---|---|---|---|---|---|---|
| 279 |  | H₃C—O—X₁₁ | H₃C—(CH₂)₄—X₁₂ | X₁₃—Cl | Cl—X₁₄ |  |  |
| 280 | X₁₀—O—CH₃ |  | X₁₂—CH₂CH₂—CH(CH₃)—CH₃ | X₁₃—Cl | Cl—X₁₄ |  |  |
| 281 | H₃C—O—X₁₀ |  | H₃C—(CH₂)₄—X₁₂ | X₁₃—Cl |  |  | Cl—X₁₆ |

-continued
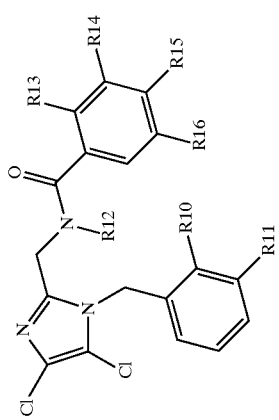
| Ex # | R10 | R11 | R12 | R13 | R14 | R15 | R16 |
|---|---|---|---|---|---|---|---|
| 282 | | H3C—O—X11 | X12—CH2CH2—CH(CH3)—CH3 | X13—Cl | | | X16—Cl |
| 283 | | H3C—O—X11 | H3C—CH2CH2CH2CH2—X12 | X13—Cl | | | X16—Cl |
| 284 | X10—O—CH3 | | X12—CH2CH2—CH(CH3)—CH3 | X13—Cl | | | X16—Cl |

-continued
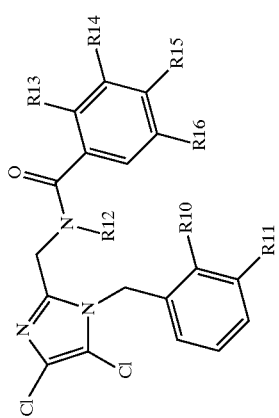
| Ex # | R10 | R11 | R12 | R13 | R14 | R15 | R16 |
|---|---|---|---|---|---|---|---|
| 285 | X₁₀—O—CH₃ | | H₃C—(CH₂)₄—X₁₂ | X₁₃—Cl | | Cl—X₁₅ | |
| 286 | | H₃C—O—X₁₁ | X₁₂—CH₂—CH₂—CH(CH₃)—CH₃ | X₁₃—Cl | | Cl—X₁₅ | |
| 287 | | H₃C—O—X₁₁ | H₃C—(CH₂)₄—X₁₂ | X₁₃—Cl | | Cl—X₁₅ | |

-continued
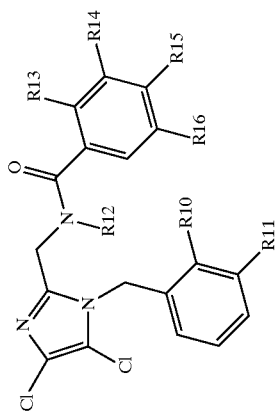
| Ex # | R10 | R11 | R12 | R13 | R14 | R15 | R16 |
|---|---|---|---|---|---|---|---|
| 288 | X10—O—CH3 | | X12—CH2CH2—CH(CH3)—CH3 (with H3C) | | | Cl—X15 | |
| 289 | | X10—O—CH3 | H3C—CH2CH2CH2CH2—X12 | | | H3C—(CH2)4—X15 | |
| 290 | | H3C—O—X11 | X12—CH2CH2—CH(CH3)—CH3 (with H3C) | | | H3C—(CH2)4—X15 | |

-continued
| Ex # | R10 | R11 | R12 | R13 | R14 | R15 | R16 |
|---|---|---|---|---|---|---|---|
| 291 | | H3C-O-X11 | H3C~~~X12 | | | H3C~~~X15 | |
| 292 | X10-O-CH3 | | X12-CH(CH3)-CH2-CH2- (H3C)  | | | H3C~~~X15 | |
| 293 | X10-O-CH3 | | H3C~~~X12 | | | H3C~~~O-X15 | |
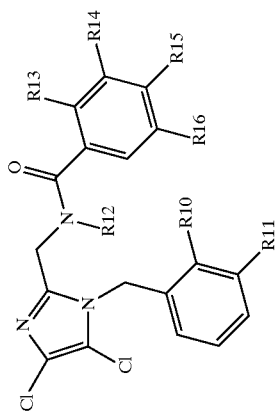

| Ex # | R10 | R11 | R12 | R13 | R14 | R15 | R16 |
|---|---|---|---|---|---|---|---|
| 294 | | H3C-O-X11 | X12-CH2-CH2-CH(CH3)-CH3 | | | H3C-CH2-CH2-O-X15 | |
| 295 | | H3C-O-X11 | H3C-CH2-CH2-CH2-CH2-X12 | | | H3C-CH2-CH2-O-X15 | |
| 296 | X10-O-CH3 | | X12-CH2-CH2-CH(CH3)-CH3 | | | H3C-CH2-CH2-O-X15 | |
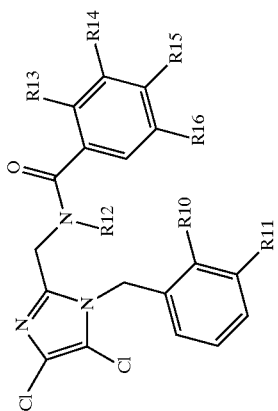

-continued
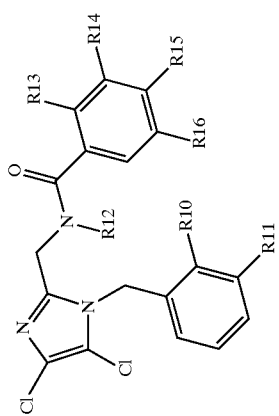
| Ex # | R10 | R11 | R12 | R13 | R14 | R15 | R16 |
|---|---|---|---|---|---|---|---|
| 297 | H3C—O—X10 | | H3C~~~X12 | | | X15-phenyl | |
| 298 | | H3C—O—X11 | X12~CH(CH3)CH2CH2 | | | X15-phenyl | |
| 299 | | H3C—O—X11 | H3C~~~X12 | | | X15-phenyl | |

| Ex # | R10 | R11 | R12 | R13 | R14 | R15 | R16 |
|---|---|---|---|---|---|---|---|
| 300 | X₁₀–O–CH₃ | | X₁₂–CH₂CH₂–CH(CH₃)–CH₃ (H₃C, X₁₂ branched) | | | phenyl-X₁₅ | |
| 301 | | X₁₀–O–CH₃ (H₃C-O-X₁₀) | H₃C–CH₂CH₂CH₂CH₂–X₁₂ | phenyl-X₁₃ | | | |
| 302 | | H₃C–O–X₁₁ | X₁₂–CH₂CH₂–CH(CH₃)–CH₃ | phenyl-X₁₃ | | | |
| 303 | | H₃C–O–X₁₁ | H₃C–CH₂CH₂CH₂CH₂–X₁₂ | phenyl-X₁₃ | | | |

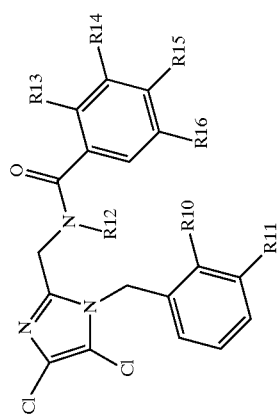
| Ex # | R10 | R11 | R12 | R13 | R14 | R15 | R16 |
|---|---|---|---|---|---|---|---|
| 304 | X10—O—CH3 | | X12—CH2CH2—CH(CH3)—CH3 (H3C) | | | | |
| 305 | X10—O—CH3 | | H3C—CH2CH2CH2CH2—X12 | | | | |
| 306 | | H3C—O—X11 | X12—CH2CH2—CH(CH3)—CH3 (H3C) | X13—Ph | X14—Br | | |

-continued
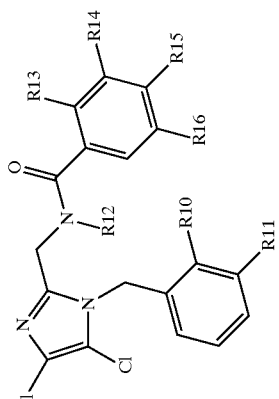
| Ex # | R10 | R11 | R12 | R13 | R14 | R15 | R16 |
|---|---|---|---|---|---|---|---|
| 307 | | H₃C-O-X₁₁ | H₃C~~~X₁₂ | | X₁₄-Br | | |
| 308 | X₁₀-O-CH₃ | | X₁₂-CH(CH₃)-CH₂-CH₂- with CH₃ | | X₁₄-Br | | |
| 309 | X₁₀-O-CH₃ | | H₃C~~~X₁₂ | | | Br-X₁₅ | |

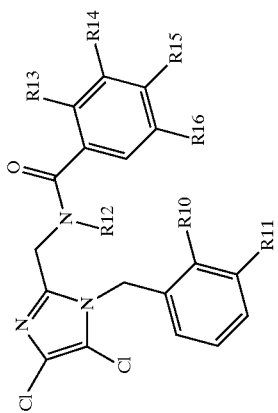
| Ex # | R10 | R11 | R12 | R13 | R14 | R15 | R16 |
|---|---|---|---|---|---|---|---|
| 310 | | H3C-O-X11 | X12-CH(CH3)-CH2-CH2- (H3C-CH(CH3)-CH2-CH2-X12) | | | Br—X15 | |
| 311 | | H3C-O-X11 | H3C-(CH2)4-X12 | | | Br—X15 | |
| 312 | X10-O-CH3 | | X12-CH(CH3)-CH2-CH2- (H3C-CH(CH3)-CH2-CH2-X12) | | | Br—X15 | |

-continued

| Ex # | R10 | R11 | R12 | R13 | R14 | R15 | R16 |
|---|---|---|---|---|---|---|---|
| 313 | H₃C—X₁₀ | | H₃C~~~X₁₂ | X₁₃—Br | | | |
| 314 | | H₃C—O—X₁₁ | X₁₂CH(CH₃)CH₂ | X₁₃—Br | | | |
| 315 | | H₃C—O—X₁₁ | H₃C~~~X₁₂ | X₁₃—Br | | | |

-continued
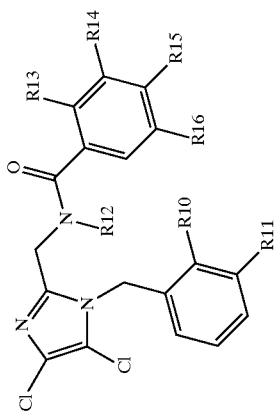
| Ex # | R10 | R11 | R12 | R13 | R14 | R15 | R16 |
|---|---|---|---|---|---|---|---|
| 316 | X10—O—CH3 | | X12—CH2CH2—CH(CH3)—CH3 (H3C) | X13—Br | | X15—(CH2)5—CH3 | |
| 317 | X10—O—CH3 | | H3C—(CH2)4—X12 | | | X15—(CH2)5—CH3 | |
| 318 | | H3C—O—X11 | X12—CH2CH2—CH(CH3)—CH3 (H3C) | | | | |

-continued
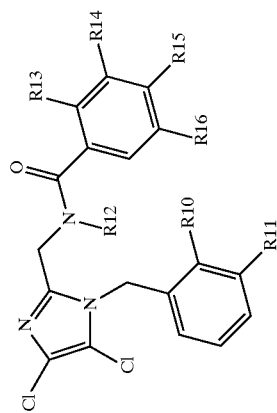
| Ex # | R10 | R11 | R12 | R13 | R14 | R15 | R16 |
|---|---|---|---|---|---|---|---|
| 319 | | H3C—O—X11 | H3C~~~~X12 | | | H3C~~~~X15 | |
| 320 | X10—O—CH3 | | X12~~CH(CH3)~ | | | H3C~~~~X15 | |
| 321 | X10—O—CH3 | | H3C~~~~X12 | | | F3C—O—X15 | |

| Ex # | R10 | R11 | R12 | R13 | R14 | R15 | R16 |
|------|-----|-----|-----|-----|-----|-----|-----|
| 322 |  | H₃C–O–X₁₁ | X₁₂–CH₂–CH₂–CH(CH₃)–CH₃ |  |  | F₃C–O–X₁₅ |  |
| 323 |  | H₃C–O–X₁₁ | H₃C–CH₂–CH₂–CH₂–CH₂–X₁₂ |  |  | F₃C–O–X₁₅ |  |
| 324 | X₁₀–O–CH₃ |  | X₁₂–CH₂–CH₂–CH(CH₃)–CH₃ |  |  | F₃C–O–X₁₅ |  |

-continued
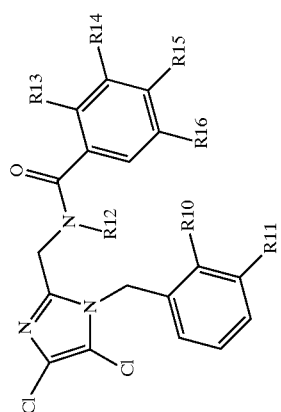
| Ex # | R10 | R11 | R12 | R13 | R14 | R15 | R16 |
|---|---|---|---|---|---|---|---|
| 325 | X10—O—CH3 | | H3C~~~X12 | | | | |
| 326 | | H3C—O—X11 | X12-CH(CH3)-CH2-CH2- with H3C | | | O—X15 with H3C chain | |
| 327 | | H3C—O—X11 | H3C~~~X12 | | | O—X15 with H3C chain | |

| Ex # | R10 | R11 | R12 | R13 | R14 | R15 | R16 |
|---|---|---|---|---|---|---|---|
| 328 | X10—O—CH3 | | X12—CH2CH2—CH(CH3)—CH3 | | | | |
| 329 | X10—O—CH3 | | H3C—CH2CH2CH2CH2—X12 | X13—F | X14—CF3 | O—X15 (—CH2CH2CH2—CH3) | |
| 330 | | H3C—O—X11 | X12—CH2CH2—CH(CH3)—CH3 | X13—F | X14—CF3 | | |

-continued
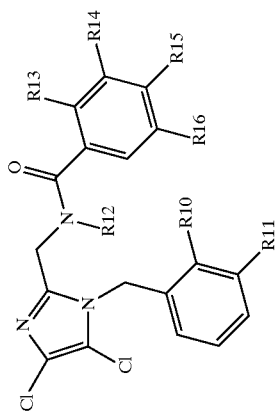
| Ex # | R10 | R11 | R12 | R13 | R14 | R15 | R16 |
|---|---|---|---|---|---|---|---|
| 331 | | H3C-O-X11 | H3C-(CH2)4-X12 | X13-F | X14-CF3 | | |
| 332 | X10-O-CH3 | | X12-CH2-CH2-CH(CH3)-CH3 | F-X13 | F-CF2-X14 | | |
| 333 | X10-O-CH3 | | H3C-(CH2)4-X12 | | H3C-O-CH2-X14 | H3C-O-CH2-X15 | |

-continued
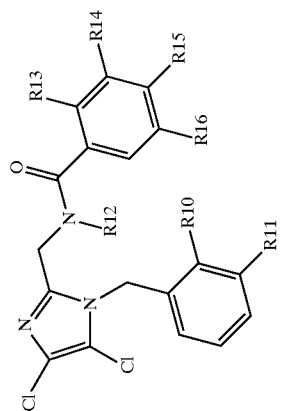
| Ex # | R10 | R11 | R12 | R13 | R14 | R15 | R16 |
|---|---|---|---|---|---|---|---|
| 334 | | H3C—O—X11 | X12—CH2CH2—CH(CH3)— (H3C) | | H3C—O—X14 | H3C—O—X15 | |
| 335 | | H3C—O—X11 | H3C—CH2CH2CH2CH2—X12 | | H3C—O—X14 | H3C—O—X15 | |
| 336 | X10—O—CH3 | | X12—CH2CH2—CH(CH3)— (H3C) | | H3C—O—X14 | H3C—O—X15 | |

-continued
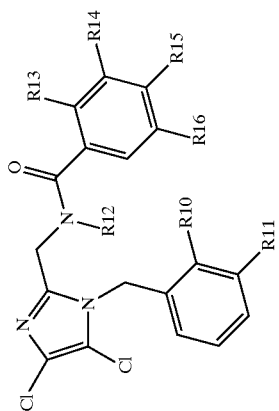
| Ex # | R10 | R11 | R12 | R13 | R14 | R15 | R16 |
|---|---|---|---|---|---|---|---|
| 337 | H₃C—O—X₁₀ | | H₃C⎯⎯⎯⎯X₁₂ | | CH₃—O—X₁₄ | H₃C—O—X₁₅ | H₃C—O—X₁₆ |
| 338 | | H₃C—O—X₁₁ | X₁₂⎯⎯CH(CH₃)⎯⎯ | | CH₃—O—X₁₄ | H₃C—O—X₁₅ | H₃C—O—X₁₆ |
| 339 | | H₃C—O—X₁₁ | H₃C⎯⎯⎯⎯X₁₂ | | CH₃—O—X₁₄ | H₃C—O—X₁₅ | H₃C—O—X₁₆ |

-continued
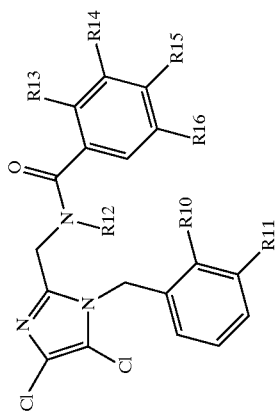
| Ex # | R10 | R11 | R12 | R13 | R14 | R15 | R16 |
|---|---|---|---|---|---|---|---|
| 340 | X₁₀—O—CH₃ | | X₁₂—CH₂CH₂—CH(CH₃)—CH₃ | | CH₃—O—X₁₄ | H₃C—O—X₁₅ | H₃C—O—X₁₆ |
| 341 | X₁₀—O—CH₃ | | H₃C—CH₂CH₂CH₂CH₂—X₁₂ | X₁₃—O—CH₃ | H₃C—O—X₁₄ | H₃C—O—X₁₅ | |
| 342 | | H₃C—O—X₁₁ | X₁₂—CH₂CH₂—CH(CH₃)—CH₃ | H₃C—O—X₁₃ | H₃C—O—X₁₄ | H₃C—O—X₁₅ | |

-continued
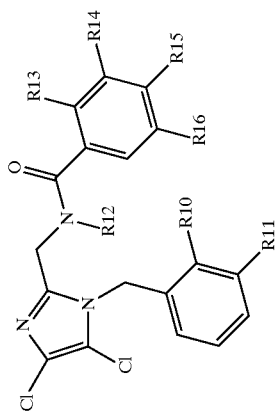
| Ex # | R10 | R11 | R12 | R13 | R14 | R15 | R16 |
|---|---|---|---|---|---|---|---|
| 343 | | H₃C—O—X₁₁ | H₃C~~~X₁₂ | X₁₃—O—CH₃ | H₃C—O—X₁₄ | H₃C—O—X₁₅ | |
| 344 | X₁₀—O—CH₃ | | X₁₂–CH(CH₃)–CH₂–CH₃ | H₃C—O—X₁₃ | H₃C—O—X₁₄ | H₃C—O—X₁₅ | |
| 345 | X₁₀—O—CH₃ | | H₃C~~~X₁₂ | X₁₃—CH₂—C₆H₅ | | | |

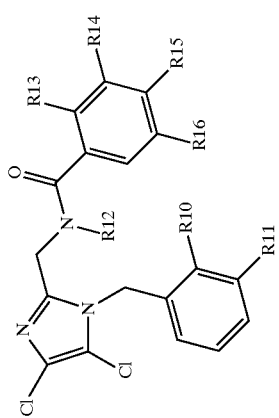
| Ex # | R10 | R11 | R12 | R13 | R14 | R15 | R16 |
|---|---|---|---|---|---|---|---|
| 346 | | H₃C-O-X₁₁ | X₁₂-CH₂-CH₂-CH(CH₃)-CH₃ | Ph-CH₂-X₁₃ | | | |
| 347 | | H₃C-O-X₁₁ | H₃C-(CH₂)₄-X₁₂ | X₁₃-CH₂-Ph | | | |
| 348 | X₁₀-O-CH₃ | | X₁₂-CH₂-CH₂-CH(CH₃)-CH₃ | Ph-CH₂-X₁₃ | | | |

-continued
| Ex # | R10 | R11 | R12 | R13 | R14 | R15 | R16 |
|---|---|---|---|---|---|---|---|
| 349 | 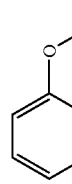 | | 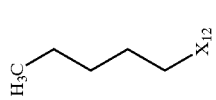 | | | 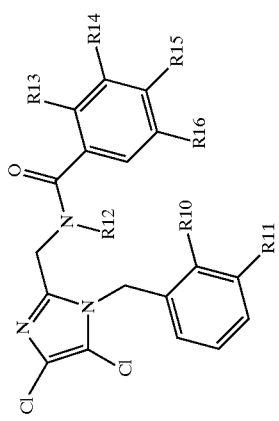 | |
| 350 | | 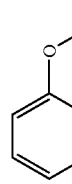 |  | | | 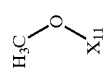 | |
| 351 | | 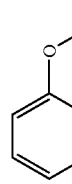 | 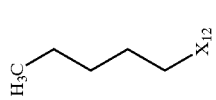 | | | 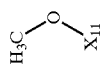 | |

-continued
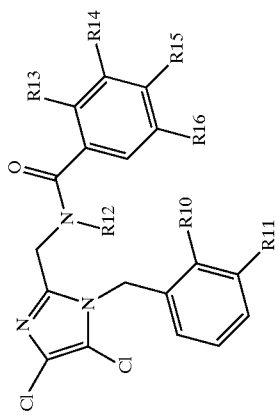
| Ex # | R10 | R11 | R12 | R13 | R14 | R15 | R16 |
|---|---|---|---|---|---|---|---|
| 352 | X₁₀—O—CH₃ | | X₁₂—CH₂CH₂—CH(CH₃)—CH₃ | | | O—X₁₄ (phenyl) | |
| 353 | X₁₀—O—CH₃ | | H₃C—(CH₂)₄—X₁₂ | | | | O—X₁₅ (phenyl) |
| 354 | | H₃C—O—X₁₁ | X₁₂—CH₂CH₂—CH(CH₃)—CH₃ | | | | O—X₁₅ (phenyl) |

-continued
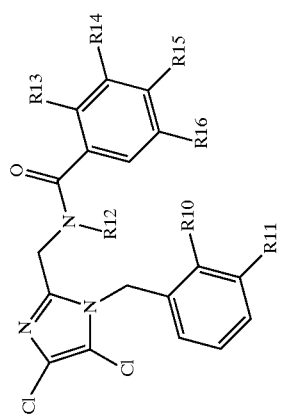
| Ex # | R10 | R11 | R12 | R13 | R14 | R15 | R16 |
|---|---|---|---|---|---|---|---|
| 355 | 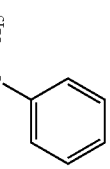 | 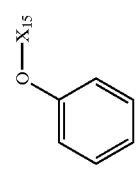 | 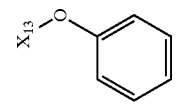 | | | 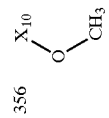 | |
| 356 | 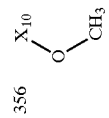 | | 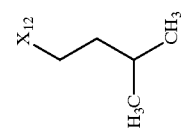 | 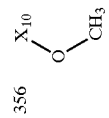 | | 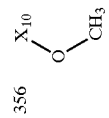 | |
| 357 | 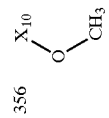 | | 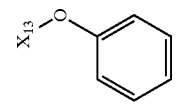 | | | | |

-continued
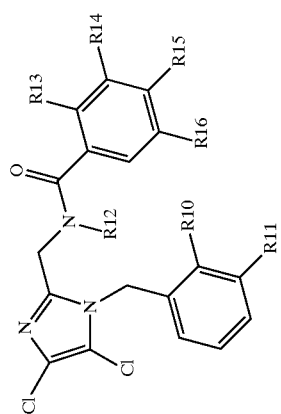
| Ex # | R10 | R11 | R12 | R13 | R14 | R15 | R16 |
|---|---|---|---|---|---|---|---|
| 358 | | H₃C-O-X₁₁ | X₁₂-CH₂-CH₂-CH(CH₃)-CH₃ (H₃C branch) | phenyl-O-X₁₃ | | | |
| 359 | | H₃C-O-X₁₁ | H₃C-(CH₂)₄-X₁₂ | phenyl-O-X₁₃ | | | |
| 360 | X₁₀-O-CH₃ | | X₁₂-CH₂-CH₂-CH(CH₃)-CH₃ | phenyl-O-X₁₃ | | | |

-continued

[Structure: benzamide with R13, R14, R15, R16 substituents on phenyl; N-R12 amide; CH2 connected to imidazole bearing two Cl; N-CH2-phenyl with R10, R11]

| Ex # | R10 | R11 | R12 | R13 | R14 | R15 | R16 |
|---|---|---|---|---|---|---|---|
| 361 | X₁₀—O—CH₃ | | H₃C—(CH₂)₄—X₁₂ | | Br—X₁₄ | H₃C—X₁₅ | |
| 362 | | H₃C—O—X₁₁ | X₁₂—CH₂CH₂—CH(CH₃)—CH₃ | | Br—X₁₄ | H₃C—X₁₅ | |
| 363 | | H₃C—O—X₁₁ | H₃C—(CH₂)₄—X₁₂ | | Br—X₁₄ | H₃C—X₁₅ | |

-continued
| Ex # | R10 | R11 | R12 | R13 | R14 | R15 | R16 |
|---|---|---|---|---|---|---|---|
| 364 | X10—O—CH3 | | X12—CH2CH2—CH(CH3)—CH3 (H3C, CH3) | | Br—X14 | H3C—X15 | |
| 365 | X10—O—CH3 | | H3C—CH2CH2CH2CH2—X12 | | Br—X14 | F—X15 | |
| 366 | | H3C—O—X11 | X12—CH2CH2—CH(CH3)—CH3 | | Br—X14 | F—X15 | |
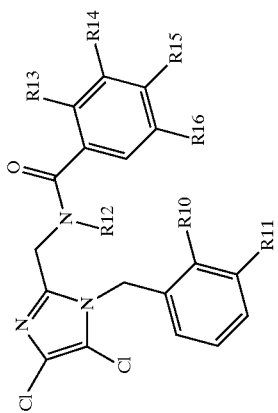

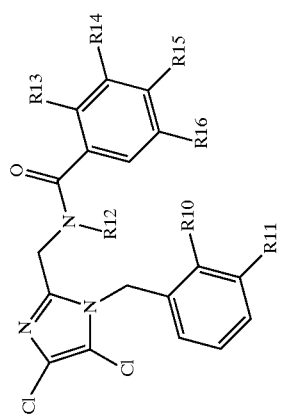
| Ex # | R10 | R11 | R12 | R13 | R14 | R15 | R16 |
|---|---|---|---|---|---|---|---|
| 367 | | H3C-O-X11 | H3C~~~X12 | | Br-X14 | F-X15 | |
| 368 | X10-O-CH3 | | X12~~CH(CH3)~~ | | Br-X14 | F-X15 | |
| 369 | X10-O-CH3 | | H3C~~~X12 | | | H3C~~~~~~X15 | |

-continued
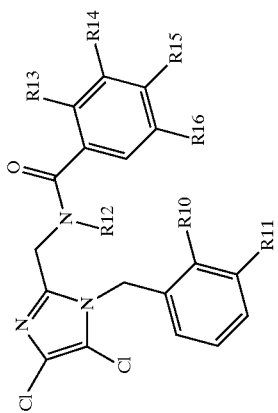
| Ex # | R10 | R11 | R12 | R13 | R14 | R15 | R16 |
|---|---|---|---|---|---|---|---|
| 370 | | H3C–O–X11 | X12–CH2CH2–CH(CH3)–CH3 | | | H3C–(CH2)6–X15 | |
| 371 | | H3C–O–X11 | H3C–(CH2)4–X12 | | | H3C–(CH2)6–X15 | |
| 372 | X10–O–CH3 | | X12–CH2CH2–CH(CH3)–CH3 | | | H3C–(CH2)6–X15 | |

-continued
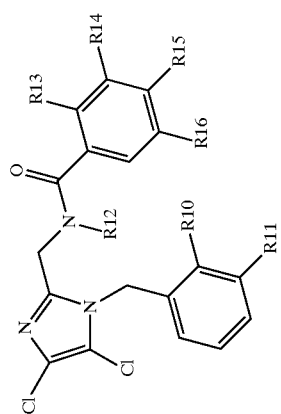
| Ex # | R10 | R11 | R12 | R13 | R14 | R15 | R16 |
|---|---|---|---|---|---|---|---|
| 373 | H₃C—X₁₀ | | H₃C~~~X₁₂ | | | | |
| 374 | | H₃C—O—X₁₁ | X₁₂~~CH(CH₃)~CH₃ | | | H₃C~~~~~O—X₁₅ | |
| 375 | | H₃C—O—X₁₁ | H₃C~~~~X₁₂ | | | H₃C~~~~~O—X₁₅ | |

-continued
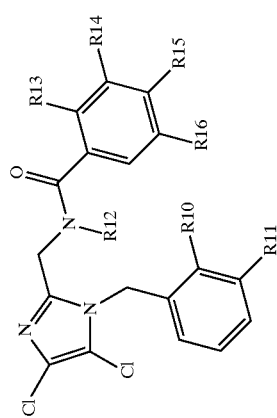
| Ex # | R10 | R11 | R12 | R13 | R14 | R15 | R16 |
|---|---|---|---|---|---|---|---|
| 376 | X10—O—CH3 | | X12—CH2CH2CH(CH3)—CH3 | | | | |
| 377 | X10—O—CH3 | | H3C—(CH2)4—X12 | Ph—CH2CH2—X13 | | | |
| 378 | | H3C—O—X11 | X12—CH2CH2CH(CH3)—CH3 | Ph—CH2CH2—X13 | | H3C—(CH2)4—O—X15 | |

| Ex # | R10 | R11 | R12 | R13 | R14 | R15 | R16 |
|---|---|---|---|---|---|---|---|
| 379 | | H3C-O-X11 | H3C~~~X12 | | | | |
| 380 | X10-O-CH3 | | X12~CH(CH3)~ | X13-CH2CH2-Ph | | | |
| 381 | X10-O-CH3 | | H3C~~~X12 | Ph-CH2CH2-X13 | | H3C~~~~~~X15 | |

-continued
| Ex # | R10 | R11 | R12 | R13 | R14 | R15 | R16 |
|---|---|---|---|---|---|---|---|
| 382 | | H₃C-O-X₁₁ | X₁₂-CH₂CH₂-CH(CH₃)-CH₃ | | | H₃C-(CH₂)₆-X₁₅ | |
| 383 | | H₃C-O-X₁₁ | H₃C-(CH₂)₄-X₁₂ | | | H₃C-(CH₂)₆-X₁₅ | |
| 384 | X₁₀-O-CH₃ | | X₁₂-CH₂CH₂-CH(CH₃)-CH₃ | | | H₃C-(CH₂)₆-X₁₅ | |
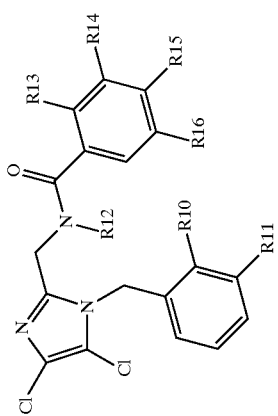

-continued
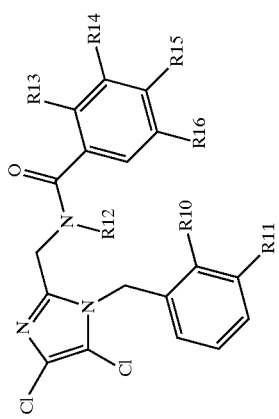
| Ex # | R10 | R11 | R12 | R13 | R14 | R15 | R16 |
|---|---|---|---|---|---|---|---|
| 385 | CH3–X10 | | H3C~~~X12 | | | H3C~~~O–X15 | |
| 386 | | H3C–O–X11 | X12–CH(CH3)–CH2–CH2– with H3C | | | H3C~~~O–X15 | |
| 387 | | H3C–O–X11 | H3C~~~X12 | | | H3C~~~O–X15 | |

-continued
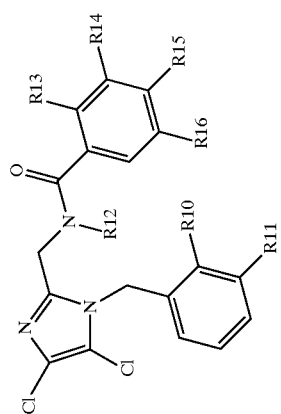
| Ex # | R10 | R11 | R12 | R13 | R14 | R15 | R16 |
|---|---|---|---|---|---|---|---|
| 388 | X10—O—CH3 | | X12—CH2CH2—CH(CH3)—CH3 | | | | |
| 389 | X10—O—CH3 | | H3C—CH2CH2CH2CH2—X12 | | X14—I | | |
| 390 | X10—O—CH3 | H3C—O—X11 | X12—CH2CH2—CH(CH3)—CH3 | | X14—I | O—X15 (with pentyl chain ending H3C) | |

-continued
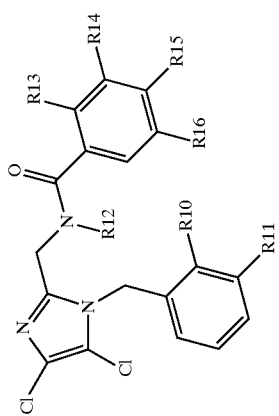
| Ex # | R10 | R11 | R12 | R13 | R14 | R15 | R16 |
|---|---|---|---|---|---|---|---|
| 391 | H3C—O—X11 | | H3C~~~X12 | | X14—I | | |
| 392 | X10—O—CH3 | | X12-CH(CH3)-CH2-CH2 | | X14—I | | |
| 393 | X10—O—CH3 | | H3C~~~X12 | | | I—X15 | |

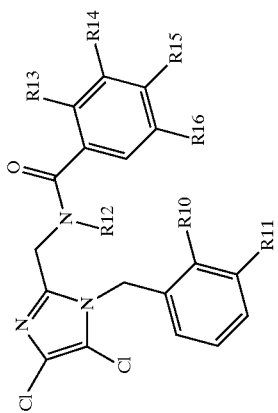
| Ex # | R10 | R11 | R12 | R13 | R14 | R15 | R16 |
|---|---|---|---|---|---|---|---|
| 394 | | H$_3$C—O—X$_{11}$ | X$_{12}$—CH(CH$_3$)—CH$_3$ (H$_3$C) | | | I—X$_{15}$ | |
| 395 | | H$_3$C—O—X$_{11}$ | H$_3$C—(CH$_2$)$_4$—X$_{12}$ | | | I—X$_{15}$ | |
| 396 | X$_{10}$—O—CH$_3$ | | X$_{12}$—CH(CH$_3$)—CH$_3$ (H$_3$C) | | | I—X$_{15}$ | |

-continued
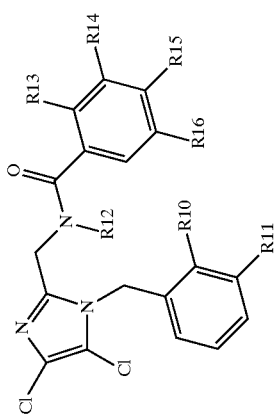
| Ex # | R10 | R11 | R12 | R13 | R14 | R15 | R16 |
|---|---|---|---|---|---|---|---|
| 397 | H3C—O—X10 | | H3C—(CH2)4—X12 | X13—I | | | |
| 398 | | H3C—O—X11 | X12—CH2CH2—CH(CH3) | X13—I | | | |
| 399 | | H3C—O—X11 | H3C—(CH2)4—X12 | X13—I | | | |

-continued
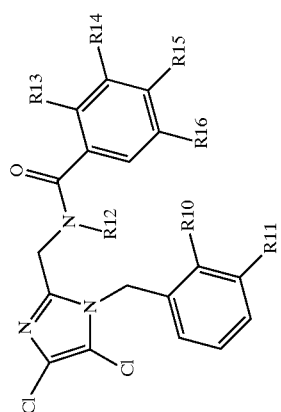
| Ex # | R10 | R11 | R12 | R13 | R14 | R15 | R16 |
|---|---|---|---|---|---|---|---|
| 400 | X10—O—CH3 | | X12-CH2CH2-CH(CH3)-CH3 (with CH3 branch) | | | | |
| 401 | X10—O—CH3 | | H3C-CH2CH2CH2CH2-X12 | I—X13 | | | |
| 402 | X10—O—CH3 | H3C—O—X11 | X12-CH2CH2-CH(CH3)-CH3 | | | O—X15 (heptyl chain) | |

-continued
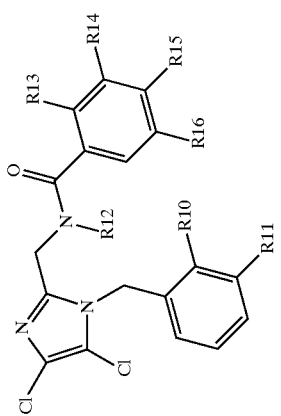
| Ex # | R10 | R11 | R12 | R13 | R14 | R15 | R16 |
|---|---|---|---|---|---|---|---|
| 403 | | H3C-O-X11 | H3C~~~X12 | | | H3C~~~~~O-X15 | |
| 404 | X10-O-CH3 | | X12~~CH(CH3)-CH3 | | | H3C~~~~~O-X15 | |

Example 8

Ligand Binding Assay on Sf9 cell membranes expressing the BK-2 receptor

This assay is used to determine the high affinity of compounds of this invention for the BK-2 (bradykinin $B_2$) receptor.

Binding Buffer: 50 mM Tris 7.0 (cold), 0.14 grams per liter bacitracin (approx. 50,000 units of activity/liter, lot# 103746 from Amersham), and $10^{-6}$ M captopril. Captopril is purchased from Sigma C-4042, 2.17 mg in 10 ml of milli-Q water produces a $10^{-3}$ M stock. Stock can be stored for 3 weeks in the refrigerator. 1.0 ml of stock per liter buffer= $10^{-6}$ M final concentration.

Ligand Preparation: 0.25 nM $^3$H-Bradykinin is used. 10 µl of stock+100 ml of binding buffer gives approximately 600 cpm/5 µl aliquot.

Non-Specific Preparation: NS binding is defined by unlabeled bradykinin at 1 µM final concentration. Aliquots are stored at −20 ° C. in 0.5% BSA at a concentration of $10^{-3}$ M. Aliquots are then diluted 1:100 for an intermediate concentration of $10^{-5}$ M.

Baculovirus-infected Sf9 cells expressing recombinant human bradykinin $B_2$ receptors are harvested 48 hours post infection via centrifugation at 3000×g. Cells are washed with ice-cold PBS and stored at −70° C. until needed. Frozen cell pellets are resuspended in ice cold Washing Buffer (50 mM Tris pH 7.0) and homogenized via POLYTRON for 30 seconds at setting 5. Membranes are centrifuged at 40,000×g for 10 min. Pellets are resuspended in Washing Buffer with the aid of a polytron and centrifuged again. Membranes are resuspended in binding buffer at a concentration of 133 µg/ml. This corresponds to 20 µg of protein per 150 µl.

When measuring non-specific binding, incubations contain 150 µl of Sf9 cell membranes, prepared as described above, 50 µl $^3$H-Bradykinin (0.25 nM), 25 µl unlabeled bradykinin at 1 µM final concentration and 2 µl DMSO. Incubations for determining test compound binding contain 175 µl of Sf9 cell membranes, 50 µl $^3$H-Bradykinin (0.25 nM), and test compound in 2 µl DMSO. The concentration of the test compound is generally 1 µM for displacement studies. The binding reaction components are incubated for 2 hrs at 4° C. in Falcon U bottom plates. Plates are harvested on the microbeta harvester onto 0.5% PEI pretreated unifilters. After harvesting, the filters are dried overnight. 17 µl of beta-scint is added to each well before the unifilters are counted in the microbeta counters. Data are collected in duplicate determinations, averaged and % inhibition of total specific binding is calculated. Total Specific Binding=Total−Nonspecific. In some cases, the amounts of unlabeled drug is varied and total displacement curves of binding are carried out. Data are converted to a form for the calculation of $IC_{50}$ and Hill Coefficient (nH). Ki's are subsequently determined by the Cheng-Prusoff equation (Cheng, Y. C.; Prusoff, W. C. Biochem. Pharmacol. 1972, 22, 3099–3108). In the described assay, preferred compounds of the invention have Ki's of less than 1 µM, more preferred compounds of the invention exhibit Ki values of less than 500 nM and even more preferred compounds of the invention exhibit Ki values of less than 100 nM.

Example 9

BK-2 Receptor Mediated Calcium Mobilization

The agonist and antagonist properties of the compounds of the invention can be evaluated by the following assay.

CHO cells stably expressing the BK-2 receptor are grown in Ham's F-12 media supplemented with 250 µg/ml G418, 1 µg/ml tetracycline, 7 µg/ml puromycin, 10% fetal bovine serum and 25 mM Hepes, pH=7.4. Forty eight hours prior to assay, the cell growth media is replaced with another medium that does not contain the tetracycline. Twenty four hours prior to experiment sodium butyrate is added to a final concentration of 10 mM. On the day of assay, cells, grown to 70–90% confluency in 96-well plates, are washed with Krebs-Ringer buffer (25 mM HEPES, 5 mM KCl, 0.96 mM $NaH_2PO_4$, 1 mM $MgSO_4$, 2 mM $CaCl_2$, 5 mM glucose, and 1 mM probenecid, pH 7.4) and are then incubated for 1–2 hours in the above buffer supplemented with Fluo3-AM (2.5 n 10 (g/ml; Teflabs) at 37° C. in an environment containing 5% $CO_2$. The wells are then washed twice with Krebs-Ringers buffer. Agonist-induced (bradykinin) calcium mobilization is monitored using either Fluoroskan Ascent (Labsystems) or FLIPR (Molecular Devices) instruments. The agonists, either bradykinin or drug candidates, are added to the cells and fluorescence responses are continuously recorded for up to 5 min. For the examination of antagonist drug candidates, compounds, at a concentration of 1 µM in DMSO, are preincubated with the cells for up to 30 minutes prior to administration of the bradykinin agonist. Bradykinin agonist is generally applied at a concentration sufficient to induce 50% maximal activity. Responses are recorded for up to 5 min. Kaleidagraph software (Synergy Software, Reading, Pa.) is utilized to fit the data to the equation y=a*(1/(1+(b/x)c)) to determine the $EC_{50}$ value or $IC_{50}$ value for the response. In this equation, y is the maximum fluorescence signal, x is the concentration of the agonist or antagonist, a is the Emax, b corresponds to the $EC_{50}$ or $IC_{50}$ value, and, finally, c is the Hill coefficient.

Example 10

Preparation of Radiolabeled Probe Compounds of the Invention

The compounds of the invention are prepared as radiolabeled probes by carrying out their synthesis using precursors comprising at least one atom that is a radioisotope. The radioisotope is preferably selected from of at least one of carbon (preferably $^{14}$C), hydrogen (preferably $^3$H), sulfur (preferably $^{35}$S), or iodine (preferably $^{125}$I). Such radiolabeled probes are conveniently synthesized by a radioisotope supplier specializing in custom synthesis of radiolabeled probe compounds. Such suppliers include Amersham Corporation, Arlington Heights, Ill.; Cambridge Isotope Laboratories, Inc. Andover, Mass.; SRI International, Menlo Park, Calif.; Wizard Laboratories, West Sacramento, Calif.; ChemSyn Laboratories, Lexena, Kans.; American Radiolabeled Chemicals, Inc., St. Louis, Mo.; and Moravek Biochemicals Inc., Brea, Calif.

Tritium labeled probe compounds are also conveniently prepared catalytically via platinum-catalyzed exchange in tritiated acetic acid, acid-catalyzed exchange in tritiated trifluoroacetic acid, or heterogeneous-catalyzed exchange with tritium gas. Such preparations are also conveniently carried out as a custom radiolabeling by any of the suppliers listed in the preceding paragraph using the compound of the invention as substrate. In addition, certain precursors may be subjected to tritium-halogen exchange with tritium gas, tritium gas reduction of unsaturated bonds, or reduction using sodium borotritide, as appropriate.

Example 11

Use of Compounds of the Invention as Probes for BK-2 Receptors in Cultured Cells and Tissue Samples The presence of BK-2 receptors in cultured cells or tissue samples may be ascertained by the procedures described by Hall and Morton in the chapter entitled "Immunopharmacology of the Bradykinin Receptor" of The Handbook of Immunopharmacology—The Kinin Systems (1997) Academic Press, S. C. Fanner, editor, using radiolabeled compounds of the invention prepared as described in the preceding Example 9.

The invention and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the spirit or scope of the present invention as set forth in the claims. To particularly point out and distinctly claim the subject matter regarded as invention, the following claims conclude this specification.

What is claimed is:

1. A compound of the formula

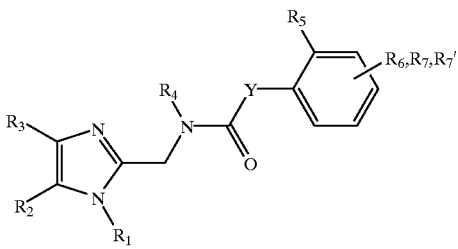

or a pharmaceutically acceptable salt, prodrug, or solvate thereof, wherein:

$R_1$ is arylalkyl which is optionally substituted directly or through a $O(CH_2)_n$ linker (where n=1, 2, 3 or 4) with up to three substituents independently selected from:
(i) halogen nitro, trifluoromethyl, trifluoromethoxy, cyano, hydroxyl, $C_1-C_6$ alkyl, amino, $C_1-C_6$ alkoxy, aminomethyl, mono or di($C_1-C_6$)alkylamino, mono or dialkylaminomethyl, (wherein each alkyl is independently lower ($C_1-C_6$) alkyl),
(ii) $C_1-C_6$alkoxyNR$_8$R$_9$, NR$_8$R$_9$, NR$_8$COR$_9$, CONR$_8$R$_9$, wherein $R_8$ and $R_9$ are the same or different and represent hydrogen, straight or branched chain lower alkyl,
(iii) $O(CH_2)_nCO_2R_A$ wherein n=1,2,3,4, COR$_A$, and CO$_2$R$_A$, wherein $R_A$ represents hydrogen or straight chain lower alkyl,
(iv) SO$_2$R$_A$, NHSO$_2$R$_A$, SO$_2$NHR$_A$, SO$_2$NHCOR$_A$, and CONHSO$_2$R$_A$, wherein $R_A$ represents hydrogen or straight chain lower alkyl,
with the proviso that $R_1$ may not be 3-Fluorobenzyl;
$R_2$ and $R_3$ are the same or different and represent
(i) halogen, trifluoromethyl, trifluoromethoxy, lower alkoxy having 1–6 carbon atoms, lower alkyl, amino methyl, mono or dialkylaminomethyl, wherein each alkyl is independently lower ($C_1-C_6$) alkyl,
(ii) $C_1-C_6$alkoxyNR$_8$'R$_9$', NR$_8$'R$_9$', CONR$_8$'R$_9$', NR$_8$'COR$_9$', wherein $R_8$' and $R_9$' are the same or different and represent hydrogen or straight or branched chain lower alkyl,
(iii) $O(CH_2)_nCO_2R_A$' where n=1,2,3,4, COR$_A$', or CO$_2$R$_A$', wherein $R_A$' represents hydrogen or straight chain lower alkyl;
$R_4$ represents straight or branched chain lower alkyl;
$R_5$ represents halogen or trifluoromethyl;
$R_6$, $R_7$ and $R_7$' are the same or different and represent
(i) hydrogen, trifluoromethyl, trifluoromethoxy, nitrile, $C_1-C_{10}$ alkyl, $C_1-C_{10}$ alkoxy (with the proviso that $R_6$, $R_7$, or $R_7$' may not be $C_1-C_{10}$ alkoxy when located ortho to Y), $C_1-C_6$alkylthio, halogen, aminomethyl, di($C_1-C_6$)alkylamino, mono or di$C_1-C_6$alkylaminomethyl, or
(ii) $C_1-C_6$ alkoxyaminoalkyl where the amino is mono or disubstituted with straight or branched chain lower alkyl;
(iii) or any two adjacent $R_6$, $R_7$ or $R_7$' may be joined to form a 5 to 7 membered carbocyclic ring; or $R_5$ and $R_6$ are joined to form a 6 membered carbocyclic aromatic ring which is optionally substituted with up to four substituents selected from:
(i) halogen, nitro, trifluoromethyl, cyano, hydroxyl, $C_1-C_6$ alkyl, amino, $C_1-C_6$ alkoxy, aminomethyl, alkylaminomethyl, mono or di($C_1-C_6$) alkylamino, mono or dialkylaminomethyl, wherein each alkyl is independently lower ($C_1-C_6$) alkyl,
(ii) $C_1-C6$alkoxyNR$_8$"R$_9$", NR$_8$"R$_9$", CONR$_8$"R$_9$", NR$_8$"COR$_9$", where $R_8$" and $R_9$" are the same or different and represent hydrogen or straight or branched chain lower alkyl,
(iii) $O(CH_2)_nCO_2R_A$" where n=1,2,3,4, COR$_A$", or CO$_2$R$_A$", wherein $R_A$" represents hydrogen or straight chain lower alkyl; and $R_7$ and $R_7$' are as defined above; and Y represents a bond or CH$_2$, when Y=CH$_2$ it may be mono or disubstituted with a straight or branched chain lower alkyl, or straight or branched chain lower alkoxy having 1–6 carbon atoms.

2. A compound of the formula

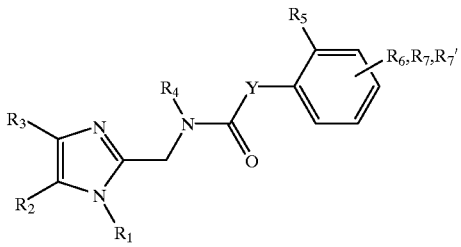

or a pharmaceutically acceptable salt, prodrug, or solvate thereof, wherein:

$R_1$ is benzyl, each of which is optionally substituted directly or through a $O(CH_2)_n$ linker (where n=1,2,3 or 4) with up to three substituents independently selected from:
(i) halogen (with the proviso that $R_1$ may not be 3-Fluorobenzyl), nitro, trifluoromethyl, trifluoromethoxy, cyano, hydroxyl, $C_1-C_6$ alkyl, amino, $C_1-C_6$ alkoxy, aminomethyl, mono or di($C_1-C_6$)alkylamino, mono or dialkylaminomethyl, (wherein each alkyl is independently lower ($C_1-C_6$) alkyl),
(ii) $C_1-C_6$alkoxyNR$_8$R$_9$, NR$_8$R$_9$, NR$_8$COR$_9$, CONR$_8$R$_9$, wherein $R_8$ and $R_9$ are the same or different and represent hydrogen, straight or branched chain lower alkyl,
(iii) $O(CH_2)_nCO_2R_A$ wherein n=1,2,3,4, COR$_A$, and CO$_2$R$_A$, wherein $R_A$ represents hydrogen or straight chain lower alkyl,
(iv) SO$_2$R$_A$, NHSO$_2$R$_A$, SO$_2$NHR$_A$, SO$_2$NHCOR$_A$, and CONHSO$_2$R$_A$, wherein $R_A$ represents hydrogen or straight chain lower alkyl, $R_2$ and $R_3$ are the same or different and represent
(i) halogen, trifluoromethyl, trifluoromethoxy, lower alkoxy having 1–6 carbon atoms, lower alkyl, amino methyl, mono or dialkylaminomethyl, wherein each alkyl is independently lower ($C_1$–$C_6$) alkyl, (ii) $C_1$–$C_6$alkoxyNR$_8$'R$_9$', NR$_8$'R$_9$', CONR$_8$'R$_9$', NR$_8$'COR$_9$', wherein R$_8$' and R$_9$' are the same or different and represent hydrogen or straight or branched chain lower alkyl, (iii) O(CH$_2$)$_n$CO$_2$R$_A$' where n=1,2,3,4, COR$_A$', or CO$_2$R$_A$', wherein R$_A$' represents hydrogen or straight chain lower alkyl; or R$_4$ represents straight or branched chain lower alkyl;

R$_5$ represents halogen or trifluoromethyl;

R$_6$, R$_7$ and R$_7$' are the same or different and represent (i) hydrogen, trifluoromethyl, trifluoromethoxy, nitrile, $C_1$–$C_{10}$ alkyl, $C_1$–$C_{10}$ alkoxy (with the proviso that R$_6$, R$_7$, or R$_7$' may not be $C_1$–$C_{10}$ alkoxy when located ortho to Y), $C_1$–$C_6$alkylthio, halogen, aminomethyl, di($C_1$–$C_6$)alkylamino, mono or di$C_1$–$C_6$alkylaminomethyl, or (ii) $C_1$–$C_6$ alkoxyaminoalkyl where the amino is mono or disubstituted with straight or branched chain lower alkyl;

(iii) or any two adjacent R$_6$, R$_7$ or R$_7$' may be joined to form a 5 to 7 membered carbocyclic ring; and Y represents a bond or CH$_2$, when Y=CH$_2$ it may be mono or disubstituted with a straight or branched chain lower alkyl, or straight or branched chain lower alkoxy having 1–6 carbon atoms.

3. A compound of the formula:

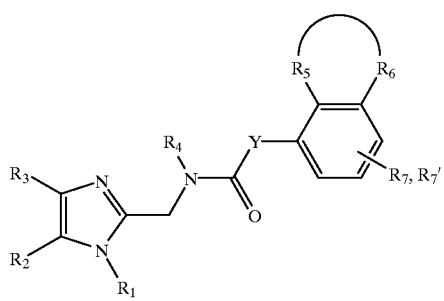

or a pharmaceutically acceptable salt, prodrug, or solvate thereof, wherein:

R$_1$ is benzyl which is optionally substituted directly or through a O(CH$_2$)$_n$ linker (where n=1, 2, 3 or 4) with up to three substituents independently selected from:

(i) halogen (with the proviso that R$_1$ may not be 3-Fluorobenzyl), nitro, trifluoromethyl, trifluoromethoxy, cyano, hydroxyl, $C_1$–$C_6$ alkyl, amino, $C_1$–$C_6$ alkoxy, aminomethyl, mono or di($C_1$–$C_6$)alkylamino, mono or dialkylaminomethyl, (wherein each alkyl is independently lower ($C_1$–$C_6$) alkyl), (ii) $C_1$–$C_6$alkoxyNR$_8$R$_9$, NR$_8$R$_9$, NR$_8$COR$_9$, CONR$_8$R$_9$, wherein R$_8$ and R$_9$ are the same or different and represent hydrogen, straight or branched chain lower alkyl, (iii) O(CH$_2$)$_n$CO$_2$R$_A$ wherein n=1,2,3,4, COR$_A$, and CO$_2$R$_A$, wherein R$_A$ represents hydrogen or straight chain lower alkyl, (iv) SO$_2$R$_A$, NHSO$_2$R$_A$, SO$_2$NHR$_A$, SO$_2$NHCOR$_A$, CONHSO$_2$R$_A$, wherein R$_A$ represents hydrogen or straight chain lower alkyl;

R$_2$ and R$_3$ are the same or different and represent (i) halogen, trifluoromethyl, trifluoromethoxy, lower alkoxy having 1–6 carbon atoms, lower alkyl, amino methyl, mono or dialkylaminomethyl, wherein each alkyl is independently lower ($C_1$–$C_6$) alkyl, (ii) $C_1$–$C_6$alkoxyNR$_8$'R$_9$', NR$_8$'R$_9$', CONR$_8$'R$_9$', NR$_8$'COR$_9$', wherein R$_8$' and R$_9$' are the same or different and represent hydrogen or straight or branched chain lower alkyl, (iii) O(CH$_2$)$_n$CO$_2$R$_A$' where n=1,2,3,4, COR$_A$', or CO$_2$R$_A$', wherein R$_A$' represents hydrogen or straight chain lower alkyl;

R$_4$ represents straight or branched chain lower alkyl;

R$_5$ is part of an aromatic ring formed with R$_6$;

R$_6$ is part of a 6 membered carbocyclic aromatic ring formed with R$_5$ which is optionally substituted with up to four substituents selected from:

(i) halogen, nitro, trifluoromethyl, cyano, hydroxyl, $C_1$–$C_6$ alkyl, amino, $C_1$–$C_6$ alkoxy, aminomethyl, alkylaminomethyl, mono or di($C_1$–$C_6$)alkylamino, mono or dialkylaminomethyl, wherein each alkyl is independently lower ($C_1$–$C_6$) alkyl, (ii) $C_1$–$C_6$alkoxyNR$_8$"R$_9$", NR$_8$"R$_9$", CONR$_8$"R$_9$", NR$_8$"COR$_9$", where R$_8$" and R$_9$" are the same or different and represent hydrogen or straight or branched chain lower alkyl, (iii) O(CH$_2$)$_n$CO$_2$R$_A$" where n=1,2,3,4, COR$_A$", or CO$_2$R$_A$", wherein R$_A$" represents hydrogen or straight chain lower alkyl; and R$_7$ and R$_7$' represent hydrogen, trifluoromethyl, trifluoromethoxy, nitrile, $C_1$–$C_{10}$ alkyl, $C_1$–$C_{10}$ alkoxy (with the proviso that R$_6$, R$_7$, or R$_7$' may not be $C_1$–$C_{10}$ alkoxy when located ortho to Y), $C_1$–$C_6$alkylthio, halogen, aminomethyl, di($C_1$–$C_6$)alkylamino, mono or di$C_1$–$C_6$alkylaminomethyl, or $C_1$–$C_6$alkoxyaminoalkyl where the amino is mono or disubstituted with straight or branched chain lower alkyl; and Y represents a bond or CH$_2$, when Y=CH$_2$ it may be mono or disubstituted with a straight or branched chain lower alkyl, or straight or branched chain lower alkoxy having 1–6 carbon atoms.

4. A compound according to claim 2 of the formula

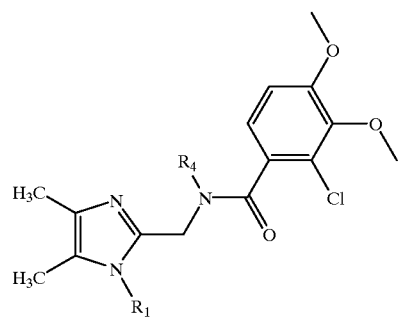

wherein R$_1$ and R$_4$ are as defined in claim 2.

5. A compound according to claim 4 wherein R$_4$ is isoamyl or n-pentyl.

6. A compound according to claim 2 of the formula

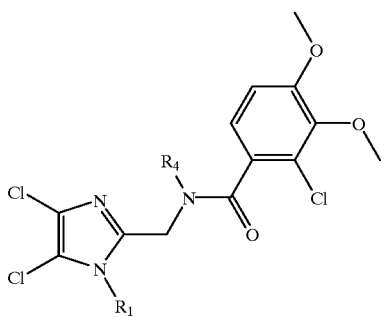

wherein $R_1$ and $R_4$ are as defined in claim 2.

7. A compound according to claim 6 wherein $R_4$ is isoamyl or n-pentyl.

8. A compound according to claim 1, which is (2-Chloro-3,4-dimethoxyphenyl)-N-({1-[(2-chlorophenyl)methyl]-4,5-dimethylimidazol-2-yl}methyl)-N-(3-methylbutyl) carboxamide.

9. A compound according to claim 1, which is (2-Chloro-3,4-dimethoxyphenyl)-N-({1-[(2-methoxyphenyl)methyl]-4,5-dimethylimidazol-2-yl}methyl)-N-(3-methylbutyl) carboxamide.

10. A compound according to claim 1, which is (2-Chloro-3,4- dimethoxyphenyl)-N-({1-[(2-hydroxyphenyl)methyl]4,5-dimethylimidazol-2-yl}methyl)-N-(3-methylbutyl) carboxamide.

11. A compound according to claim 1, which is Ethyl{2-[(2-{[(2-chloro-3,4-dimethoxyphenyl)-N-(3-methylbutyl)carbonylamino]methyl}-4,5-dimethylimidazol-1-yl)methyl]phenoxy}acetate.

12. A compound according to claim 1, which is {2-[(2-{[(2-Chloro-3,4-dimethoxyphenyl)-N-(3-methylbutyl)carbonylamino]methyl}-4,5-dimethylimidazol-1-yl)methyl]phenoxy}acetic acid.

13. A compound according to claim 1, which is (2-Chloro-3,4- dimethoxyphenyl)-N-({1-[(2-cyanophenyl)methyl]4,5-dimethylimidazol-2-yl}methyl)-N-(3-methylbutyl) carboxamide.

14. A compound according to claim 1, which is 2-{2-{[(2-Chloro-3,4-dimethoxyphenyl)-N-(3-methylbutyl)carbonylamino}methyl]-4,5-dimethylimidazol-1-yl)methyl}benzoic acid.

15. A compound according to claim 1, which is (2-Chloro-3,4- dimethoxyphenyl)-N-({1-[(2-[cyanomethoxy]-phenyl)methyl]4,5-dimethylimidazol-2-yl}methyl)-N-(3-methylbutyl)carboxamide.

16. A compound according to claim 1, which is (2-Chloro-3,4-dimethoxyphenyl)-N-{[1-benzyl-4,5-dimethylimidazol-2-yl]methyl}-N-(3-methylbutyl) carboxamide.

17. A compound according to claim 1, which is (2-Chloro-3,4-dimethoxyphenyl-N-({4,5-dimethyl-1-[(2-methylphenyl)methyl]}imidazol-2-yl}methyl-N-(3-methylbutyl)carboxamide.

18. A compound according to claim 1, which is (2-Chloro-3,4-dimethoxyphenyl-N-[(4,5-dimethyl-1-{[2-(trifluoromethyl)phenyl]methyl}imidazol-2-yl)methyl]-N-(3-methylbutyl)carboxamide.

19. A compound according to claim 1, which is N-{[4,5-Dichloro-1-benzylimidazol-2-yl]methyl}(2-chloro-3,4-dimethoxyphenyl)-N-(3-methylbutyl)carboxamide.

20. A compound according to claim 1, which is N-({4,5-Dichloro-1-[(2-chlorophenyl)methyl]imidazol-2-yl}methyl)(2-chloro-3,4-dimethoxyphenyl)-N-(3-methylbutyl) carboxamide.

21. A compound according to claim 1, which is N-({4,5-Dichloro-1-[(2-methylphenyl)methyl]imidazol-2-yl}methyl)(2-chloro-3,4-dimethoxyphenyl)-N-(3-methylbutyl)carboxamide.

22. A compound according to claim 1, which is (2-Chloro-3,4-dimethoxyphenyl)-N-{4,5-diethyl-1-[(5-ethyl-2-methoxyphenyl)methyl]imidazol-2-yl}methyl-N-(3-methylbutyl)carboxamide.

23. A compound according to claim 1, which is (2-Chloro-3,4- dimethoxyphenyl)-N-({1-[(5-bromo-2-hydroxyphenyl)methyl]4,5-dimethylimidazol-2-yl}methyl-N-(3-methylbutyl)carboxamide.

24. A compound according to claim 1, which is (2-Chloro-3,4-dimethoxyphenyl)-N-{3,4-dimethyl-1-[(5-chloro-2-hydroxyphenyl)methyl]imidazol-2-yl}methyl-N-(3-methylbutyl)carboxamide.

25. A compound according to claim 1, which is (2-Chloro-3,4-dimethoxyphenyl)-N-({1-[(2-carboxamidophenyl)methyl]-4,5-dimethylimidazol-2-yl}methyl)-N-(3-methylbutyl)carboxamide.

26. A compound according to claim 1, which is N-({4,5-Dichloro-1-[(2-carboxamidophenyl)methyl]imidazol-2-yl}methyl)(2-chloro-3,4-dimethoxyphenyl)-N-(3-methylbutyl)carboxamide.

27. A compound according to claim 1, which is (2-Chloro-3,4-dimethoxyphenyl)-N-({1-[(2-sulfonamidophenyl)methyl]-4,5-dimethylimidazol-2-yl}methyl)-N-(3-methylbutyl)carboxamide.

28. A compound according to claim 1, which is N-({4,5-Dichloro-1-[(2-sulfonamidophenyl)methyl]imidazol-2-yl}methyl)(2-chloro-3,4-dimethoxyphenyl)-N-(3-methylbutyl)carboxamide.

29. A pharmaceutical composition comprising a compound according to claim 1, together with at least one pharmaceutically acceptable carrier or excipient.

30. A method of increasing the permeability of the blood brain barrier, which method comprises administering an effective amount of a compound according to claim 1 to a patient.

31. A method of increasing the brain concentration of a CNS active compound, which method comprises administering an effective amount of a compound according to any one of claim 1 and the CNS active compound to a patient.

32. A compound of the formula

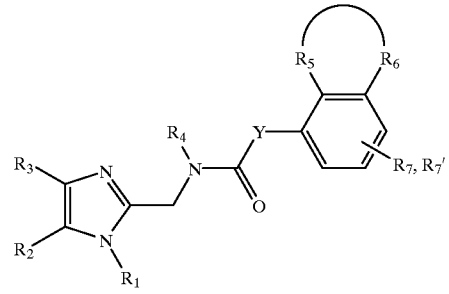

or a pharmaceutically acceptable salt, prodrug, or solvate thereof, wherein:

$R_4$ represents straight or branched chain lower alkyl;

$R_5$ represents hydrogen, $C_1$–$C_2$alkyl, $C_1$–$C_2$alkoxy, —$SCH_3$, phenyl, benzyl, phenethyl, phenoxy, halogen U or trifluoromethyl;

$R_6$, $R_7$ and $R_7'$ are the same or different and represent hydrogen, trifluoromethyl, trifluoromethoxy, nitrile, $C_1$–$C_{10}$ alkyl, $C_1$–$C_{10}$ alkoxy, $C_1$–$C_6$alkylthio, halogen, aminomethyl, di($C_1$–$C_6$)alkylamino, phenyl, phenoxy, mono or di$C_1$–$C_6$alkylaminomethyl; and $R_{10}$ represents methoxy and $R_{11}$ represents hydrogen, or $R_{10}$ represents hydrogen and $R_{11}$ represents methoxy.

33. A compound according to claim 32 which is selected from compounds (1) through (20):

| | $R_4$ | $R_5$ | $R_6$ | $R_7$ |
|---|---|---|---|---|
| (1) | n-pentyl | H | —OCH$_2$CH$_3$ | —OCH$_2$CH$_3$ |
| (2) | 3-methylbutyl | H | —OCH$_2$CH$_3$ | —OCH$_2$CH$_3$ |
| (3) | n-pentyl | H | —OCH$_2$CH$_3$ | —OCH$_2$CH$_3$ |
| (4) | 3-methylbutyl | H | —OCH$_2$CH$_3$ | —OCH$_2$CH$_3$ |
| (5) | n-pentyl | H | —CF$_3$ | H |
| (6) | 3-methylbutyl | H | —CF$_3$ | H |
| (7) | n-pentyl | H | —CF$_3$ | H |
| 8) | 3-methylbutyl | H | —CF$_3$ | H |
| (9) | n-pentyl | H | I | —CH$_3$ |
| (10) | 3-methylbutyl | H | I | —CH$_3$ |
| (11) | n-pentyl | H | I | —CH$_3$ |
| (12) | 3-methylbutyl | H | I | —CH$_3$ |
| (13) | n-pentyl | H | H | —O(CH$_2$)$_8$CH$_3$ |
| (14) | 3-methylbutyl | H | H | —O(CH$_2$)$_8$CH$_3$ |
| (15) | n-pentyl | H | H | —O(CH$_2$)$_8$CH$_3$ |
| (16) | 3-methylbutyl | H | H | —O(CH$_2$)$_8$CH$_3$ |
| (17) | n-pentyl | H | H | —O(CH$_2$)$_9$CH$_3$ |
| (18) | 3-methylbutyl | H | H | —O(CH$_2$)$_9$CH$_3$ |
| (19) | n-pentyl | H | H | —O(CH$_2$)$_9$CH$_3$ |
| (20) | 3-methylbutyl | H | H | —O(CH$_2$)$_9$CH$_3$ |

| | $R_7'$ | $R_{10}$ | $R_{11}$ |
|---|---|---|---|
| (1) | —OCH$_2$CH$_3$ | —OCH$_3$ | H |
| (2) | —OCH$_2$CH$_3$ | H | —OCH$_3$ |
| (3) | —OCH$_2$CH$_3$ | H | —OCH$_3$ |
| (4) | —OCH$_2$CH$_3$ | —OCH$_3$ | H |
| (5) | —CF$_3$ | —OCH$_3$ | H |
| (6) | —CF$_3$ | H | —OCH$_3$ |
| (7) | —CF$_3$ | H | —OCH$_3$ |
| (8) | —CF$_3$ | —OCH$_3$ | H |
| (9) | H | —OCH$_3$ | H |
| (10) | H | H | —OCH$_3$ |
| (11) | H | H | —OCH$_3$ |
| (12) | H | —OCH$_3$ | H |
| (13) | H | —OCH$_3$ | H |
| (14) | H | H | —OCH$_3$ |
| (15) | H | H | —OCH$_3$ |
| (16) | H | —OCH$_3$ | H |
| (17) | H | —OCH$_3$ | H |
| (18) | H | H | —OCH$_3$ |
| (19) | H | H | —OCH$_3$ |
| (20) | H | —OCH$_3$ | H. |

34. A compound according to claim 32 wherein $R_6$ and $R_7$ are hydrogen which is selected from compounds (21) through (28):

| | $R_4$ | $R_5$ | $R_7'$ | $R_{10}$ | $R_{11}$ |
|---|---|---|---|---|---|
| (21) | n-pentyl | Cl | —SCH$_3$ | —OCH$_3$ | H |
| (22) | 3-methylbutyl | Cl | —SCH$_3$ | H | —OCH$_3$ |
| (23) | n-pentyl | Cl | —SCH$_3$ | H | —OCH$_3$ |
| (24) | 3-methylbutyl | Cl | —SCH$_3$ | —OCH$_3$ | H |
| (25) | n-pentyl | Br | —CH$_3$ | —OCH$_3$ | H |
| (26) | 3-methylbutyl | Br | —CH$_3$ | H | —OCH$_3$ |
| (27) | n-pentyl | Br | —CH$_3$ | H | —OCH$_3$ |
| (28) | 3-methylbutyl | Br | —CH$_3$ | —OCH$_3$ | H. |

35. A compound according to claim 32 which is selected from compounds (29) through (52):

| | $R_4$ | $R_5$ | $R_6$ | $R_7$ |
|---|---|---|---|---|
| (29) | n-pentyl | Cl | H | —OCH$_3$ |
| (30) | 3-methylbutyl | Cl | H | —OCH$_3$ |
| (31) | n-pentyl | Cl | H | —OCH$_3$ |
| (32) | 3-methylbutyl | Cl | H | —OCH$_3$ |
| (33) | n-pentyl | Br | —CH$_3$ | H |
| (34) | 3-methylbutyl | Br | —CH$_3$ | H |
| (35) | n-pentyl | Br | —CH$_3$ | H |
| (36) | 3-methylbutyl | Br | —CH$_3$ | H |
| (37) | n-pentyl | Cl | —CF$_3$ | H |
| (38) | 3-methylbutyl | Cl | —CF$_3$ | H |
| (39) | n-pentyl | Cl | —CF$_3$ | H |
| (40) | 3-methylbutyl | Cl | —CF$_3$ | H |
| (41) | n-pentyl | Cl | H | H |
| (42) | 3-methylbutyl | Cl | H | H |
| (43) | n-pentyl | Cl | H | H |
| (44) | 3-methylbutyl | Cl | H | H |
| (45) | n-pentyl | Br | H | —OCH$_3$ |
| (46) | 3-methylbutyl | Br | H | —OCH$_3$ |
| (47) | n-pentyl | Br | H | —OCH$_3$ |
| (48) | 3-methylbutyl | Br | H | —OCH$_3$ |
| (49) | n-pentyl | —SCH$_3$ | H | H |
| (50) | 3-methylbutyl | —SCH$_3$ | H | H |
| (51) | n-pentyl | —SCH$_3$ | H | H |
| (52) | 3-methylbutyl | —SCH$_3$ | H | H |

| | $R_7'$ | $R_{10}$ | $R_{11}$ |
|---|---|---|---|
| (29) | —OCH$_3$ | —OCH$_3$ | H |
| (30) | —OCH$_3$ | H | —OCH$_3$ |
| (31) | —OCH$_3$ | H | —OCH$_3$ |
| (32) | —OCH$_3$ | —OCH$_3$ | H |
| (33) | H | —OCH$_3$ | H |
| (34) | H | H | —OCH$_3$ |
| (35) | H | H | —OCH$_3$ |
| (36) | H | —OCH$_3$ | H |
| (37) | H | —OCH$_3$ | H |
| (38) | H | H | —OCH$_3$ |
| (39) | H | H | —OCH$_3$ |
| (40) | H | —OCH$_3$ | H |
| (41) | H | —OCH$_3$ | H |
| (42) | H | H | —OCH$_3$ |
| (43) | H | H | —OCH$_3$ |
| (44) | H | —OCH$_3$ | H |
| (45) | —OCH$_3$ | —OCH$_3$ | H |
| (46) | —OCH$_3$ | H | —OCH$_3$ |
| (47) | —OCH$_3$ | H | —OCH$_3$ |
| (48) | —OCH$_3$ | —OCH$_3$ | H |
| (49) | H | —OCH$_3$ | H |
| (50) | H | H | —OCH$_3$ |
| (51) | H | H | —OCH$_3$ |
| (52) | H | —OCH$_3$ | H. |

36. A compound according to claim 32, wherein $R_7'$ is hydrogen which is selected from compounds (53) through (80):

| | $R_4$ | $R_5$ | $R_6$ | $R_7$ | $R_{10}$ | $R_{11}$ |
|---|---|---|---|---|---|---|
| (53) | n-pentyl | H | H | H | —OCH$_3$ | H |
| (54) | 3-methylbutyl | H | H | H | H | —OCH$_3$ |
| (55) | n-pentyl | H | H | H | H | —OCH$_3$ |
| (56) | 3-methylbutyl | H | H | H | —OCH$_3$ | H |
| (57) | n-pentyl | H | —CH$_3$ | H | —OCH$_3$ | H |
| (58) | 3-methylbutyl | H | —CH$_3$ | H | H | —OCH$_3$ |
| (59) | n-pentyl | H | —CH$_3$ | H | H | —OCH$_3$ |
| (60) | 3-methylbutyl | H | —CH$_3$ | H | —OCH$_3$ | H |
| (61) | n-pentyl | H | H | —CH$_3$ | —OCH$_3$ | H |
| (62) | 3-methylbutyl | H | H | —CH$_3$ | H | —OCH$_3$ |

-continued

| | $R_4$ | $R_5$ | $R_6$ | $R_7$ | $R_{10}$ | $R_{11}$ |
|---|---|---|---|---|---|---|
| (63) | n-pentyl | H | H | —$CH_3$ | H | —$OCH_3$ |
| (64) | 3-methylbutyl | H | H | —$CH_3$ | —$OCH_3$ | H |
| (65) | n-pentyl | —$CH_3$ | H | H | —$OCH_3$ | H |
| (66) | 3-methylbutyl | —$CH_3$ | H | H | H | —$OCH_3$ |
| (67) | n-pentyl | —$CH_3$ | H | H | H | —$OCH_3$ |
| (68) | 3-methylbutyl | —$CH_3$ | H | H | —$OCH_3$ | H |
| (69) | n-pentyl | H | F | H | —$OCH_3$ | H |
| (70) | 3-methylbutyl | H | F | H | H | —$OCH_3$ |
| (71) | n-pentyl | H | F | H | H | —$OCH_3$ |
| (72) | 3-methylbutyl | H | F | H | —$OCH_3$ | H |
| (73) | n-pentyl | H | H | F | —$OCH_3$ | H |
| (74) | 3-methylbutyl | H | H | F | H | —$OCH_3$ |
| (75) | n-pentyl | H | H | F | H | —$OCH_3$ |
| (76) | 3-methylbutyl | H | H | F | —$OCH_3$ | H |
| (77) | n-pentyl | H | H | H | —$OCH_3$ | H |
| (78) | 3-methylbutyl | H | H | H | H | —$OCH_3$ |
| (79) | n-pentyl | H | H | H | H | —$OCH_3$ |
| (80) | 3-methylbutyl. | H | H | H | —$OCH_3$ | H |

37. A compound according to claim 1 which is selected from compounds (81) through (104):

| | $R_4$ | $R_5$ | $R_6$ | $R_7$ |
|---|---|---|---|---|
| (81) | n-pentyl | H | H | —$CH_2CH_3$ |
| (82) | 3-methylbutyl | H | H | —$CH_2CH_3$ |
| (83) | n-pentyl | H | H | —$CH_2CH_3$ |
| (84) | 3-methylbutyl | H | H | —$CH_2CH_3$ |
| (85) | n-pentyl | H | —$CH_3$ | —$CH_3$ |
| (86) | 3-methylbutyl | H | —$CH_3$ | —$CH_3$ |
| (87) | n-pentyl | H | —$CH_3$ | —$CH_3$ |
| (88) | 3-methylbutyl | H | —$CH_3$ | —$CH_3$ |
| (89) | n-pentyl | H | —$CH_3$ | H |
| (90) | 3-methylbutyl | H | —$CH_3$ | H |
| (91) | n-pentyl | H | —$CH_3$ | H |
| (92) | 3-methylbutyl | H | —$CH_3$ | H |
| (93) | n-pentyl | H | —$CH_3$ | H |
| (94) | 3-methylbutyl | H | —$CH_3$ | H |
| (95) | n-pentyl | H | —$CH_3$ | H |
| (96) | 3-methylbutyl | H | —$CH_3$ | H |
| (97) | n-pentyl | H | H | H |
| (98) | 3-methylbutyl | H | H | H |
| (99) | n-pentyl | H | H | H |
| (100) | 3-methylbutyl | H | H | H |
| (101) | n-pentyl | —$CH_3$ | H | —$CH_3$ |
| (102) | 3-methylbutyl | —$CH_3$ | H | —$CH_3$ |
| (103) | n-pentyl | —$CH_3$ | H | —$CH_3$ |
| (104) | 3-methylbutyl | —$CH_3$ | H | —$CH_3$ |

| | $R_7'$ | $R_{10}$ | $R_{11}$ |
|---|---|---|---|
| (81) | H | —$OCH_3$ | H |
| (82) | H | H | —$OCH_3$ |
| (83) | H | H | —$OCH_3$ |
| (84) | H | —$OCH_3$ | H |
| (85) | H | —$OCH_3$ | H |
| (86) | H | H | —$OCH_3$ |
| (87) | H | H | —$OCH_3$ |
| (88) | H | —$OCH_3$ | H |
| (89) | —$CH_3$ | —$OCH_3$ | H |
| (90) | —$CH_3$ | H | —$OCH_3$ |
| (91) | —$CH_3$ | H | —$OCH_3$ |
| (92) | —$CH_3$ | —$OCH_3$ | H |
| (93) | H | —$OCH_3$ | H |
| (94) | H | H | —$OCH_3$ |
| (95) | H | H | —$OCH_3$ |
| (96) | H | —$OCH_3$ | H |
| (97) | —$CH_3$ | —$OCH_3$ | H |
| (98) | —$CH_3$ | H | —$OCH_3$ |
| (99) | —$CH_3$ | H | —$OCH_3$ |
| (100) | —$CH_3$ | —$OCH_3$ | H |
| (101) | H | —$OCH_3$ | H |
| (102) | H | H | —$OCH_3$ |
| (103) | H | H | —$OCH_3$ |
| (104) | H | —$OCH_3$ | H. |

38. A compound according to claim 32 which is selected from compounds (105) through (132):

| | $R_4$ | $R_5$ | $R_6$ | $R_7$ |
|---|---|---|---|---|
| (105) | n-pentyl | H | —$OCH_3$ | H |
| (106) | 3-methylbutyl | H | —$OCH_3$ | H |
| (107) | n-pentyl | H | —$OCH_3$ | H |
| (108) | 3-methylbutyl | H | —$OCH_3$ | H |
| (109) | n-pentyl | H | H | —$OCH_3$ |
| (110) | 3-methylbutyl | H | H | —$OCH_3$ |
| (111) | n-pentyl | H | H | —$OCH_3$ |
| (112) | 3-methylbutyl | H | H | —$OCH_3$ |
| (113) | n-pentyl | —$OCH_3$ | H | H |
| (114) | 3-methylbutyl | —$OCH_3$ | H | H |
| (115) | n-pentyl | —$OCH_3$ | H | H |
| (116) | 3-methylbutyl | —$OCH_3$ | H | H |
| (117) | n-pentyl | H | F | —$CH_3$ |
| (118) | 3-methylbutyl | H | F | —$CH_3$ |
| (119) | n-pentyl | H | F | —$CH_3$ |
| (120) | 3-methylbutyl | H | F | —$CH_3$ |
| (121) | n-pentyl | —$CH_3$ | F | H |
| (122) | 3-methylbutyl | —$CH_3$ | F | H |
| (123) | n-pentyl | —$CH_3$ | F | H |
| (124) | 3-methylbutyl | —$CH_3$ | F | H |
| (125) | n-pentyl | —$CH_3$ | H | H |
| (126) | 3-methylbutyl | —$CH_3$ | H | H |
| (127) | n-pentyl | —$CH_3$ | H | H |
| (128) | 3-methylbutyl | —$CH_3$ | H | H |
| (129) | n-pentyl | F | —$CH_3$ | H |
| (130) | 3-methylbutyl | F | —$CH_3$ | H |
| (131) | n-pentyl | F | —$CH_3$ | H |
| (132) | 3-methylbutyl | F | —$CH_3$ | H |

| | $R_7'$ | $R_{10}$ | $R_{11}$ |
|---|---|---|---|
| (105) | H | —$OCH_3$ | H |
| (106) | H | H | —$OCH_3$ |
| (107) | H | H | —$OCH_3$ |
| (108) | H | —$OCH_3$ | H |
| (109) | H | —$OCH_3$ | H |
| (110) | H | H | —$OCH_3$ |
| (111) | H | H | —$OCH_3$ |
| (112) | H | —$OCH_3$ | H |
| (113) | H | —$OCH_3$ | H |
| (114) | H | H | —$OCH_3$ |
| (115) | H | H | —$OCH_3$ |
| (116) | H | —$OCH_3$ | H |
| (117) | H | —$OCH_3$ | H |
| (118) | H | H | —$OCH_3$ |
| (119) | H | H | —$OCH_3$ |
| (120) | H | —$OCH_3$ | H |
| (121) | H | —$OCH_3$ | H |
| (122) | H | H | —$OCH_3$ |
| (123) | H | H | —$OCH_3$ |
| (124) | H | —$OCH_3$ | H |
| (125) | F | —$OCH_3$ | H |
| (126) | F | H | —$OCH_3$ |
| (127) | F | H | —$OCH_3$ |
| (128) | F | —$OCH_3$ | H |
| (129) | H | —$OCH_3$ | H |
| (130) | H | H | —$OCH_3$ |
| (131) | H | H | —$OCH_3$ |
| (132) | H | —$OCH_3$ | H. |

39. A compound according to claim 32 which is selected from compounds (133) through (156):

|       | R$_4$         | R$_5$ | R$_6$ | R$_7$ | R$_7'$ | R$_{10}$ | R$_{11}$ |
|-------|---------------|-------|-------|-------|--------|----------|----------|
| (133) | n-pentyl      | H     | Cl    | H     | H      | —OCH$_3$ | H        |
| (134) | 3-methylbutyl | H     | Cl    | H     | H      | H        | —OCH$_3$ |
| (135) | n-pentyl      | H     | Cl    | H     | H      | H        | —OCH$_3$ |
| (136) | 3-methylbutyl | H     | Cl    | H     | H      | —OCH$_3$ | H        |
| (137) | n-pentyl      | H     | H     | Cl    | H      | —OCH$_3$ | H        |
| (138) | 3-methylbutyl | H     | H     | Cl    | H      | H        | —OCH$_3$ |
| (139) | n-pentyl      | H     | H     | Cl    | H      | H        | —OCH$_3$ |
| (140) | 3-methylbutyl | H     | H     | Cl    | H      | —OCH$_3$ | H        |
| (141) | n-pentyl      | Cl    | H     | H     | H      | —OCH$_3$ | H        |
| (142) | 3-methylbutyl | Cl    | H     | H     | H      | H        | —OCH$_3$ |
| (143) | n-pentyl      | Cl    | H     | H     | H      | H        | —OCH$_3$ |
| (144) | 3-methylbutyl | Cl    | H     | H     | H      | —OCH$_3$ | H        |
| (145) | n-pentyl      | H     | F     | F     | H      | —OCH$_3$ | H        |
| (146) | 3-methylbutyl | H     | F     | F     | H      | H        | —OCH$_3$ |
| (147) | n-pentyl      | H     | F     | F     | H      | H        | —OCH$_3$ |
| (148) | 3-methylbutyl | H     | F     | F     | H      | —OCH$_3$ | H        |
| (149) | n-pentyl      | F     | F     | H     | H      | —OCH$_3$ | H        |
| (150) | 3-methylbutyl | F     | F     | H     | H      | H        | —OCH$_3$ |
| (151) | n-pentyl      | F     | F     | H     | H      | H        | —OCH$_3$ |
| (152) | 3-methylbutyl | F     | F     | H     | H      | —OCH$_3$ | H        |
| (153) | n-pentyl      | F     | H     | H     | F      | —OCH$_3$ | H        |
| (154) | 3-methylbutyl | F     | H     | H     | F      | H        | —OCH$_3$ |
| (155) | n-pentyl      | F     | H     | H     | F      | H        | —OCH$_3$ |
| (156) | 3-methylbutyl | F     | H     | H     | F      | —OCH$_3$ | H.       |

40. A compound according to claim 32 which is selected from compounds (157) through (180):

|       | R$_4$         | R$_5$       | R$_6$       |
|-------|---------------|-------------|-------------|
| (157) | n-pentyl      | F           | H           |
| (158) | 3-methylbutyl | F           | H           |
| (159) | n-pentyl      | F           | H           |
| (160) | 3-methylbutyl | F           | H           |
| (161) | n-pentyl      | H           | H           |
| (162) | 3-methylbutyl | H           | H           |
| (163) | n-pentyl      | H           | H           |
| (164) | 3-methylbutyl | H           | H           |
| (165) | n-pentyl      | H           | H           |
| (166) | 3-methylbutyl | H           | H           |
| (167) | n-pentyl      | H           | H           |
| (168) | 3-methylbutyl | H           | H           |
| (169) | n-pentyl      | H           | —OCH$_2$CH$_3$ |
| (170) | 3-methylbutyl | H           | —OCH$_2$CH$_3$ |
| (171) | n-pentyl      | H           | —OCH$_2$CH$_3$ |
| (172) | 3-methylbutyl | H           | —OCH$_2$CH$_3$ |
| (173) | n-pentyl      | H           | H           |
| (174) | 3-methylbutyl | H           | H           |
| (175) | n-pentyl      | H           | H           |
| (176) | 3-methylbutyl | H           | H           |
| (177) | n-pentyl      | —OCH$_2$CH$_3$ | H           |
| (178) | 3-methylbutyl | —OCH$_2$CH$_3$ | H           |
| (179) | n-pentyl      | —OCH$_2$CH$_3$ | H           |
| (180) | 3-methylbutyl | —OCH$_2$CH$_3$ | H           |

|       | R$_7$      | R$_7'$ | R$_{10}$  | R$_{11}$  |
|-------|------------|--------|-----------|-----------|
| (157) | F          | H      | —OCH$_3$  | H         |
| (158) | F          | H      | H         | —OCH$_3$  |
| (159) | F          | H      | H         | —OCH$_3$  |
| (160) | F          | H      | —OCH$_3$  | H         |
| (161) | —CH$_2$CH$_3$ | H   | —OCH$_3$  | H         |
| (162) | —CH$_2$CH$_3$ | H   | H         | —OCH$_3$  |
| (163) | —CH$_2$CH$_3$ | H   | H         | —OCH$_3$  |
| (164) | —CH$_2$CH$_3$ | H   | —OCH$_3$  | H         |
| (165) | —CH(CH$_3$)$_2$ | H | —OCH$_3$  | H         |
| (166) | —CH(CH$_3$)$_2$ | H | H         | —OCH$_3$  |
| (167) | —CH(CH$_3$)$_2$ | H | H         | —OCH$_3$  |
| (168) | —CH(CH$_3$)$_2$ | H | —OCH$_3$  | H         |
| (169) | H          | H      | —OCH$_3$  | H         |
| (170) | H          | H      | H         | —OCH$_3$  |
| (171) | H          | H      | H         | —OCH$_3$  |
| (172) | H          | H      | —OCH$_3$  | H         |
| (173) | —OCH$_2$CH$_3$ | H  | —OCH$_3$  | H         |
| (174) | —OCH$_2$CH$_3$ | H  | H         | —OCH$_3$  |
| (175) | —OCH$_2$CH$_3$ | H  | H         | —OCH$_3$  |
| (176) | —OCH$_2$CH$_3$ | H  | —OCH$_3$  | H         |
| (177) | H          | H      | —OCH$_3$  | H         |
| (178) | H          | H      | H         | —OCH$_3$  |
| (179) | H          | H      | H         | —OCH$_3$  |
| (180) | H          | H      | —OCH$_3$  | H.        |

41. A compound according to claim 32 which is selected from compounds (185) through (240):

|       | R$_4$         | R$_5$       | R$_6$       | R$_7$              |
|-------|---------------|-------------|-------------|--------------------|
| (185) | n-pentyl      | H           | H           | —SCH$_3$           |
| (186) | 3-methylbutyl | H           | H           | —SCH$_3$           |
| (187) | n-pentyl      | H           | H           | —SCH$_3$           |
| (188) | 3-methylbutyl | H           | H           | —SCH$_3$           |
| (189) | n-pentyl      | H           | F           | —OCH$_3$           |
| (190) | 3-methylbutyl | H           | F           | —OCH$_3$           |
| (191) | n-pentyl      | H           | F           | —OCH$_3$           |
| (192) | 3-methylbutyl | H           | F           | —OCH$_3$           |
| (193) | n-pentyl      | H           | —CH$_3$     | Cl                 |
| (194) | 3-methylbutyl | H           | —CH$_3$     | Cl                 |
| (195) | n-pentyl      | H           | —CH$_3$     | Cl                 |
| (196) | 3-methylbutyl | H           | —CH$_3$     | Cl                 |
| (197) | n-pentyl      | H           | Cl          | F                  |
| (198) | 3-methylbutyl | H           | Cl          | F                  |
| (199) | n-pentyl      | H           | Cl          | F                  |
| (200) | 3-methylbutyl | H           | Cl          | F                  |
| (201) | n-pentyl      | H           | F           | F                  |
| (202) | 3-methylbutyl | H           | F           | F                  |
| (203) | n-pentyl      | H           | F           | F                  |
| (204) | 3-methylbutyl | H           | F           | F                  |
| (205) | n-pentyl      | H           | H           | —(CH$_2$)$_3$CH$_3$ |
| (206) | 3-methylbutyl | H           | H           | —(CH$_2$)$_3$CH$_3$ |
| (207) | n-pentyl      | H           | H           | —(CH$_2$)$_3$CH$_3$ |
| (208) | 3-methylbutyl | H           | H           | —(CH$_2$)$_3$CH$_3$ |
| (209) | n-pentyl      | H           | H           | —C(CH$_3$)$_3$     |
| (210) | 3-methylbutyl | H           | H           | —C(CH$_3$)$_3$     |
| (211) | n-pentyl      | H           | H           | —C(CH$_3$)$_3$     |
| (212) | 3-methylbutyl | H           | H           | —C(CH$_3$)$_3$     |
| (213) | n-pentyl      | H           | H           | —O(CH$_2$)$_2$CH$_3$ |
| (214) | 3-methylbutyl | H           | H           | —O(CH$_2$)$_2$CH$_3$ |
| (215) | n-pentyl      | H           | H           | —O(CH$_2$)$_2$CH$_3$ |
| (216) | 3-methylbutyl | H           | H           | —O(CH$_2$)$_2$CH$_3$ |
| (217) | n-pentyl      | H           | H           | —OCH(CH$_3$)$_2$   |
| (218) | 3-methylbutyl | H           | H           | —OCH(CH$_3$)$_2$   |
| (219) | n-pentyl      | H           | H           | —OCH(CH$_3$)$_2$   |
| (220) | 3-methylbutyl | H           | H           | —OCH(CH$_3$)$_2$   |
| (221) | n-pentyl      | H           | H           | —SCH$_2$CH$_3$     |
| (222) | 3-methylbutyl | H           | H           | —SCH$_2$CH$_3$     |
| (223) | n-pentyl      | H           | H           | —SCH$_2$CH$_3$     |
| (224) | 3-methylbutyl | H           | H           | —SCH$_2$CH$_3$     |
| (225) | n-pentyl      | H           | —OCH$_3$    | —OCH$_3$           |
| (226) | 3-methylbutyl | H           | —OCH$_3$    | —OCH$_3$           |
| (227) | n-pentyl      | H           | —OCH$_3$    | —OCH$_3$           |
| (228) | 3-methylbutyl | H           | —OCH$_3$    | —OCH$_3$           |
| (229) | n-pentyl      | H           | —OCH$_3$    | H                  |
| (230) | 3-methylbutyl | H           | —OCH$_3$    | H                  |
| (231) | n-pentyl      | H           | —OCH$_3$    | H                  |
| (232) | 3-methylbutyl | H           | —OCH$_3$    | H                  |
| (233) | n-pentyl      | —OCH$_3$    | —OCH$_3$    | H                  |
| (234) | 3-methylbutyl | —OCH$_3$    | —OCH$_3$    | H                  |
| (235) | n-pentyl      | —OCH$_3$    | —OCH$_3$    | H                  |
| (236) | 3-methylbutyl | —OCH$_3$    | —OCH$_3$    | H                  |
| (237) | n-pentyl      | —OCH$_3$    | H           | H                  |
| (238) | 3-methylbutyl | —OCH$_3$    | H           | H                  |
| (239) | n-pentyl      | —OCH$_3$    | H           | H                  |
| (240) | 3-methylbutyl | —OCH$_3$    | H           | H                  |

-continued

|       |               |             |             |          |
|-------|---------------|-------------|-------------|----------|
| (170) | H             | H           | H           | —OCH$_3$ |
| (171) | H             | H           | H           | —OCH$_3$ |
| (172) | H             | H           | —OCH$_3$    | H        |
| (173) | —OCH$_2$CH$_3$ | H           | —OCH$_3$    | H        |
| (174) | —OCH$_2$CH$_3$ | H           | H           | —OCH$_3$ |
| (175) | —OCH$_2$CH$_3$ | H           | H           | —OCH$_3$ |
| (176) | —OCH$_2$CH$_3$ | H           | —OCH$_3$    | H        |
| (177) | H             | H           | —OCH$_3$    | H        |
| (178) | H             | H           | H           | —OCH$_3$ |
| (179) | H             | H           | H           | —OCH$_3$ |
| (180) | H             | H           | —OCH$_3$    | H.       |

-continued

| | $R_7'$ | $R_{10}$ | $R_{11}$ |
|---|---|---|---|
| (181) | H | —OCH$_3$ | H |
| (182) | H | H | —OCH$_3$ |
| (183) | H | H | —OCH$_3$ |
| (184) | H | —OCH$_3$ | H |
| (185) | H | —OCH$_3$ | H |
| (186) | H | H | —OCH$_3$ |
| (187) | H | H | —OCH$_3$ |
| (188) | H | —OCH$_3$ | H |
| (189) | H | —OCH$_3$ | H |
| (190) | H | H | —OCH$_3$ |
| (191) | H | H | —OCH$_3$ |
| (192) | H | —OCH$_3$ | H |
| (193) | H | —OCH$_3$ | H |
| (194) | H | H | —OCH$_3$ |
| (195) | H | H | —OCH$_3$ |
| (196) | H | —OCH$_3$ | H |
| (197) | H | —OCH$_3$ | H |
| (198) | H | H | —OCH$_3$ |
| (199) | H | H | —OCH$_3$ |
| (200) | H | —OCH$_3$ | H |
| (201) | F | —OCH$_3$ | H |
| (202) | F | H | —OCH$_3$ |
| (203) | F | H | —OCH$_3$ |
| (204) | F | —OCH$_3$ | H |
| (205) | H | —OCH$_3$ | H |
| (206) | H | H | —OCH$_3$ |
| (207) | H | H | —OCH$_3$ |
| (208) | H | —OCH$_3$ | H |
| (209) | H | —OCH$_3$ | H |
| (210) | H | H | —OCH$_3$ |
| (211) | H | H | —OCH$_3$ |
| (212) | H | —OCH$_3$ | H |
| (213) | H | —OCH$_3$ | H |
| (214) | H | H | —OCH$_3$ |
| (215) | H | H | —OCH$_3$ |
| (216) | H | —OCH$_3$ | H |
| (217) | H | —OCH$_3$ | H |
| (218) | H | H | —OCH$_3$ |
| (219) | H | H | —OCH$_3$ |
| (220) | H | —OCH$_3$ | H |
| (221) | H | —OCH$_3$ | H |
| (222) | H | H | —OCH$_3$ |
| (223) | H | H | —OCH$_3$ |
| (224) | H | —OCH$_3$ | H |
| (225) | H | —OCH$_3$ | H |
| (226) | H | H | —OCH$_3$ |
| (227) | H | H | —OCH$_3$ |
| (228) | H | —OCH$_3$ | H |
| (229) | —OCH$_3$ | —OCH$_3$ | H |
| (230) | —OCH$_3$ | H | —OCH$_3$ |
| (231) | —OCH$_3$ | H | —OCH$_3$ |
| (232) | —OCH$_3$ | —OCH$_3$ | H |
| (233) | H | —OCH$_3$ | H |
| (234) | H | H | —OCH$_3$ |
| (235) | H | H | —OCH$_3$ |
| (236) | H | —OCH$_3$ | H |
| (237) | —OCH$_3$ | —OCH$_3$ | H |
| (238) | —OCH$_3$ | H | —OCH$_3$ |
| (239) | —OCH$_3$ | H | —OCH$_3$ |
| (240) | —OCH$_3$ | —OCH$_3$ | H. |

42. A compound according to claim 32 which is selected from compound (241) through (300):

| | $R_4$ | $R_5$ | $R_6$ |
|---|---|---|---|
| (241) | n-pentyl | —OCH$_3$ | H |
| (242) | 3-methylbutyl | —OCH$_3$ | H |
| (243) | n-pentyl | —OCH$_3$ | H |
| (244) | 3-methylbutyl | —OCH$_3$ | H |
| (245) | n-pentyl | H | Cl |
| (246) | 3-methylbutyl | H | Cl |
| (247) | n-pentyl | H | Cl |
| (248) | 3-methylbutyl | H | Cl |
| (249) | n-pentyl | —OCH$_3$ | H |
| (250) | 3-methylbutyl | —OCH$_3$ | H |
| (251) | n-pentyl | —OCH$_3$ | H |
| (252) | 3-methylbutyl | —OCH$_3$ | H |
| (253) | n-pentyl | —OCH$_3$ | H |
| (254) | 3-methylbutyl | —OCH$_3$ | H |
| (255) | n-pentyl | —OCH$_3$ | H |
| (256) | 3-methylbutyl | —OCH$_3$ | H |
| (257) | n-pentyl | H | CF$_3$ |
| (258) | 3-methylbutyl | H | CF$_3$ |
| (259) | n-pentyl | H | CF$_3$ |
| (260) | 3-methylbutyl | H | CF$_3$ |
| (261) | n-pentyl | H | H |
| (262) | 3-methylbutyl | H | H |
| (263) | n-pentyl | H | H |
| (264) | 3-methylbutyl | H | H |
| (265) | n-pentyl | CF$_3$ | H |
| (266) | 3-methylbutyl | CF$_3$ | H |
| (267) | n-pentyl | CF$_3$ | H |
| (268) | 3-methylbutyl | CF$_3$ | H |
| (269) | n-pentyl | H | Cl |
| (270) | 3-methylbutyl | H | Cl |
| (271) | n-pentyl | H | Cl |
| (272) | 3-methylbutyl | H | Cl |
| (273) | n-pentyl | H | Cl |
| (274) | 3-methylbutyl | H | Cl |
| (275) | n-pentyl | H | Cl |
| (276) | 3-methylbutyl | H | Cl |
| (277) | n-pentyl | Cl | Cl |
| (278) | 3-methylbutyl | Cl | Cl |
| (279) | n-pentyl | Cl | Cl |
| (280) | 3-methylbutyl | Cl | Cl |
| (281) | n-pentyl | Cl | H |
| (282) | 3-methylbutyl | Cl | H |
| (283) | n-pentyl | Cl | H |
| (284) | 3-methylbutyl | Cl | H |
| (285) | n-pentyl | Cl | H |
| (286) | 3-methylbutyl | Cl | H |
| (287) | n-pentyl | Cl | H |
| (288) | 3-methylbutyl | Cl | H |
| (289) | n-pentyl | H | H |
| (290) | 3-methylbutyl | H | H |
| (291) | n-pentyl | H | H |
| (292) | 3-methylbutyl | H | H |
| (293) | n-pentyl | H | H |
| (294) | 3-methylbutyl | H | H |
| (295) | n-pentyl | H | H |
| (296) | 3-methylbutyl | H | H |
| (297) | n-pentyl | H | H |
| (298) | 3-methylbutyl | H | H |
| (299) | n-pentyl | H | H |
| (300) | 3-methylbutyl | H | H |

| | $R_7$ | $R_7'$ | $R_{10}$ | $R_{11}$ |
|---|---|---|---|---|
| (241) | —OCH$_3$ | H | —OCH$_3$ | H |
| (242) | —OCH$_3$ | H | H | —OCH$_3$ |
| (243) | —OCH$_3$ | H | H | —OCH$_3$ |
| (244) | —OCH$_3$ | H | —OCH$_3$ | H |
| (245) | —OCH$_3$ | H | —OCH$_3$ | H |
| (246) | —OCH$_3$ | H | H | —OCH$_3$ |
| (247) | —OCH$_3$ | H | H | —OCH$_3$ |
| (248) | —OCH$_3$ | H | —OCH$_3$ | H |
| (249) | H | Cl | —OCH$_3$ | H |
| (250) | H | Cl | H | —OCH$_3$ |
| (251) | H | Cl | H | —OCH$_3$ |
| (252) | H | Cl | —OCH$_3$ | H |
| (253) | Cl | H | —OCH$_3$ | H |
| (254) | Cl | H | H | —OCH$_3$ |
| (255) | Cl | H | H | —OCH$_3$ |
| (256) | Cl | H | —OCH$_3$ | H |
| (257) | H | H | —OCH$_3$ | H |
| (258) | H | H | H | —OCH$_3$ |
| (259) | H | H | H | —OCH$_3$ |
| (260) | H | H | —OCH$_3$ | H |
| (261) | CF$_3$ | H | —OCH$_3$ | H |
| (262) | CF$_3$ | H | H | —OCH$_3$ |
| (263) | CF$_3$ | H | H | —OCH$_3$ |

-continued

|  | R$_4$ | R$_5$ | R$_6$ | R$_7$ |
|---|---|---|---|---|
| (264) | CF$_3$ | H | —OCH$_3$ | H |
| (265) | H | H | —OCH$_3$ | H |
| (266) | H | H | H | —OCH$_3$ |
| (267) | H | H | H | —OCH$_3$ |
| (268) | H | H | —OCH$_3$ | H |
| (269) | Cl | H | —OCH$_3$ | H |
| (270) | Cl | H | H | —OCH$_3$ |
| (271) | Cl | H | H | —OCH$_3$ |
| (272) | Cl | H | —OCH$_3$ | H |
| (273) | H | Cl | —OCH$_3$ | H |
| (274) | H | Cl | H | —OCH$_3$ |
| (275) | H | Cl | H | —OCH$_3$ |
| (276) | H | Cl | —OCH$_3$ | H |
| (277) | H | H | —OCH$_3$ | H |
| (278) | H | H | H | —OCH$_3$ |
| (279) | H | H | H | —OCH$_3$ |
| (280) | H | H | —OCH$_3$ | H |
| (281) | H | Cl | —OCH$_3$ | H |
| (282) | H | Cl | H | —OCH$_3$ |
| (283) | H | Cl | H | —OCH$_3$ |
| (284) | H | Cl | —OCH$_3$ | H |
| (285) | Cl | H | —OCH$_3$ | H |
| (286) | Cl | H | H | —OCH$_3$ |
| (287) | Cl | H | H | —OCH$_3$ |
| (288) | Cl | H | —OCH$_3$ | H |
| (289) | —(CH$_2$)$_4$CH$_3$ | H | —OCH$_3$ | H |
| (290) | —(CH$_2$)$_4$CH$_3$ | H | H | —OCH$_3$ |
| (291) | —(CH$_2$)$_4$CH$_3$ | H | H | —OCH$_3$ |
| (292) | —(CH$_2$)$_4$CH$_3$ | H | —OCH$_3$ | H |
| (293) | —O(CH$_2$)$_3$CH$_3$ | H | —OCH$_3$ | H |
| (294) | —O(CH$_2$)$_3$CH$_3$ | H | H | —OCH$_3$ |
| (295) | —O(CH$_2$)$_3$CH$_3$ | H | H | —OCH$_3$ |
| (296) | —O(CH$_2$)$_3$CH$_3$ | H | —OCH$_3$ | H |
| (297) | phenyl | H | —OCH$_3$ | H |
| (298) | phenyl | H | H | —OCH$_3$ |
| (299) | phenyl | H | H | —OCH$_3$ |
| (300) | phenyl | H | —OCH$_3$ | H. |

43. A compound according to claim 32 which is selected from compounds (301) through (350):

|  | R$_4$ | R$_5$ | R$_6$ |
|---|---|---|---|
| (301) | n-pentyl | phenyl | H |
| (302) | 3-methylbutyl | phenyl | H |
| (303) | n-pentyl | phenyl | H |
| (304) | 3-methylbutyl | phenyl | H |
| (305) | n-pentyl | H | Br |
| (306) | 3-methylbutyl | H | Br |
| (307) | n-pentyl | H | Br |
| (308) | 3-methylbutyl | H | Br |
| (309) | n-pentyl | H | H |
| (310) | 3-methylbutyl | H | H |
| (311) | n-pentyl | H | H |
| (312) | 3-methylbutyl | H | H |
| (313) | n-pentyl | Br | H |
| (314) | 3-methylbutyl | Br | H |
| (315) | n-pentyl | Br | H |
| (316) | 3-methylbutyl | Br | H |
| (317) | n-pentyl | H | H |
| (318) | 3-methylbutyl | H | H |
| (319) | n-pentyl | H | H |
| (320) | 3-methylbutyl | H | H |
| (321) | n-pentyl | H | H |
| (322) | 3-methylbutyl | H | H |
| (323) | n-pentyl | H | H |
| (324) | 3-methylbutyl | H | H |
| (325) | n-pentyl | H | H |
| (326) | 3-methylbutyl | H | H |
| (327) | n-pentyl | H | H |
| (328) | 3-methylbutyl | H | H |
| (329) | n-pentyl | F | CF$_3$ |
| (330) | 3-methylbutyl | F | CF$_3$ |
| (331) | n-pentyl | F | CF$_3$ |
| (332) | 3-methylbutyl | F | CF$_3$ |

-continued

|  | R$_4$ | R$_5$ | R$_6$ |
|---|---|---|---|
| (333) | n-pentyl | H | —OCH$_2$CH$_3$ |
| (334) | 3-methylbutyl | H | —OCH$_2$CH$_3$ |
| (335) | n-pentyl | H | —OCH$_2$CH$_3$ |
| (336) | 3-methylbutyl | H | —OCH$_2$CH$_3$ |
| (337) | n-pentyl | H | —OCH$_3$ |
| (338) | 3-methylbutyl | H | —OCH$_3$ |
| (339) | n-pentyl | H | —OCH$_3$ |
| (340) | 3-methylbutyl | H | —OCH$_3$ |
| (341) | n-pentyl | —OCH$_3$ | —OCH$_3$ |
| (342) | 3-methylbutyl | —OCH$_3$ | —OCH$_3$ |
| (343) | n-pentyl | —OCH$_3$ | —OCH$_3$ |
| (344) | 3-methylbutyl | —OCH$_3$ | —OCH$_3$ |
| (345) | n-pentyl | benzyl | H |
| (346) | 3-methylbutyl | benzyl | H |
| (347) | n-pentyl | benzyl | H |
| (348) | 3-methylbutyl | benzyl | H |

|  | R$_7$ | R$_7'$ | R$_{10}$ | R$_{11}$ |
|---|---|---|---|---|
| (301) | H | H | —OCH$_3$ | H |
| (302) | H | H | H | —OCH$_3$ |
| (303) | H | H | H | —OCH$_3$ |
| (304) | H | H | —OCH$_3$ | H |
| (305) | H | H | —OCH$_3$ | H |
| (306) | H | H | H | —OCH$_3$ |
| (307) | H | H | H | —OCH$_3$ |
| (308) | H | H | —OCH$_3$ | H |
| (309) | Br | H | —OCH$_3$ | H |
| (310) | Br | H | H | —OCH$_3$ |
| (311) | Br | H | H | —OCH$_3$ |
| (312) | Br | H | —OCH$_3$ | H |
| (313) | H | H | —OCH$_3$ | H |
| (314) | H | H | H | —OCH$_3$ |
| (315) | H | H | H | —OCH$_3$ |
| (316) | H | H | —OCH$_3$ | H |
| (317) | —(CH$_2$)$_5$CH$_3$ | H | —OCH$_3$ | H |
| (318) | —(CH$_2$)$_5$CH$_3$ | H | H | —OCH$_3$ |
| (319) | —(CH$_2$)$_5$CH$_3$ | H | H | —OCH$_3$ |
| (320) | —(CH$_2$)$_5$CH$_3$ | H | —OCH$_3$ | H |
| (321) | —OCF$_3$ | H | —OCH$_3$ | H |
| (322) | —OCF$_3$ | H | H | —OCH$_3$ |
| (323) | —OCF$_3$ | H | H | —OCH$_3$ |
| (324) | —OCF$_3$ | H | —OCH$_3$ | H |
| (325) | —O(CH$_2$)$_4$CH$_3$ | H | —OCH$_3$ | H |
| (326) | —O(CH$_2$)$_4$CH$_3$ | H | H | —OCH$_3$ |
| (327) | —O(CH$_2$)$_4$CH$_3$ | H | H | —OCH$_3$ |
| (328) | —O(CH$_2$)$_4$CH$_3$ | H | —OCH$_3$ | H |
| (329) | H | H | —OCH$_3$ | H |
| (330) | H | H | H | —OCH$_3$ |
| (331) | H | H | H | —OCH$_3$ |
| (332) | H | H | —OCH$_3$ | H |
| (333) | —OCH$_2$CH$_3$ | H | —OCH$_3$ | H |
| (334) | —OCH$_2$CH$_3$ | H | H | —OCH$_3$ |
| (335) | —OCH$_2$CH$_3$ | H | H | —OCH$_3$ |
| (336) | —OCH$_2$CH$_3$ | H | —OCH$_3$ | H |
| (337) | —OCH$_3$ | —OCH$_3$ | —OCH$_3$ | H |
| (338) | —OCH$_3$ | —OCH$_3$ | H | —OCH$_3$ |
| (339) | —OCH$_3$ | —OCH$_3$ | H | —OCH$_3$ |
| (340) | —OCH$_3$ | —OCH$_3$ | —OCH$_3$ | H |
| (341) | —OCH$_3$ | H | —OCH$_3$ | H |
| (342) | —OCH$_3$ | H | H | —OCH$_3$ |
| (343) | —OCH$_3$ | H | H | —OCH$_3$ |
| (344) | —OCH$_3$ | H | —OCH$_3$ | H |
| (345) | H | H | —OCH$_3$ | H |
| (346) | H | H | H | —OCH$_3$ |
| (347) | H | H | H | —OCH$_3$ |
| (348) | H | H | —OCH$_3$ | H. |

44. A compound according to claim 32 which is selected from compounds (349) through (404):

|  | R$_4$ | R$_5$ | R$_6$ |
|---|---|---|---|
| (349) | n-pentyl | H | phenoxy |
| (350) | 3-methylbutyl | H | phenoxy |

-continued

|  | | | |
|---|---|---|---|
| (351) | n-pentyl | H | phenoxy |
| (352) | 3-methylbutyl | H | phenoxy |
| (353) | n-pentyl | H | H |
| (354) | 3-methylbutyl | H | H |
| (355) | n-pentyl | H | H |
| (356) | 3-methylbutyl | H | H |
| (357) | n-pentyl | phenoxy | H |
| (358) | 3-methylbutyl | phenoxy | H |
| (359) | n-pentyl | phenoxy | H |
| (360) | 3-methylbutyl | phenoxy | H |
| (361) | n-pentyl | H | Br |
| (362) | 3-methylbutyl | H | Br |
| (363) | n-pentyl | H | Br |
| (364) | 3-methylbutyl | H | Br |
| (365) | n-pentyl | H | Br |
| (366) | 3-methylbutyl | H | Br |
| (367) | n-pentyl | H | Br |
| (368) | 3-methylbutyl | H | Br |
| (369) | n-pentyl | H | H |
| (370) | 3-methylbutyl | H | H |
| (371) | n-pentyl | H | H |
| (372) | 3-methylbutyl | H | H |
| (373) | n-pentyl | H | H |
| (374) | 3-methylbutyl | H | H |
| (375) | n-pentyl | H | H |
| (376) | 3-methylbutyl | H | H |
| (377) | n-pentyl | phenethyl | H |
| (378) | 3-methylbutyl | phenethyl | H |
| (379) | n-pentyl | phenethyl | H |
| (380) | 3-methylbutyl | phenethyl | H |
| (381) | n-pentyl | H | H |
| (382) | 3-methylbutyl | H | H |
| (383) | n-pentyl | H | H |
| (384) | 3-methylbutyl | H | H |
| (385) | n-pentyl | H | H |
| (386) | 3-methylbutyl | H | H |
| (387) | n-pentyl | H | H |
| (388) | 3-methylbutyl | H | H |
| (389) | n-pentyl | H | I |
| (390) | 3-methylbutyl | H | I |
| (391) | n-pentyl | H | I |
| (392) | 3-methylbutyl | H | I |
| (393) | n-pentyl | H | H |
| (394) | 3-methylbutyl | H | H |
| (395) | n-pentyl | H | H |
| (396) | 3-methylbutyl | H | H |
| (397) | n-pentyl | I | H |
| (398) | 3-methylbutyl | I | H |
| (399) | n-pentyl | I | H |
| (400) | 3-methylbutyl | I | H |
| (401) | n-pentyl | H | H |
| (402) | 3-methylbutyl | H | H |
| (403) | n-pentyl | H | H |
| (404) | 3-methylbutyl | H | H |

|  | $R_7$ | $R_7'$ | $R_{10}$ | $R_{11}$ |
|---|---|---|---|---|
| (349) | H | H | —OCH$_3$ | H |
| (350) | H | H | H | —OCH$_3$ |
| (351) | H | H | H | —OCH$_3$ |
| (352) | H | H | —OCH$_3$ | H |
| (353) | phenoxy | H | —OCH$_3$ | H |
| (354) | phenoxy | H | H | —OCH$_3$ |
| (355) | phenoxy | H | H | —OCH$_3$ |
| (356) | phenoxy | H | —OCH$_3$ | H |
| (357) | H | H | —OCH$_3$ | H |
| (358) | H | H | H | —OCH$_3$ |
| (359) | H | H | H | —OCH$_3$ |
| (360) | H | H | —OCH$_3$ | H |
| (361) | —CH$_3$ | H | —OCH$_3$ | H |
| (362) | —CH$_3$ | H | H | —OCH$_3$ |
| (363) | —CH$_3$ | H | H | —OCH$_3$ |
| (364) | —CH$_3$ | H | —OCH$_3$ | H |
| (365) | F | H | —OCH$_3$ | H |
| (366) | F | H | H | —OCH$_3$ |
| (367) | F | H | H | —OCH$_3$ |
| (368) | F | H | —OCH$_3$ | H |
| (369) | —(CH$_2$)$_6$CH$_3$ | H | —OCH$_3$ | H |
| (370) | —(CH$_2$)$_6$CH$_3$ | H | H | —OCH$_3$ |
| (371) | —(CH$_2$)$_6$CH$_3$ | H | H | —OCH$_3$ |
| (372) | —(CH$_2$)$_6$CH$_3$ | H | —OCH$_3$ | H |
| (373) | —O(CH$_2$)$_5$CH$_3$ | H | —OCH$_3$ | H |
| (374) | —O(CH$_2$)$_5$CH$_3$ | H | H | —OCH$_3$ |
| (375) | —O(CH$_2$)$_5$CH$_3$ | H | H | —OCH$_3$ |
| (376) | —O(CH$_2$)$_5$CH$_3$ | H | —OCH$_3$ | H |
| (377) | H | H | —OCH$_3$ | H |
| (378) | H | H | H | —OCH$_3$ |
| (379) | H | H | H | —OCH$_3$ |
| (380) | H | H | —OCH$_3$ | H |
| (381) | —(CH$_2$)$_7$CH$_3$ | H | —OCH$_3$ | H |
| (382) | —(CH$_2$)$_7$CH$_3$ | H | H | —OCH$_3$ |
| (383) | —(CH$_2$)$_7$CH$_3$ | H | H | —OCH$_3$ |
| (384) | —(CH$_2$)$_7$CH$_3$ | H | —OCH$_3$ | H |
| (385) | —O(CH$_2$)$_6$CH$_3$ | H | —OCH$_3$ | H |
| (386) | —O(CH$_2$)$_6$CH$_3$ | H | H | —OCH$_3$ |
| (387) | —O(CH$_2$)$_6$CH$_3$ | H | H | —OCH$_3$ |
| (388) | —O(CH$_2$)$_6$CH$_3$ | H | —OCH$_3$ | H |
| (389) | H | H | —OCH$_3$ | H |
| (390) | H | H | H | —OCH$_3$ |
| (391) | H | H | H | —OCH$_3$ |
| (392) | H | H | —OCH$_3$ | H |
| (393) | I | H | —OCH$_3$ | H |
| (394) | I | H | H | —OCH$_3$ |
| (395) | I | H | H | —OCH$_3$ |
| (396) | I | H | —OCH$_3$ | H |
| (397) | H | H | —OCH$_3$ | H |
| (398) | H | H | H | —OCH$_3$ |
| (399) | H | H | H | —OCH$_3$ |
| (400) | H | H | —OCH$_3$ | H |
| (401) | —O(CH$_2$)$_7$CH$_3$ | H | —OCH$_3$ | H |
| (402) | —O(CH$_2$)$_7$CH$_3$ | H | H | —OCH$_3$ |
| (403) | —O(CH$_2$)$_7$CH$_3$ | H | H | —OCH$_3$ |
| (404) | —O(CH$_2$)$_7$CH$_3$ | H | —OCH$_3$ | H. |

45. A method of increasing the permeability of the blood brain barrier, which method comprises administering an effective amount of a compound according to claim 1 to a patient.

46. A method of increasing the brain concentration of a CNS active compound, which method comprises administering an effective amount of a compound according to any one of claim 1 and the CNS active compound to a patient.

* * * * *